United States Patent
Ojala et al.

(10) Patent No.: US 10,883,117 B2
(45) Date of Patent: Jan. 5, 2021

(54) ADENO-ASSOCIATED VIRUS VARIANTS AND METHODS OF USE THEREOF

(71) Applicant: The Regents of the University of California, Oakland, CA (US)

(72) Inventors: David S. Ojala, Berkeley, CA (US); Jorge Santiago-Ortiz, Berkeley, CA (US); Oscar Westesson, Berkeley, CA (US); David V. Schaffer, Danville, CA (US); Ian H. Holmes, Berkeley, CA (US); John Weinstein, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 531 days.

(21) Appl. No.: 15/556,986

(22) PCT Filed: Mar. 23, 2016

(86) PCT No.: PCT/US2016/023822
§ 371 (c)(1),
(2) Date: Sep. 8, 2017

(87) PCT Pub. No.: WO2016/154344
PCT Pub. Date: Sep. 29, 2016

(65) Prior Publication Data
US 2018/0066285 A1     Mar. 8, 2018

Related U.S. Application Data

(60) Provisional application No. 62/137,580, filed on Mar. 24, 2015.

(51) Int. Cl.
*C12N 15/861*     (2006.01)
*C12N 15/864*     (2006.01)
(Continued)

(52) U.S. Cl.
CPC .......... *C12N 15/861* (2013.01); *C07K 14/005* (2013.01); *C12N 15/74* (2013.01);
(Continued)

(58) Field of Classification Search
None
See application file for complete search history.

(56) References Cited

U.S. PATENT DOCUMENTS

| | | | |
|---|---|---|---|
| 5,773,700 A | 6/1998 | Grinsven et al. | |
| 6,096,548 A | 8/2000 | Stemmer | |

(Continued)

FOREIGN PATENT DOCUMENTS

| | | |
|---|---|---|
| CA | 2379220 | 1/2001 |
| CN | 1325451 A | 12/2001 |

(Continued)

OTHER PUBLICATIONS

Koerber, et al.; "Molecular Evolution of Adeno-associated Virus for Enhanced Glial Gene Delivery"; The American Society of Gene & Cell Therapy; vol. 17, No. 12, pp. 2088-2095 (Dec. 2009).

(Continued)

*Primary Examiner* — Kevin K Hill
*Assistant Examiner* — James Joseph Graber
(74) *Attorney, Agent, or Firm* — Bozicevic, Field & Francis LLP; Paula A. Borden

(57) ABSTRACT

The present disclosure provides recombinant adeno-associated virus (rAAV) virions comprising a variant AAV capsid protein, e.g., an AAV capsid protein derived from an ancestral AAV capsid protein amino acid sequence. An rAAV virion of the present disclosure can exhibit greater infectivity of a target cell. The present disclosure also provides methods of delivering a gene product to a target cell in an individual by administering to the individual an rAAV of the present disclosure. The present disclosure also provides (Continued)

methods of generating rAAV virions that have a variant AAV capsid protein derived from an ancestral AAV capsid protein amino acid sequence.

13 Claims, 21 Drawing Sheets

Specification includes a Sequence Listing.

(51) Int. Cl.
    *C07K 14/01* (2006.01)
    *C07K 14/005* (2006.01)
    *C12N 15/74* (2006.01)
(52) U.S. Cl.
    CPC .............. *C12N 15/8645* (2013.01); *C12N 2750/14122* (2013.01); *C12N 2750/14143* (2013.01)

(56) References Cited

U.S. PATENT DOCUMENTS

| | | |
|---|---|---|
| 6,482,634 B1 | 11/2002 | Wilson et al. |
| 6,491,907 B1 | 12/2002 | Rabinowitz et al. |
| 6,596,539 B1 | 7/2003 | Stemmer et al. |
| 6,703,237 B2 | 3/2004 | Samulski et al. |
| 6,710,036 B2 | 3/2004 | Kurtzman et al. |
| 6,733,757 B2 | 5/2004 | Patel et al. |
| 6,855,314 B1 | 2/2005 | Chiorini et al. |
| 6,943,153 B1 | 9/2005 | Manning, Jr. et al. |
| 6,962,815 B2 | 11/2005 | Bartlett |
| 7,172,893 B2 | 2/2007 | Rabinowitz et al. |
| 7,252,997 B1 | 8/2007 | Hallek et al. |
| 7,254,489 B2 | 8/2007 | Mossel |
| 7,285,381 B1 | 10/2007 | Hallek et al. |
| 7,314,912 B1 | 1/2008 | Hallek et al. |
| 7,368,428 B2 | 5/2008 | Serrero |
| 7,427,396 B2 | 9/2008 | Arbetman et al. |
| 7,556,965 B2 | 7/2009 | Hallek et al. |
| 7,629,322 B2 | 12/2009 | Kleinschmidt et al. |
| 7,749,492 B2 | 7/2010 | Bartlett et al. |
| 7,968,340 B2 | 6/2011 | Hallek et al. |
| 8,524,446 B2 | 9/2013 | Gao et al. |
| 8,574,583 B2 | 11/2013 | Kay et al. |
| 8,632,764 B2 | 1/2014 | Xiao et al. |
| 8,663,624 B2 | 3/2014 | Schaffer et al. |
| 9,193,956 B2 | 11/2015 | Schaffer et al. |
| 9,233,131 B2 | 1/2016 | Schaffer et al. |
| 9,441,244 B2 | 9/2016 | Schaffer et al. |
| 9,587,282 B2 | 3/2017 | Schaffer et al. |
| 2002/0136710 A1 | 9/2002 | Samulskl et al. |
| 2002/0155610 A1 | 10/2002 | Colosi |
| 2002/0192823 A1 | 12/2002 | Bartlett |
| 2003/0143732 A1 | 7/2003 | Fosnaugh et al. |
| 2003/0171254 A1 | 9/2003 | Sasaki et al. |
| 2004/0180440 A1 | 9/2004 | Zolotukhin |
| 2005/0053922 A1 | 3/2005 | Schaffer |
| 2005/0089973 A1 | 4/2005 | Yocum et al. |
| 2005/0106558 A1 | 5/2005 | Perabo et al. |
| 2005/0148069 A1 | 7/2005 | Gage et al. |
| 2005/0220766 A1 | 10/2005 | Amalfitano et al. |
| 2005/0287122 A1 | 12/2005 | Bartlett et al. |
| 2006/0051333 A1 | 3/2006 | Arbetman et al. |
| 2006/0292117 A1 | 12/2006 | Loiler et al. |
| 2007/0020624 A1 | 1/2007 | Rubenfield et al. |
| 2007/0036760 A1 | 2/2007 | Wilson et al. |
| 2007/0172460 A1 | 7/2007 | Kleinschmidt et al. |
| 2007/0196338 A1 | 8/2007 | Samulski et al. |
| 2008/0269149 A1 | 10/2008 | Bowles et al. |
| 2009/0202490 A1 | 8/2009 | Schaffer et al. |
| 2010/0166729 A9 | 7/2010 | Madison et al. |
| 2010/0172871 A1 | 7/2010 | Flannery et al. |
| 2011/0104120 A1 | 5/2011 | Xiao et al. |
| 2011/0171262 A1 | 7/2011 | Bakker et al. |
| 2011/0236353 A1* | 9/2011 | Wilson et al. ......... A61K 48/00 424/93.2 |
| 2012/0093772 A1 | 4/2012 | Horsager et al. |
| 2013/0323302 A1 | 12/2013 | Constable et al. |
| 2014/0242031 A1 | 8/2014 | Schaffer et al. |
| 2014/0294771 A1 | 10/2014 | Schaffer et al. |
| 2014/0364338 A1 | 12/2014 | Schaffer et al. |
| 2015/0118201 A1 | 4/2015 | Xiao et al. |
| 2015/0152142 A1 | 6/2015 | Asokan et al. |
| 2015/0225702 A1 | 8/2015 | Schaffer et al. |
| 2015/0232953 A1 | 8/2015 | Schaffer et al. |
| 2015/0315610 A1 | 11/2015 | Nishie et al. |
| 2016/0017295 A1 | 1/2016 | Schaffer et al. |
| 2016/0102324 A1 | 4/2016 | Duchateau et al. |
| 2016/0184394 A1 | 6/2016 | Schaffer et al. |
| 2017/0096683 A1 | 4/2017 | Scaria et al. |
| 2019/0255192 A1 | 8/2019 | Kirn et al. |

FOREIGN PATENT DOCUMENTS

| | | |
|---|---|---|
| CN | 1826414 A | 8/2006 |
| CN | 1966082 A | 5/2007 |
| CN | 101484005 A | 7/2009 |
| CN | 101532024 A | 9/2009 |
| CN | 103561774 A | 2/2014 |
| CN | 106232618 A | 10/2014 |
| JP | 2002-518050 | 6/2002 |
| JP | 2008-523813 A | 7/2008 |
| WO | WO 1997/038723 | 10/1997 |
| WO | WO 1999/067393 | 12/1999 |
| WO | WO 2000/028004 | 5/2000 |
| WO | WO 2001/070276 | 9/2001 |
| WO | WO 2002/053703 | 7/2002 |
| WO | WO 2003/018820 | 3/2003 |
| WO | WO 2003/023032 | 3/2003 |
| WO | WO 2003/054197 | 7/2003 |
| WO | WO 2003/093436 | 11/2003 |
| WO | WO 2004/108922 | 12/2004 |
| WO | WO 2004/112727 | 12/2004 |
| WO | WO 2005/005610 | 1/2005 |
| WO | WO 2005/033321 | 4/2005 |
| WO | WO 2006/066066 | 6/2006 |
| WO | WO 2006/110689 | 10/2006 |
| WO | WO 2007/120542 | 10/2007 |
| WO | WO 2008/131951 | 11/2008 |
| WO | WO 2009/137006 | 11/2009 |
| WO | WO 2009/154452 | 12/2009 |
| WO | WO 2010/093784 | 8/2010 |
| WO | WO 2010/138263 | 12/2010 |
| WO | WO 2011/117258 | 9/2011 |
| WO | WO 2012/145601 | 10/2012 |
| WO | WO 2013/029030 | 2/2013 |
| WO | WO 2013/170078 | 11/2013 |
| WO | WO 2013/173512 | 11/2013 |
| WO | WO 2014/194132 | 12/2014 |
| WO | WO 2015/048534 | 4/2015 |
| WO | WO 2015/054653 | 4/2015 |
| WO | WO 2015/054653 A2 * | 4/2015 ............. C07K 14/00 |
| WO | WO 2015/191693 | 12/2015 |
| WO | WO 2016/141078 | 9/2016 |
| WO | WO 2016/144892 | 9/2016 |
| WO | WO 2017/023724 | 2/2017 |
| WO | WO 2017/197355 | 11/2017 |

OTHER PUBLICATIONS

Maheshri, et al.; "Directed evolution of adeno-associated virus yields enhanced gene delivery vectors"; Nature Biotechnology; vol. 24, No. 2, pp. 198-204 (Feb. 2006).

Shen, et al.; "Multiple Roles for Sialylated Glycansin Determining the Cardiopulmonary Tropism of Adeno-Associated Virus 4"; Journal of Virology; vol. 87, No. 24, pp. 13206-13213 (Dec. 2013).

Adachi, et al.; "A New Recombinant Adeno-Associated Virus (AAV)-Based Random Peptide Display Library System: Infection-Defective AAV1.9-3 As a Novel Detargeted Platform for Vector Evolution"; Gene Therapy and Regulation; vol. 5, No. 1, pp. 31-55 (Oct. 2010).

(56) References Cited

OTHER PUBLICATIONS

Akiyama, et al.; "Intraocular Injection of an Aptamer that Binds PDGF-B: A Potential Treatment for Proliferative Retinopathies"; Journal of Cellular Physiology; vol. 207, pp. 407-412 (2006).
Ali, et al.; "Restoration of photoreceptor ultrastructure and function in retinal degeneration slow mice by gene therapy"; Nature Genetics; vol. 25, pp. 306-310 (Jul. 2000).
Allocca, et al.; "Novel adeno-associated virus serotypes efficiently transduce murine photoreceptors"; Journal of Virology; vol. 81, No. 20, pp. 11372-11380 (Oct. 2007).
Asokan, et al., "Reengineering a receptor footprint of adeno-associated virus enables selective and systemic gene transfer to muscle"; Nat Biotechnol; vol. 28, No. 1, pp. 79-82 (Jan. 2010).
Attached Score Report Result Per SEQ ID No. 17 per US2002/0192823 to Bartlett Published Dec. 19, 2002.
Bichsel, et al.; "Bacterial delivery of nuclear proteins into pluripotent and differentiated cells"; PLoS One; vol. 6, No. 1, pp. 1-9 (Jan. 2011).
Blacklow, et al.; "A Seroepidemiologic Study of Adenovirus-Associated Virus Infection in Infants and Children"; Am J Epidemiol.; vol. 94, No. 4, pp. 359-366 (Oct. 1971).
Boucas, et al.; "Engineering adeno-associated virus serotype 2-based targeting vectors using a new insertion site-position 453-and single point mutations"; J Gene Med.; vol. 11, No. 12, pp. 1103-1113 (Dec. 2009).
Buch, et al., "in Contrast to AAC-Mediated Cntf Expression, AAV-Mediated Gdnf Expression Enhances Gene Replacement Therapy in Rodent Models of Retinal Degeneration"; Molecular Therapy; vol. 14, No. 5, pp. 700-709 (Nov. 2006).
Buning, et al., "Receptor targeting of adeno-associated virus vectors"; Gene Therapy; vol. 10, pp. 1142-1151 (2003).
Chadderton, et al.; "Improved Retinal Function in a Mouse Model of Dominant Retinitis Pigmentosa Following AAV-delivered Gene Therapy"; Molecular Therapy; vol. 17, No. 4, pp. 593-599 (Apr. 2009).
Choi, et al.; "AAV Hybrid Serotypes: Improved Vectors for Gene Delivery."; Current Gene Therapy; vol. 5, No. 3, pp. 299-310 (Jun. 2005).
Dalkara, et al.; "In Vivo—Directed Evolution of a New Adeno-Associated Virus for Therapeutic Outer Retinal Gene Delivery from the Vitreous"; Science Translational Medicine; vol. 5, Issue 187, 11 pp. (Jun. 12, 2013).
Dalkara, et al.; "Developing Photoreceptor Targeted AAV Variant by Directed Evolution"; ARVO Annual Meeting Abstract Search and Program Planner; vol. 2011, pp. 4381 (May 2011).
Database Geneseq [Online] Oct. 16, 2008 (Oct. 16, 2008), "Modified Adena-associated virus (hu.44) capsid protein, VP1, hu.44R2.", retrieved from EBI accession No. GSP:AEL63853, Database accession No. AEL63853.
Database Geneseq [Online] Oct. 16, 2008 (Oct. 16, 2008), "Modified Adena-associated virus (hu.44) capsid protein, VP1, hu.44R3.", retrieved from EBI accession No. GSP:AEL63854, Database accession No. AEL63854.
Davidson, et al.; "Recombinant adeno-associated virus type 2, 4, and 5 vectors: transduction of variant cell types and regions in the mammalian central nervous system."; Proc Natl Acad Sci USA.; vol. 97, No. 7, pp. 3428-3432 (Mar. 28, 2000).
Den Dunnen, et al.; "Mutation nomenclature extensions and suggestions to describe complex mutations: a discussion."; Human Mutation; vol. 15, pp. 7-12 (2000).
Diprimio, et al.; "Surface loop dynamics in adeno-associated virus capsid assembly"; Journal of Virology; vol. 82, No. 11, pp. 5178-5189 (Jun. 2008).
Erles, et al.; "Update on the prevalence of serum antibodies (IgG and IgM) to adeno-associated virus (AAV)."; J Med Virol.; vol. 59, No. 3, pp. 406-411 (Nov. 1999).
Excoffon, et al.; "Directed evolution of adeno-associated virus to an infectious respiratory virus"; Proc Natl Acad Sci USA; vol. 106, No. 10, pp. 3865-3870 (Mar. 10, 2009).

Flotte, et al.; "Gene expression from adeno-associated virus vectors in airway epithelial cells"; Am J Respir Cell Mol Biol.; vol. 7, No. 3, pp. 349-356 (Sep. 1992).
Gen Bank accession No. AAZ79678; rat AAV1 VP3 capsid protein sequence downloaded from NCBI; downloaded on Nov. 3, 2008.
GenBank accession No. ABZ10812; AAV13 capsid protein sequence downloaded from NCBI; downloaded on Nov. 3, 2008.
Girod, et al.; "Genetic capsid modifications allow efficient re-targeting of adeno-associated virus type 2"; Nat. Med.; vol. 5, No. 9, pp. 1052-1056 (Sep. 1999).
Gray, et al.; "Directed Evolution of a Novel Adeno-associated Virus (AAV) Vector That Crosses the Seizure-compromised Blood-Brain Barrier (BBB)"; Molecular Therapy; vol. 18, No. 3, pp. 570-578 (2010).
Gregory-Evans, et al.; "Ex vivo Gene Therapy Using Intravitreal Injection of GDNF-secreting Mouse Embryonic Stem Cells in a Rat Model of Retinal Degeneration"; Molecular Vision; vol. 15, pp. 962-973 (May 13, 2009).
Grieger, et al.; "Separate basic region motifs within the adeno-associated virus capsid proteins are essential for infectivity and assembly"; Journal of Virology; vol. 80, No. 11, pp. 5199-5210 (2006).
Grifman, et al.; "Incorporation of tumor-targeting peptides into recombinant adeno-associated virus capsids"; Molecular Therapy; vol. 3, No. 6, pp. 964-975 (Jun. 2001).
Grimm, et al.; "In Vitro and In Vivo Gene Therapy Vector Evolution via Multispecies Interbreeding and Retargeting of Adeno-Associated Viruses"; Journal of Virology; vol. 82, No. 12, pp. 5887-5911 (Jun. 2008).
Halbert, et al.; "Repeat transduction in the mouse lung by using adeno-associated virus vectors with different serotypes." J. Virol.; vol. 74, No. 3, pp. 1524-1532 (Feb. 2000).
Hellstrom, et al.; "Cellular tropism and transduction properties of seven adeno-associated viral vector serotypes in adult retina after intravitreal injection"; Gene Therapy; vol. 16, pp. 521-532 (2009).
Hirsch, et al.; "Directed Evolution of the AAV Capsid for Human Embryonic Stem Cell Transduction"; Molecular Therapy; vol. 17, Supp. 1, S177-S178 (May 2009).
Huttner, et al "Genetic Modifications of the Adeno-Associated Virus Type 2 Capsid Reduce Affinity to Human Serum Antibodies and Overcome Potential Limitations of Neutralizing Antibodies for the Used in Human Gene Therapy"; Blood; vol. 100, No. 11, pp. Abstract No. 5548 (Nov. 16, 2002).
Huttner, et al.; "Genetic modifications of the adeno-associated virus type 2 capsid reduce the affinity and the neutralizing effects of human serum antibodies."; Gene Ther; vol. 10, pp. 2139-2147 (Dec. 2003).
Jang, et al.; "An evolved adeno-associated viral variant enhances gene delivery and gene targeting in neural stem cells"; Mol Ther.; vol. 19, No. 4, pp. 667-675 (Apr. 2011).
Karp, et al.; "An in vitro model of differentiated human airway epithelia, Methods for establishing primary cultures"; Methods Mol Biol.; vol. 188, pp. 115-137 (2002).
Kern, et al.; "Identification of a heparin-binding motif on adeno-associated virus type 2 capsids"; Journal of Virology; vol. 77, No. 20, pp. 11072-11081 (Oct. 2003).
Khan!, et al.; "AAV-Mediated Expression Targeting of Rod and Cone Photoreceptors with a Human Rhodopsin Kinase Promoter"; Investigative Ophthalmology & Visual Science; vol. 48, No. 9, pp. 3954-3961 (Sep. 2007).
Klimczak, et al.; "A Novel Adeno-Associated Viral Variant for Efficient and Selective Intravitreal Transduction of Rat Muller Cells"; PLoS ONE; vol. 4, No. 10, pp. 1-10 (Oct. 2009).
Klimczak; "Molecular Evolution of Adeno-associated Virus for Improved Retinal Gene Therapies"; Dissertation submitted in partial fulfillment of the requirements for the degree of Doctor of Philosophy in Molecular and Cell Biology in the Graduate Division of University of California, Berkeley; 116 pages (2010).
Koerber, et al.; "DNA Shuffling of Adeno-associated Virus Yields Functionally Diverse Viral Progeny"; Molecular Therapy; vol. 16, No. 10, pp. 1703-1709 (Oct. 2008).

(56) References Cited

OTHER PUBLICATIONS

Koerber, et al.; "Engineering of a Novel AAV Vector in a Human Airway Model System for Cystic Fibrosis Gene Therapy"; AIChE Annual Meeting Abstract, 3 pages (Nov. 29, 2008).
Kwon, et al.; "Designer gene delivery vectors: molecular engineering and evolution of adeno-associated viral vectors for enhanced gene transfer"; Pharmaceutical Research; vol. 25, No. 3, pp. 489-499 (Mar. 2008).
Lai, et al.; "Long-term evaluation of AAV-mediated sFlt-1 gene therapy for ocular neovascularization in mice and monkeys"; Mol Ther.; vol. 12, No. 4, pp. 659-668 (Oct. 2005).
Li, et al.; "Engineering and Selection of Shuffled AAV Genomes: A New Strategy for Producing Targeted Biological Nanoparticles"; Molecular Therapy; vol. 16, No. 7, pp. 1252-1260 (Jul. 2008).
Li, et al.; "Generation of Novel AAV Variants by Directed Evolution for Improved CFTR Delivery to Human Ciliated Airway Epithelium"; Molecular Therapy; vol. 17, No. 12, pp. 2067-2077 (Dec. 2009).
Limberis, et al.; "Adeno-associated virus serotype 9 vectors transduce murine alveolar and nasal epithelia and can be readministered"; Proc Natl Acad Sci USA; vol. 103, No. 35, pp. 12993-12998 (Aug. 29, 2006).
Loiler, et al.; "Targeting recombinant adeno-associated virus vectors to enhance gene transfer to pancreatic islets and liver"; Gene Ther.; vol. 10, pp. 1551-1558 (2003).
Maguire, et al.; "Directed evolution of adeno-associated virus for glioma cell transduction"; J. Neurooncol.; vol. 96, pp. 337-347 (2010).
McCullum, et al.; "Random Mutagenesis by Error-Prone PCR"; Methods Mol Biol.; vol. 634, pp. 103-109; doi: 10.1007/978-1-60761-652-8_7 (2010).
Mcgee, et al., "Glial Cell Line Derived Neurotrophic Factor Delays Photoreceptor in a Transgenic Rat Model of Retinitis Pigmentosa"; Molecular Therapy; vol. 4, No. 6, pp. 622-629 (Dec. 2001).
Michelfelder, et al.; "Successful Expansion but Not Complete Restriction of Tropism of Adeno-Associated Virus by In Vivo Biopanning of Random Virus Display Peptide Libraries"; PLoS One; vol. 4, No. 4, pp. 1-13 (Apr. 2009).
Michelfelder, et al.; "Vectors selected from adeno-associated viral display peptide libraries for leukemia cell-targeted cytotoxic gene therapy"; Experimental Hematology; vol. 35, pp. 1766-1776 (2007).
Mitchell, et al.; "AAV's anatomy: Roadmap for optimizing vectors for translational success"; Curr Gene Ther.; vol. 10, No. 5, pp. 319-340 (Oct. 2010).
Moskalenko, et al; "Epitope mapping of human anti-adeno-associated virus type 2 neutralizing antibodies: implications for gene therapy and virus structure."; J. Virol.; vol. 74, No. 4, pp. 1761-1766 (Feb. 2000).
Muller, et al.; "Random peptide libraries displayed on adeno-associated virus to select for targeted gene therapy vectors"; Nat Biotechnol; vol. 21, No. 9, pp. 1040-1046 (Sep. 2003).
Nguyen, et al; "Convection-enhanced delivery of AAV-2 combined with heparin increases TK gene transfer in the rat brain."; Neuroreport; vol. 12, No. 9, pp. 1961-1964 (Jul. 3, 2001).
Nicklin, et al.; "Efficient and selective AAV2-mediated gene transfer directed to human vascular endothelial cells"; Mol. Ther.; vol. 4, No. 2, pp. 174-181 (Aug. 2001).
Opie, et al.; "Identification of Amino Acid Residues in the Capsid Proteins of Adeno-Associated Virus Type 2 that Contribute to Heparan Sulfate Proteoglycan Binding"; Journal of Virology; vol. 77, No. 12, pp. 6995-7006 (Jun. 2003).
Paddison, et al.; "Stable suppression of gene expression by RNAi in mammalian cells"; Proc. Nat'l Acad. Sci. USA; vol. 99, No. 3, pp. 1443-1448 (Feb. 5, 2002).
Padron, et al.; "Structure of adeno-associated virus type 4"; Journal of Virology; vol. 79, No. 8, pp. 5047-5058 (Apr. 2005).
Park, et al., "Intravitreal delivery of AAV8 retinoschisin results in cell type-specific gene expression and retinal rescue in the Rs1-KO mouse"; Gene Therapy; vol. 16, pp. 916-926 (2009).

Pechan, et al; "Novel anti-VEGF chimeric molecules delivered by AAV vectors for inhibition of retinal neovascularization."; Gene. Ther.; vol. 16, No. 1, pp. 10-16 (Jan. 2009).
Perabo, et al.; "Combinatorial engineering of a gene therapy vector: directed evolution of adeno-associated virus"; The Journal of Gene Medicine; vol. 8, No. 2, pp. 155-162 (Feb. 2006).
Perabo, et al.; "Heparan Sulfate Proteoglycan Binding Properties of Adeno-Associated Virus Retargeting Mutants and Consequences for Their In Vivo Tropism"; Journal of Virology; vol. 80, No. 14, pp. 7265-7269 (Jul. 2006).
Perabo, et al.; "In Vitro Selection of Viral Vectors with Modified Tropism: The Adeno-associated Virus Display"; Molecular Therapy; vol. 8, No. 1, pp. 151-157 (Jul. 2003).
Petrs-Silva, et al.; "High-efficiency transduction of the mouse retina by tyrosine-mutant AAV serotype vectors"; Molecular Therapy; vol. 17, No. 3, pp. 463-471 (Mar. 2009).
Rabinowitz, et al.; "Building a Better Vector: The Manipulation of AAV Virions"; Virology; vol. 278, pp. 301-308 (2000).
Rabinowitz, et al.; "Insertional mutagenesis of AAV2 capsid and the production of recombinant virus."; Virology; vol. 265, No. 2, pp. 274-285 (Dec. 20, 1999).
Ried, et al.; "Adeno-associated virus capsids displaying immunoglobulin-binding domains permit antibody-mediated vector retargeting to specific cell surface receptors"; J. Virol.; vol. 76, No. 9, pp. 4559-4566 (May 2002).
Ryals, et al.; "Quantifying transduction efficiencies of unmodified and tyrosine capsid mutant AAV vectors in vitro using two ocular cell lines"; Mol Vision; vol. 17, pp. 1090-1102 (Apr. 2011).
Schaffer, et al.; "Directed evolution of AAV vector mutants for enhanced gene delivery"; Abstracts of Papers American Chemical Society; vol. 227, Part 1, p. U214 (Mar. 2004).
Score result 33 for Arbetman et al WO2004112727-A2, Dec. 29, 2004.
Shen, et al.; "Characterization of the relationship of AAV capsid domain swapping to liver transduction efficiency"; Mol Ther.; vol. 15, No. 11, pp. 1955-1962 (Aug. 28, 2007).
Shi, et al.; "Capsid modifications overcome low heterogeneous expression of heparan sulfate proteoglycan that limits AAV2-mediated gene transfer and therapeutic efficacy in human ovarian carcinoma"; Gynecol. Oncol.; vol. 103, pp. 1054-1062 (2006).
Shi, et al.; "Insertional mutagenesis at positions 520 and 584 of adeno-associated virus type 2 (AAV2) capsid gene and generation of AAV2 vectors with eliminated heparin-binding ability and introduced novel tropism"; Hum. Gene Ther.; vol. 17, pp. 353-361 (Mar. 2006).
Shi, et al., "RGD inclusion in VP3 provides adeno-associated virus type 2 (AAV2)-based vectors with a heparan sulfate-independent cell entry mechanism"; Mol. Ther.; vol. 7, No. 4, pp. 515-525 (Apr. 2003).
Shi, W. et al.; "Insertional Mutagenesis of the Adeno-Associated Virus Type 2 (AAV2) Capsid Gene and Generation of AAV2 Vectors Targeted to Alternative Cell-Surface Receptors"; Human Gene Therapy; vol. 12, pp. 1697-1711 (Sep. 20, 2001).
Sonntag, et al.; "Adeno-associated virus type 2 capsids with externalized VP1/VP2 trafficking domains are generated prior to passage through the cytoplasm and are maintained until uncoating occurs in the nucleus"; Journal of Virology; vol. 80, No. 22, pp. 11040-11054 (Nov. 2006).
Steinbach, et al.; "Assembly of adeno-associated virus type 2 capsids in vitro" J of Gen Virology; vol. 78, pp. 1453-1462 (1997).
Sullivan, et al.; "Rationally designed AAV2 and AAVrh8R capsids provide improved transduction in the retina and brain"; Gene Therapy; vol. 25, pp. 205-219 (2018).
Sun, et al.; "Immune responses to adeno-associated virus and its recombinant vectors"; Gene Therapy; vol. 10, pp. 964-976 (2003).
Surace, et al.; "Delivery of Adeno-Associated Virus Vectors to the Fetal Retina: Impact of Viral Capsid Proteins on Retinal Neuronal Progenitor Transduction"; Journal of Virology; vol. 77, No. 14, pp. 7957-7962 (Jul. 2003).
Takada, et al.; "Synaptic Pathology in Retinoschisis Knockout (Rs$^{-/y}$) Mouse Retina and Modification by rAAV-Rs1 Gene Delivery"; Investigative Ophthalmology & Visual Science; vol. 49, No. 8, pp. 3677-3678 (Aug. 2008).

(56) References Cited

OTHER PUBLICATIONS

Tal; "Adeno-Associated Virus-Based Vectors in Gene Therapy"; Journal of Biomedical Science; vol. 7, No. 4, pp. 279-291 (Jul. 2000).
Tomar, et al.; "Use of Adeno-Associated Viral Vector for Delivery of Small Interfering RNA"; Oncogene; vol. 22, No. 36, pp. 5712-5715 (Aug. 28, 2003).
Van Vliet, et al.; "Proteolytic mapping of the adeno-associated virus capsid"; Mol Ther.; vol. 14, No. 6, pp. 809-821 (Dec. 2006).
Watanabe, et al.; "Tropisms of AAV for Subretinal Delivery to the Neonatal Mouse Retina and Its Application for In Vivo Rescue of Developmental Photoreceptor Disorders"; PLoS ONE; vol. 8, No. 1, 12 pages (Jan. 15, 2013).
Waterkamp, et al.; "Isolation of targeted AAV2 vectors from novel virus display libraries"; J. Gene. Med.; vol. 8, pp. 1307-1319 (Sep. 6, 2006).
White, et al.; "Genetic Modification of Adeno-Associated Viral Vector Type 2 Capsid Enhances Gene Transfer Efficiency in Polarized Human Airway Epithelial Cells"; Human Gene Therapy; vol. 19, pp. 1407-1414 (Dec. 2008).
White, et al.; "Targeted gene delivery to vascular tissue in vivo by tropism-modified adeno-associated virus vectors"; Circulation; vol. 109, pp. 513-519 (Feb. 3, 2004).
Wickham, et al.; "Increased in vitro and in vivo gene transfer by adenovirus vectors containing chimeric fiber proteins"; Journal of Virology; vol. 71, No. 11, pp. 8221-8229 (Nov. 1997).
Wobus, et al.; "Monoclonal antibodies against the adeno-associated virus type 2 (AAV-2) capsid: epitope mapping and identification of capsid domains involved in AAV-2-cell interaction and neutralization of AAV-2 infection."; J. Virol.; vol. 74, No. 19, pp. 9281-9293 (Oct. 2000).
Work, et al.; "Vascular bed-targeted in vivo gene delivery using tropism-modified adeno-associated viruses"; Mol. Ther.; vol. 13, No. 4, pp. 683-693 (Apr. 2006).
Wu, et al.; "Mutational analysis of the adeno-associated virus type 2 (AAV2) capsid gene and construction of AAV2 vectors with altered tropism"; Journal of Virology; vol. 74, No. 18, pp. 8635-8647 (Sep. 2000).
Wu, et al.; "α2,3 and α2,6 N-linked Sialic Acids Facilitate Efficient Binding and Transduction by Adeno-Associated Virus Types 1 and 6"; Journal of Virology; vol. 80, No. 18, pp. 9093-9103 (Sep. 2006).
Xiao, et al.; "Adenovirus-facilitated nuclear translocation of adeno-associated virus type 2"; Journal of Virology; vol. 76, No. 22, pp. 11505-11517 (Nov. 2002).
Xie, et al.; "The atomic structure of adeno-associated virus (AAV-2), a vector for human gene therapy"; PNAS; vol. 99, No. 16, pp. 10405-10410 (Aug. 6, 2002).
Yang, et al.; "A myocardium tropic adeno-associated virus (AAV) evolved by DNA shuffling and in vivo selection"; PNAS; vol. 106, No. 10, pp. 3946-3951 (Mar. 10, 2009).
Yang, et al.; "Directed Evolution of Adeno-Associated Virus (AAV) as Vector for Muscle Gene Therapy"; Methods in Molecular Biology; vol. 709, pp. 127-139 (2011).
Zabner, et al.; "Adeno-associated virus type 5 (AAV5) but not AAV2 binds to the apical surfaces of airway epithelia and facilitates gene transfer"; J Virol.; No. 74, No. 8, pp. 3852-3858 (Apr. 2000).
Zhao, et al.; "Molecular evolution by staggered extension process (StEP) in vitro recombination"; Nat Biotechnol; vol. 16, No. 3, pp. 258-261 (Mar. 1998).
Zolotukhin, et al.; "Recombinant adeno-associated virus purification using novel methods improves infectious titer and yield"; Gene Therapy; vol. 6, pp. 973-985 (1999).
Asuri, et al.; "Directed Evolution of Adena-associated Virus for Enhanced Gene Delivery and Gene Targeting in Human Pluripotent Stem Cells"; Molecular Therapy, vol. 20, No. 2, pp. 329-338 (Feb. 1, 2012).
Kotterman, et al.; "Engineering adeno-associated viruses for clinical gene therapy"; Nat Rev Genet; vol. 15, No. 7, pp. 445-451 (Jul. 1, 2014).
Santiago-Ortiz, et al.; "AAV Ancestral Reconstruction Library Enables Selection of Broadly Infectious Viral Variants"; Gene. Ther.; vol. 22, No. 12, pp. 934-946 (Dec. 2015).
Cronin, et al.; "Efficient transduction and optogenetic stimulation of retinal bipolar cells by a synthetic adeno-associated virus capsid and promoter"; EMBO Molecular Medicine; 16 pages (2014).
Khabou, et al.; "Insight Into the Mechanisms of Enhanced Retinal Transduction by the Engineered AAV2 Capsid Variant-7m8"; Biotechnology and Bioengineering; vol. 113, No. 12, pp. 2712-2724 (Dec. 2016).
Ortolano, et al.; "Present and Future of Adeno Associated Virus Based Gene Therapy Approaches"; Recent Patents on Endocrine, Metabolic & Immune Drug Discovery; vol. 6, pp. 47-66 (2012).
Day, et al.; "Advances in AAV Vector Development for Gene Therapy in the Retina"; Adv. Exp. Med. Biol.; vol. 801, pp. 687-693 (Dec. 2014).
Popa-Wagner, et al.; "Impact of VP1-Specific Protein Sequence Motifs on Adeno-Associated Virus Type 2 Intracellular Trafficking and Nuclear Entry"; Journal of Virology; vol. 86, No. 17, pp. 9163-9174 (Sep. 2012).
Rayaprolu, et al.; "Comparative Analysis of Adeno-Associated Virus Capsid Stability and Dynamics"; Journal of Virology; vol. 87, No. 24, pp. 13150-13160 (Dec. 2013).
Venkatakrishnan, et al.; "Structure and Dynamics of Adeno-Associated Virus Serotype 1 VP1-Unique N-Terminal Domain and Its Role in Capsid Trafficking"; Journal of Virology; vol. 87, No. 9, pp. 4974-4984 (May 2013).

\* cited by examiner

FIG. 1A

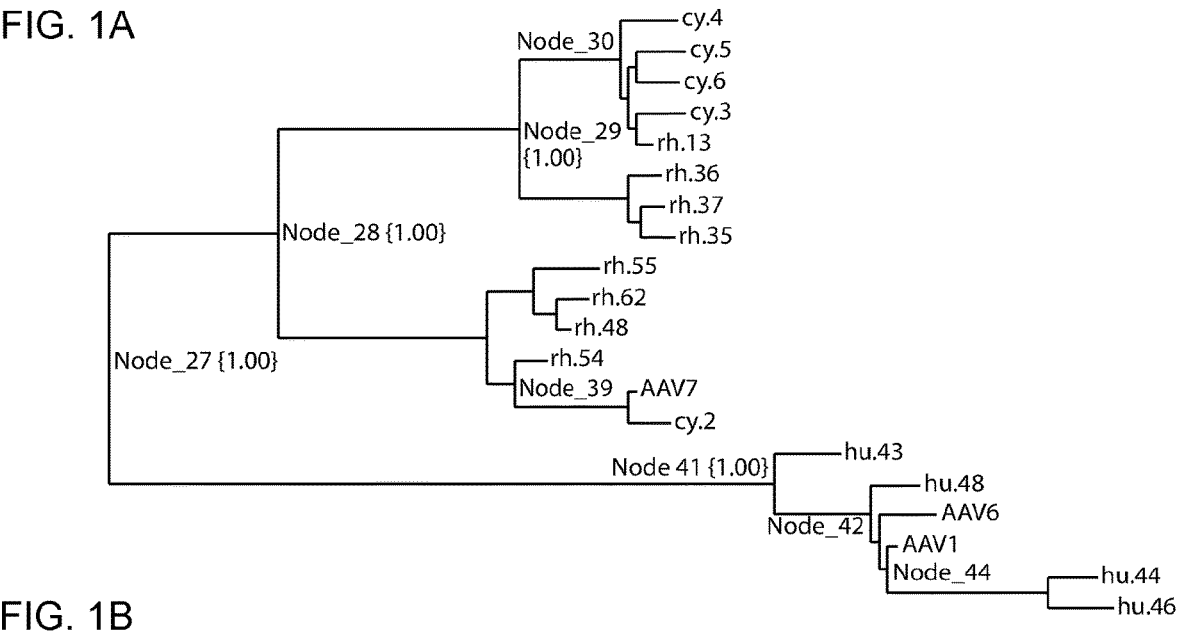

FIG. 1B

```
#=GC PP  999999999999999999999999999999999999999999999999999999994443349999999999
   hu.31 pylkynhadaefqerlkedtsfggnlgravfqakkrlleplglveeaaktapgkkrpve qspq.ep dssagigks
    cy.6 pylkynhadaefqerlqedtsfggnlgravfqakkrvleplglveegaktapgkkrpie ..... sp dsstgigkk
    rh.2 pylrynhadaefqerlqedtsfggnlgravfqakkrvleplglveegaktapgkkrpve pspqrsp dsstgigkk
   rh.51 pylrynhadaelqerlqedtsfggnlgravfqakkrvleplglveegaktapgkkrpve pspqrsp dsstgigkk
   rh.13 pylrynhadaefqerlqedtsfggnlgravfqakkrvleplglveegaktapgkkrpie ..... sp dsstgigkk
   rh.50 pylrynhadaefqerlqedtsfggnlgravfqakkrvleplglveegaktapgkkrpve pspqrsp dsstgigkk
   rh.49 phlrynhadaefqerlqedtsfggnlgravfqakkrvleplglveegaktapgkkrpve pspqrsp dsstgigkk
    cy.3 pylkynhadaefqerlqedtsfggnlgravfqakkrvleplglveevaktapgkkrpie ..... sp dsstgigkk
   hu.67 pylrynhadaefqerlqedtsfggnlgravfqakkrvleplglveeaaktapgkkrpve pspqrsp dsstgigkk
   rh.10 pylrynhadaefqerlqedtsfggnlgravfqakkrvleplglveegaktapgkkrpve pspqrsp dsstgigkk
   hu.32 pylkynhadaefqerlkedtsfggnlgravfqakkrlleplglveeaaktapgkkrpve qspq.ep dssagigks
    cy.4 pylkynhadaefqerlqedtsfggnlgravfqakkrvleplglveegaktasgkkrpie ..... sp dsstgigkk
   rh.55 pylrynhadaefqerlqedtsfggnlgravfqakkrvleplglveegaktapgkkrpve pspqrsp dsstgigkk
```

FIG. 1C

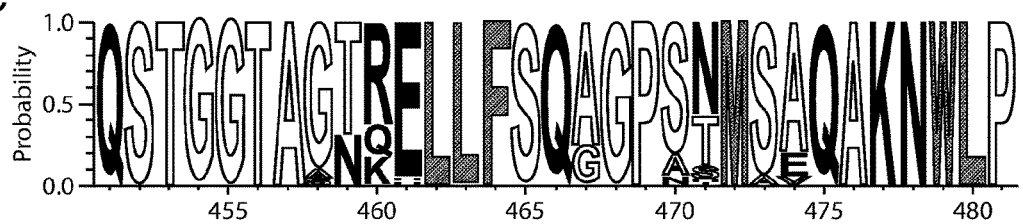

FIG. 3

MAADGYLPDWLEDNLSEGIREWWDLKPGAPKPKANQQKQDDGRGLVLPGYKYLGPFNGLDKGEP
VNAADAAALEHDKAYDQQLKAGDNPYLRYNHADAEFQERLQEDTSFGGNLGRAVFQAKKRVLEP
LGLVEEGAKTAPGKKRPVEPSPQRSPDSSTGIGKKGQQPAKKRLNFGQTGDSESVPDPQPLGEP
PAGPSGLGSGTMAAGGGAPMADNNEGADGVGNASGNWHCDSTWLGDRVITTSTRTWALPTYNNH
LYKQISSXSXGXTNDNHYFGYSTPWGYFDFNRFHCHFSPRDWQRLINNNWGFRPKRLNFKLFNI
QVKEVTTNDGVTTIANNLTSTVQVFSDSEYQLPYVLGSAHQGCLPPFPADVFMIPQYGYLTLNN
GSQAVGRSSFYCLEYFPSQMLRTGNNFTFSYTFEDVPFHSSYAHSQSLDRLMNPLIDQYLYYLX
RTQSTGGTAGXXELLFSQXGPXXMSXQAKNWLPGPCYRQQRVSKTLXQNNNSNFAWTGATKYHL
NGRXSLVNPGVAMATHKDDEXRFFPSSGVLIFGKXGAGXNNTXLXNVMXTXEEEIKTTNPVATE
XYGVVAXNLQSSNTAPXTGXVNSQGALPGMVWQNRDVYLQGPIWAKIPHTDGNFHPSPLMGGFG
LKHPPPQILIKNTPVPANPPXXFXXAKFASFITQYSTGQVSVEIEWELQKENSKRWNPEIQYTS
NYAKSXNVDFAVXXXGVYXEPRPIGTRYLTRNL

FIG. 5

| Amino acid | Theoretical distribution | Synthesized library | Post-packaging | C2C12 round 6 | 293T round 6 | IB3 round 6 | GBM round 6 | B16 round 6 |
|---|---|---|---|---|---|---|---|---|
| 264 | T, 55%. | T, 53%. | A, 52%. | Q, 86%. | A, 79%. | A, 71%. | A, 79%. | Q, 50%. |
| 266 | A, 63%. | A, 54%. | S, 57%. | S, 100%. | S, 86%. | S, 100%. | S, 86%. | A, 56%. |
| 268 | S, 70%. | S, 72%. | S, 87%. | S, 100%. | S, 100%. | S, 100%. | S, 100%. | S, 100%. |
| 448 | S, 71%. | S, 56%. | A, 52%. | S, 79%. | S, 64%. | S, 57%. | A, 57%. | S, 56%. |
| 459 | T, 69%. | T, 79%. | T, 61%. | N, 100%. | T, 100%. | T, 100%. | T, 100%. | T, 88%. |
| 460 | R, 63%. | R, 79%. | R, 78%. | R, 86%. | R, 93%. | R, 100%. | R, 93%. | R, 88%. |
| 467 | A, 75%. | A, 79%. | A, 61%. | G, 86%. | A, 93%. | G, 79%. | A, 64%. | A, 75%. |
| 470 | S, 85%. | S, 96%. | S, 87%. | A, 79%. | S, 77%. | S, 93%. | S, 79%. | S, 94%. |
| 471 | N, 60%. | N, 67%. | N, 83%. | N, 100%. | N, 79%. | T, 71%. | N, 86%. | N, 50%. |
| 474 | A, 83%. | A, 94%. | A, 87%. | A, 100%. | A, 100%. | A, 100%. | A, 100%. | A, 100%. |
| 495 | S, 75%. | S, 89%. | S, 87%. | S, 100%. | S, 67%. | S, 100%. | S, 50%. | S, 81%. |
| 516 | D, 91%. | D, 98%. | D, 100%. | D, 100%. | D, 100%. | D, 100%. | D, 100%. | D, 88%. |
| 533 | D, 86%. | D, 90%. | D, 87%. | E, 79%. | D, 93%. | D, 86%. | D, 100%. | D, 88%. |
| 547 | Q, 81%. | Q, 79%. | Q, 83%. | Q, 93%. | Q, 93%. | Q, 100%. | Q, 100%. | Q, 100%. |
| 551 | A, 50%. | A, 58%. | A, 64%. | A, 100%. | A, 67%. | A, 100%. | A, 100%. | A, 100%. |
| 555 | T, 54%. | T, 52%. | T, 59%. | T, 79%. | A, 60%. | A, 57%. | A, 71%. | A, 56%. |
| 557 | E, 86%. | E, 80%. | E, 86%. | D, 79%. | E, 67%. | E, 64%. | E, 57%. | E, 75%. |
| 561 | M, 62%. | M, 75%. | M, 68%. | M, 93%. | M, 93%. | M, 64%. | M, 57%. | M, 75%. |
| 563 | S, 80%. | S, 65%. | S, 73%. | S, 79%. | S, 87%. | N, 86%. | S, 50%. | S, 69%. |
| 577 | E, 50%. | E, 55%. | Q, 59%. | Q, 100%. | Q, 60%. | Q, 100%. | Q, 100%. | Q, 88%. |
| 583 | S, 86%. | S, 80%. | S, 77%. | S, 100%. | S, 73%. | S, 100%. | S, 100%. | S, 81%. |
| 593 | A, 45%. | Q, 49%. | Q, 45%. | Q, 79%. | A, 60%. | V, 86%. | A, 71%. | Q, 44%. |
| 596 | A, 81%. | A, 69%. | A, 68%. | T, 93%. | A, 80%. | T, 64%. | T, 79%. | T, 56%. |
| 661 | A, 71%. | A, 82%. | A, 82%. | A, 100%. | A, 64%. | A, 64%. | A, 57%. | A, 100%. |
| 662 | V, 53%. | V, 69%. | V, 68%. | V, 93%. | V, 57%. | T, 71%. | V, 64%. | V, 69%. |
| 664 | T, 66%. | T, 87%. | T, 82%. | S, 71%. | S, 50%. | T, 93%. | T, 86%. | T, 88%. |
| 665 | P, 64%. | P, 65%. | P, 77%. | P, 100%. | P, 79%. | P, 93%. | P, 71%. | P, 100%. |
| 710 | T, 87%. | T, 90%. | T, 100%. | T, 100%. | T, 100%. | T, 100%. | T, 100%. | T, 100%. |
| 717 | N, 69%. | N, 81%. | N, 77%. | N, 100%. | N, 100%. | N, 79%. | N, 79%. | N, 100%. |
| 718 | N, 60%. | N, 83%. | N, 59%. | S, 79%. | S, 93%. | N, 57%. | S, 57%. | S, 94%. |
| 719 | E, 79%. | E, 63%. | E, 82%. | E, 100%. | E, 64%. | E, 100%. | E, 100%. | E, 100%. |
| 723 | S, 68%. | S, 79%. | S, 77%. | S, 100%. | T, 57%. | S, 86%. | T, 71%. | S, 81%. |

FIG. 7

| Amino acid | C2C12 round 3 | 293T round 3 | IB3 round 3 | GBM round 3 | B16 round 3 |
|---|---|---|---|---|---|
| 264 | Q, 69%. | Q, 53%. | A, 73%. | A, 47%. | Q, 50%. |
| 266 | S, 100%. | S, 59%. | S, 87%. | S, 80%. | A, 57%. |
| 268 | S, 100%. | S, 76%. | S, 100%. | S, 93%. | S, 100%. |
| 448 | S, 56%. | S, 50%. | A, 53%. | A, 67%. | A, 71%. |
| 459 | N, 56%. | T, 88%. | T, 100%. | T, 80%. | T, 93%. |
| 460 | R, 81%. | R, 88%. | R, 93%. | R, 87%. | R, 93%. |
| 467 | A, 69%. | A, 53%. | A, 67%. | A, 73%. | A, 79%. |
| 470 | S, 69%. | S, 88%. | S, 93%. | S, 93%. | S, 92%. |
| 471 | N, 88%. | T, 65%. | N, 67%. | N, 53%. | N, 57%. |
| 474 | A, 100%. | A, 100%. | A, 93%. | A, 100%. | A, 86%. |
| 495 | S, 94%. | S, 71%. | S, 87%. | S, 87%. | S, 86%. |
| 516 | D, 100%. | D, 100%. | D, 100%. | D, 100%. | D, 100%. |
| 533 | D, 50%. | D, 94%. | D, 80%. | D, 100%. | D, 86%. |
| 547 | Q, 100%. | Q, 82%. | Q, 100%. | Q, 93%. | Q, 79%. |
| 551 | A, 75%. | A, 82%. | A, 87%. | A, 80%. | A, 93%. |
| 555 | T, 50%. | A, 82%. | A, 73%. | T, 67%. | T, 57%. |
| 557 | E, 63%. | E, 59%. | E, 73%. | E, 100%. | E, 86%. |
| 561 | M, 94%. | M, 82%. | M, 100%. | M, 73%. | M, 57%. |
| 563 | S, 75%. | S, 59%. | S, 100%. | N, 60%. | S, 71%. |
| 577 | Q, 100%. | Q, 88%. | Q, 100%. | Q, 100%. | Q, 86%. |
| 583 | S, 100%. | S, 88%. | S, 100%. | S, 100%. | S, 86%. |
| 593 | A, 50%. | Q, 53%. | A, 60%. | A, 53%. | V, 43%. |
| 596 | T, 69%. | A, 67%. | A, 73%. | A, 67%. | A, 71%. |
| 661 | A, 69%. | A, 53%. | A, 67%. | A, 80%. | A, 86%. |
| 662 | V, 88%. | V, 60%. | V, 60%. | V, 67%. | V, 64%. |
| 664 | T, 56%. | T, 73%. | T, 87%. | T, 87%. | T, 86%. |
| 665 | P, 88%. | P, 73%. | P, 73%. | P, 73%. | P, 71%. |
| 710 | T, 100%. | T, 80%. | T, 100%. | T, 87%. | T, 100%. |
| 717 | N, 69%. | N, 80%. | N, 93%. | N, 71%. | N, 93%. |
| 718 | N, 50%. | N, 47%. | S, 67%. | N, 60%. | S, 71%. |
| 719 | E, 100%. | E, 67%. | E, 93%. | E, 93%. | E, 93%. |
| 723 | S, 94%. | T, 62%. | S, 60%. | S, 71%. | S, 93%. |

FIG. 8

| Amino acid | Synthesized libary → Post-packaging | Post-packaging → C2C12 round 6 | Post-packaging → 293T round 6 | Post-packaging → IB3 round 6 | Post-packaging → GBM round 6 | Post-packaging → B16 round 6 |
|---|---|---|---|---|---|---|
| 264 | T, 53% → A, 52%. | A, 52% → Q, 86%. | 26 A | 19 A | 26 A | A, 52% → Q, 50%. |
| 266 | A, 54% → S, 57%. | 43 S | 29 S | 43 S | 29 S | S, 57% → A, 56%. |
| 268 | 15 S | 13 S | 13 S | 13 S | 13 S | 13 S |
| 448 | S, 56% → A, 52%. | A, 52% → S, 79%. | A, 52% → S, 64%. | A, 52% → S, 57%. | 5 A | A, 52% → S, 56%. |
| 459 | -18 T | T, 61% → N, 100%. | 39 T | 39 T | 39 T | 27 T |
| 460 | -1 R | 7 R | 15 R | 22 R | 15 R | 9 R |
| 467 | -18 A | A, 61% → G, 86%. | 32 A | A, 61% → G, 79%. | 3 A | 14 A |
| 470 | -9 S | S, 87% → A, 79%. | -10 S | 6 S | -8 S | 7 S |
| 471 | 16 N | 17 N | -4 N | N, 83% → T, 71%. | 3 N | -33 N |
| 474 | -7 A | 13 A | 13 A | 13 A | 13 A | 13 A |
| 495 | -2 S | 13 S | -20 S | 13 S | -37 S | -6 S |
| 516 | 2 D | 0 D | 0 D | 0 D | 0 D | -13 D |
| 533 | -3 D | D, 87% → E, 79%. | 6 D | -1 D | 13 D | 1 D |
| 547 | 4 Q | 10 Q | 11 Q | 17 Q | 17 Q | 17 Q |
| 551 | 6 A | 36 A | 3 A | 36 A | 36 A | 36 A |
| 555 | 7 T | 19 T | T, 59% → A, 60%. | T, 59% → A, 57%. | T, 59% → A, 71%. | T, 59% → A, 56%. |
| 557 | 6 E | E, 86% → D, 79%. | -20 E | -22 E | -29 E | -11 E |
| 561 | -7 M | 25 M | 25 M | -4 M | -11 M | 7 M |
| 563 | 8 S | 6 S | 14 S | S, 73% → N, 86%. | -23 S | -4 S |
| 577 | E, 55% → Q, 59%. | 41 Q | 1 Q | 41 Q | 41 Q | 28 Q |
| 583 | -3 S | 23 S | -4 S | 23 S | 23 S | 4 S |
| 593 | -4 Q | 33 Q | Q, 45% → A, 60%. | Q, 45% → V, 86%. | Q, 45% → A, 71%. | -2 Q |
| 596 | -1 A | A, 68% → T, 93%. | 12 A | A, 68% → T, 64%. | A, 68% → T, 79%. | A, 68% → T, 56%. |
| 661 | 0 A | 18 A | -18 A | -18 A | -25 A | 18 A |
| 662 | -1 V | 25 V | -11 V | V, 68% → T, 71%. | -4 V | 1 V |
| 664 | -5 T | T, 82% → S, 71%. | T, 82% → S, 50%. | 11 T | 4 T | 6 T |
| 665 | 12 P | 23 P | 1 P | 16 P | -6 P | 23 P |
| 710 | 10 T | 0 T | 0 T | 0 T | 0 T | 0 T |
| 717 | -4 N | 23 N | 23 N | 1 N | 1 N | 23 N |
| 718 | -24 N | N, 59% → S, 79%. | N, 59% → S, 93%. | -2 N | N, 59% → S, 57%. | N, 59% → S, 94%. |
| 719 | 19 E | 18 E | -18 E | 18 E | 18 E | 18 E |
| 723 | -2 S | 23 S | S, 77% → T, 57%. | 8 S | S, 77% → T, 71%. | 4 S |

FIG. 9

| Amino acid | Synthesized libary → Post-packaging | C2C12 round 3 → C2C12 round 6 | 293T round 3 → 293T round 6 | IB3 round 3 → IB3 round 6 | GBM round 3 → GBM round 6 | B16 round 3 → B16 round 6 |
|---|---|---|---|---|---|---|
| 264 | T, 53%.→ A, 52%. | 17 Q | Q, 53%.→ A, 79%. | -2 Q | 32 Q | 0 Q |
| 266 | A, 54%.→ S, 57%. | 0 S | 27 S | 13 S | 6 S | -1 S |
| 268 | 15 A | 0 A | 24 A | 0 A | 7 A | 0 A |
| 448 | S, 56%.→ A, 52%. | 22 A | 14 A | A, 53%.→ S, 57%. | -10 A | A, 71%.→ S, 56%. |
| 459 | -18 N | 44 N | 12 N | 0 N | 20 N | -5 N |
| 460 | -1 Q | 4 Q | 5 Q | 7 Q | 6 Q | -5 Q |
| 467 | -18 G | A, 69%.→ G, 86%. | 40 G | A, 67%.→ G, 79%. | -9 G | -4 G |
| 470 | -9 A | S, 69%.→ A, 79%. | -11 A | 0 A | -15 A | 1 A |
| 471 | 16 T | 13 T | T, 65%.→ N, 79%. | N, 67%.→ T, 71%. | 32 T | -7 T |
| 474 | -7 E | 0 E | 0 E | 7 E | 0 E | 14 E |
| 495 | -2 T | 6 T | -4 T | 13 T | -37 T | -4 T |
| 516 | 2 N | 0 N | 0 N | 0 N | 0 N | -13 N |
| 533 | -3 E | D, 50%.→ E, 79%. | -1 E | 6 E | 0 E | 2 E |
| 547 | 4 E | -7 E | 11 E | 0 E | 7 E | 21 E |
| 551 | 6 K | 25 K | -16 K | 13 K | 20 K | 7 K |
| 555 | 7 A | 29 A | -22 A | -16 A | T, 67%.→ A, 71%. | T, 57%.→ A, 56%. |
| 557 | 6 D | E, 63%.→ D, 79%. | 8 D | -9 D | -43 D | -11 D |
| 561 | -7 L | -1 L | 11 L | -36 L | -16 L | 18 L |
| 563 | 8 N | 4 N | 28 N | S, 100%.→ N, 86%. | N, 60%.→ S, 50%. | -3 N |
| 577 | E, 55%.→ Q, 59%. | 0 Q | -28 Q | 0 Q | 0 Q | 2 Q |
| 583 | -3 D | 0 D | -15 D | 0 D | 0 D | -4 D |
| 593 | -4 Q | A, 50%.→ Q, 79%. | Q, 53%.→ A, 60%. | A, 60%.→ V, 86%. | 18 Q | V, 43%.→ Q, 44%. |
| 596 | -1 T | 24 T | 13 T | A, 73%.→ T, 64%. | A, 67%.→ T, 79%. | A, 71%.→ T, 56%. |
| 661 | 0 E | 31 E | 11 E | -2 E | -23 E | 14 E |
| 662 | -1 T | 5 T | -3 T | V, 60%.→ T, 71%. | -2 T | 4 T |
| 664 | -5 S | T, 56%.→ S, 71%. | T, 73%.→ S, 50%. | 6 S | -1 S | 2 S |
| 665 | 12 A | 13 A | 5 A | 20 A | -2 A | 29 A |
| 710 | 10 A | 0 A | 20 A | 0 A | 13 A | 0 A |
| 717 | -4 D | 31 D | 20 D | -15 D | 7 D | 7 D |
| 718 | -24 S | N, 50%.→ S, 79%. | N, 47%.→ S, 93%. | S, 67%.→ N, 57%. | N, 60%.→ S, 57%. | 22 S |
| 719 | 19 D | 0 D | -2 D | 7 D | 7 D | 7 D |
| 723 | -2 T | 6 T | -4 T | 26 T | S, 71%.→ T, 71%. | -12 T |

FIG. 10

| Amino acid | Theoretical vs. Synth. | Synth. vs. PP | C2C12 PP vs. R3 | C2C12 PP vs. R6 | C2C12 R3 vs. R6 | 293T PP vs. R3 | 293T PP vs. R6 | 293T R3 vs. R6 | IB3 PP vs. R3 | IB3 PP vs. R6 | IB3 R3 vs. R6 | B16 PP vs. R3 | B16 PP vs. R6 | B16 R3 vs. R6 | GBM PP vs. R3 | GBM PP vs. R6 | GBM R3 vs. R6 |
|---|---|---|---|---|---|---|---|---|---|---|---|---|---|---|---|---|---|
| 264 | 0.0 | 7.6 | 99.8 | 100.0 | 0.2 | 14.6 | 0.5 | 0.4 | 57.9 | 54.4 | 0.1 | 91.5 | 95.5 | 0.1 | 0.3 | 37.4 | 1.3 |
| 266 | 0.0 | 0.0 | 81.4 | 71.8 | 0.8 | 0.1 | 0.5 | 0.4 | 0.6 | 71.8 | 3.1 | 0.1 | 0.1 | 0.1 | 0.2 | 0.5 | 0.1 |
| 268 | 0.0 | 0.1 | 3.2 | 2.9 | 0.8 | 0.1 | 2.9 | 9.9 | 3.1 | 2.9 | 0.8 | 2.9 | 3.2 | 0.8 | 0.1 | 2.9 | 1.5 |
| 448 | 0.0 | 0.0 | 0.1 | 0.4 | 0.2 | 0.1 | 0.1 | 0.1 | 0.1 | 0.1 | 0.1 | 0.1 | 0.1 | 0.3 | 0.1 | 0.1 | 0.1 |
| 459 | 0.0 | 0.1 | 0.1 | 98.7 | 64.5 | 0.5 | 55.1 | 2.6 | 60.9 | 55.1 | 0.8 | 1.4 | 0.4 | 0.2 | 0.2 | 55.1 | 6.5 |
| 460 | 0.0 | 0.0 | 0.1 | 0.1 | 0.1 | 0.2 | 0.3 | 0.1 | 0.3 | 8.5 | 1.5 | 0.3 | 0.2 | 0.2 | 0.1 | 0.3 | 0.2 |
| 467 | 0.0 | 0.1 | 0.1 | 5.3 | 12.5 | 0.1 | 1.4 | 3.3 | 0.1 | 1.3 | 2.2 | 0.1 | 0.1 | 0.1 | 0.1 | 0.1 | 0.1 |
| 470 | 0.0 | 0.3 | 0.2 | 81.4 | 3.2 | 0.3 | 39.4 | 0.5 | 7.1 | 7.1 | 0.2 | 0.3 | 1.7 | 0.3 | 0.4 | 0.9 | 0.8 |
| 471 | 0.0 | 0.1 | 0.1 | 5.0 | 2.8 | 7.6 | 0.1 | 1.8 | 0.1 | 17.5 | 0.8 | 0.1 | 0.1 | 0.1 | 0.1 | 0.1 | 0.6 |
| 474 | 0.0 | 0.1 | 3.2 | 2.9 | 0.8 | 3.4 | 2.9 | 0.7 | 0.1 | 2.9 | 1.5 | 0.3 | 3.2 | 3.8 | 3.1 | 2.9 | 0.8 |
| 495 | 0.0 | 0.0 | 0.1 | 2.9 | 1.4 | 0.2 | 0.2 | 0.1 | 0.1 | 2.9 | 3.1 | 0.1 | 0.1 | 0.1 | 0.1 | 1.5 | 1.1 |
| 516 | 0.0 | 0.5 | 0.6 | 0.6 | 0.8 | 0.6 | 0.6 | 0.7 | 0.6 | 0.6 | 0.8 | 0.6 | 3.9 | 2.8 | 0.6 | 0.6 | 0.8 |
| 533 | 0.0 | 0.0 | 0.1 | 81.4 | 0.3 | 0.1 | 0.1 | 0.1 | 0.1 | 0.1 | 0.1 | 0.1 | 0.1 | 0.1 | 3.1 | 2.9 | 0.8 |
| 547 | 0.0 | 0.0 | 1.7 | 0.6 | 1.7 | 1.2 | 0.2 | 10.2 | 5.4 | 5.0 | 0.8 | 0.0 | 5.8 | 8.8 | 0.6 | 5.0 | 1.5 |
| 551 | 0.0 | 0.1 | 5.8 | 43.3 | 11.6 | 0.2 | 0.1 | 0.1 | 0.3 | 43.3 | 3.1 | 1.0 | 53.7 | 1.7 | 0.1 | 43.3 | 6.5 |
| 555 | 0.0 | 0.0 | 0.1 | 0.2 | 0.3 | 2.4 | 0.2 | 0.2 | 0.4 | 0.1 | 0.1 | 0.1 | 0.1 | 0.1 | 0.1 | 0.4 | 0.8 |
| 557 | 0.0 | 0.0 | 0.3 | 75.9 | 1.3 | 0.4 | 0.9 | 0.3 | 0.1 | 0.2 | 37.1 | 0.0 | 2.7 | 0.5 | 3.3 | 0.5 | 62.7 |
| 561 | 0.0 | 0.1 | 1.1 | 0.8 | 0.2 | 0.0 | 0.1 | 0.4 | 31.3 | 35.0 | 100.0 | 0.1 | 0.1 | 0.1 | 0.2 | 0.0 | 3.0 |
| 563 | 0.0 | 0.0 | 0.1 | 0.1 | 0.1 | 0.6 | 0.1 | 0.5 | 18.5 | 61.3 | 0.8 | 0.4 | 0.5 | 0.1 | 0.5 | 0.2 | 0.1 |
| 577 | 0.0 | 0.1 | 72.1 | 61.3 | 0.8 | 0.0 | 0.0 | 0.0 | 66.9 | 61.3 | 0.8 | 0.2 | 0.1 | 0.1 | 66.9 | 61.3 | 0.8 |
| 583 | 0.0 | 0.0 | 11.7 | 9.6 | 0.8 | 0.0 | 0.0 | 0.0 | 10.6 | 9.6 | 0.8 | 0.0 | 0.0 | 0.0 | 10.6 | 9.6 | 0.8 |
| 593 | 0.0 | 0.0 | 3.2 | 3.5 | 0.3 | 0.1 | 0.0 | 0.1 | 0.1 | 57.0 | 98.5 | 0.0 | 0.0 | 0.0 | 0.0 | 11.5 | 0.4 |
| 596 | 0.0 | 0.0 | 0.8 | 66.4 | 0.5 | 0.1 | 0.2 | 0.1 | 0.1 | 0.4 | 0.8 | 0.1 | 0.2 | 0.3 | 0.1 | 3.9 | 2.2 |
| 661 | 0.0 | 0.0 | 0.1 | 5.5 | 22.9 | 0.1 | 0.0 | 0.0 | 0.0 | 7.0 | 8.8 | 0.0 | 6.4 | 3.8 | 0.0 | 0.1 | 0.0 |

FIG. 10 (Continued)

| | | | | | | | | | | | | | | | | | |
|---|---|---|---|---|---|---|---|---|---|---|---|---|---|---|---|---|---|
| 662 | 0.0 | 0.0 | 0.3 | 0.7 | 0.2 | 0.1 | 0.2 | 0.1 | 0.0 | 3.0 | 1.1 | 0.0 | 0.1 | 0.2 | 0.1 | 0.0 | 0.2 |
| 664 | 0.0 | 0.0 | 0.3 | 13.9 | 0.3 | 0.1 | 2.1 | 0.5 | 0.1 | 0.2 | 0.2 | 0.1 | 0.1 | 0.1 | 0.1 | 0.1 | 0.1 |
| 665 | 0.0 | 0.0 | 0.3 | 9.6 | 2.8 | 0.0 | 0.6 | 1.8 | 0.3 | 0.4 | 0.4 | 0.0 | 11.7 | 19.9 | 0.3 | 0.4 | 0.1 |
| 710 | 0.0 | 2.6 | 0.6 | 0.7 | 0.8 | 11.1 | 0.7 | 6.5 | 0.6 | 0.7 | 0.8 | 0.7 | 0.6 | 0.8 | 4.2 | 0.7 | 3.1 |
| 717 | 0.0 | 0.0 | 0.1 | 9.6 | 22.9 | 0.1 | 9.6 | 6.5 | 0.3 | 0.1 | 0.3 | 0.2 | 11.7 | 1.7 | 0.1 | 0.1 | 0.1 |
| 718 | 0.0 | 0.3 | 0.1 | 1.0 | 0.3 | 0.4 | 23.4 | 21.3 | 0.2 | 0.1 | 0.2 | 0.4 | 39.3 | 0.5 | 0.1 | 0.1 | 0.1 |
| 719 | 0.0 | 0.1 | 6.4 | 5.5 | 0.8 | 0.5 | 0.1 | 0.5 | 0.2 | 5.5 | 1.5 | 0.2 | 6.4 | 1.7 | 0.2 | 5.5 | 1.6 |
| 723 | 0.0 | 0.0 | 0.3 | 9.6 | 1.4 | 1.1 | 89.8 | 3.5 | 0.1 | 0.1 | 0.4 | 0.2 | 0.1 | 0.2 | 0.2 | 5.4 | 5.7 |

FIG. 12B

| Cell line | Biochemical defect | Glycosylation phenotype | N-glycans | O-GalNAc glycans |
|---|---|---|---|---|
| Pro5 | N/A | Full complement of complex N-glycans capped with sialic acid residues | | |
| Lec1 | Loss of N-acetylglucosyl transferase-I activity | N-glycans terminate in mannose, no complex or hybrid N-glycans | | |
| Lec2 | Unable to transport CMP-sialic acid into Golgi | N-glycans terminate in galactose, all glycans lack sialic acid | | |
| CHO-K1 | N/A | Full complement of heparan sulfate proteoglycans | | |
| pgsA | Loss of xylosyltransferase | Lacks heparan sulfate proteoglycans | | |

◇ sialic acid  ○ galactose  ● mannose  □ N-acetylglucosamine  ■ N-acetylgalactosamine
⬡ glucosamine  ⬢ iduronic acid

FIG. 16

Amino acid sequences of ancestral AAV variants

C4

MAADGYLPDWLEDNLSEGIREWWDLKPGAPKPKANQQKQDDGRGLVLPGYKYLGPFNGLDKGEPVNAADA
AALEHDKAYDQQLKAGDNPYLRYNHADAEFQERLQEDTSFGGNLGRAVFQAKKRVLEPLGLVEEGAKTAP
GKKRPVEPSPQRSPDSSTGIGKKGQQPAKKRLNFGQTGDSESVPDPQPLGEPPAGPSGLGSGTMAAGGGA
PMADNNEGADGVGNASGNWHCDSTWLGDRVITTSTRTWALPTYNNHLYKQISSASSGSTNDNHYFGYSTP
WGYFDFNRFHCHFSPRDWQRLINNNWGFRPKRLNFKLFNIQVKEVTTNDGVTTIANNLTSTVQVFSDSEY
QLPYVLGSAHQGCLPPFPADVFMIPQYGYLTLNNGSQAVGRSSFYCLEYFPSQMLRTGNNFTFSYTFEDV
PFHSSYAHSQSLDRLMNPLIDQYLYYLARTQSTGGTAGNRELLFSQGGPSNMSAQAKNWLPGPCYRQQRV
SKTLAQNNNSNFAWTGATKYHLNGRDSLVNPGVAMATHKDDEDRFFPSSGVLIFGKEGAGANNTALENVM
LTNEEEIKTTNPVATEQYGVVASNLQSSNTAPATGAVNSQGALPGMVWQNRDVYLQGPIWAKIPHTDGNF
HPSPLMGGFGLKHPPPQILIKNTPVPANPPATFTPAKFASFITQYSTGQVSVEIEWELQKENSKRWNPEI
QYTSNYAKSTNVDFAVNNEGVYSEPRPIGTRYLTRNL

C7

MAADGYLPDWLEDNLSEGIREWWDLKPGAPKPKANQQKQDDGRGLVLPGYKYLGPFNGLDKGEPVNAADA
AALEHDKAYDQQLKAGDNPYLRYNHADAEFQERLQEDTSFGGNLGRAVFQAKKRVLEPLGLVEEGAKTAP
GKKRPVEPSPQRSPDSSTGIGKKGQQPAKKRLNFGQTGDSESVPDPQPLGEPPAGPSGLGSGTMAAGGGA
PMADNNEGADGVGNASGNWHCDSTWLGDRVITTSTRTWALPTYNNHLYKQISSQSSGSTNDNHYFGYSTP
WGYFDFNRFHCHFSPRDWQRLINNNWGFRPKRLNFKLFNIQVKEVTTNDGVTTIANNLTSTVQVFSDSEY
QLPYVLGSAHQGCLPPFPADVFMIPQYGYLTLNNGSQAVGRSSFYCLEYFPSQMLRTGNNFTFSYTFEDV
PFHSSYAHSQSLDRLMNPLIDQYLYYLSRTQSTGGTAGNRELLFSQGGPANMSAQAKNWLPGPCYRQQRV
SKTLSQNNNSNFAWTGATKYHLNGRDSLVNPGVAMATHKDDEERFFPSSGVLIFGKQGAGANNTTLDNVM
MTSEEEIKTTNPVATEQYGVVASNLQSSNTAPQTGTVNSQGALPGMVWQNRDVYLQGPIWAKIPHTDGNF
HPSPLMGGFGLKHPPPQILIKNTPVPANPPAVFSPAKFASFITQYSTGQVSVEIEWELQKENSKRWNPEI
QYTSNYAKSTNVDFAVNSEGVYSEPRPIGTRYLTRNL

G4

MAADGYLPDWLEDNLSEGIREWWDLKPGAPKPKANQQKQDDGRGLVLPGYKYLGPFNGLDKGEPVNAADA
AALEHDKAYDQQLKAGDNPYLRYNHADAEFQERLQEDTSFGGNLGRAVFQAKKRVLEPLGLVEEGAKTAP
GKKRPVEPSPQRSPDSSTGIGKKGQQPAKKRLNFGQTGDSESVPDPQPLGEPPAGPSGLGSGTMAAGGGA
PMADNNEGADGVGNASGNWHCDSTWLGDRVITTSTRTWALPTYNNHLYKQISSASSGSTNDNHYFGYSTP
WGYFDFNRFHCHFSPRDWQRLINNNWGFRPKRLNFKLFNIQVKEVTTNDGVTTIANNLTSTVQVFSDSEY
QLPYVLGSAHQGCLPPFPADVFMIPQYGYLTLNNGSQAVGRSSFYCLEYFPSQMLRTGNNFTFSYTFEDV
PFHSSYAHSQSLDRLMNPLIDQYLYYLARTQSTGGTAGTRELLFSQGGPSNMSAQAKNWLPGPCYRQQRV
SKTLTQNNNSNFAWTGATKYHLNGRDSLVNPGVAMATHKDDEDRFFPSSGVLIFGKQGAGANNTALDNVM
ITNEEEIKTTNPVATEQYGVVASNLQSSNTAPATGTVNSQGALPGMVWQNRDVYLQGPIWAKIPHTDGNF
HPSPLMGGFGLKHPPPQILIKNTPVPANPPTVFSPAKFASFITQYSTGQVSVEIEWELQKENSKRWNPEI
QYTSNYAKSTNVDFAVNSEGVYTEPRPIGTRYLTRNL

FIG. 17

Consensus sequence (C4, C7, G4)
MAADGYLPDWLEDNLSEGIREWWDLKPGAPKPKANQQKQDDGRGLVLPGYKYLGPFNGLDKGEPVNAADA
AALEHDKAYDQQLKAGDNPYLRYNHADAEFQERLQEDTSFGGNLGRAVFQAKKRVLEPLGLVEEGAKTAP
GKKRPVEPSPQRSPDSSTGIGKKGQQPAKKRLNFGQTGDSESVPDPQPLGEPPAGPSGLGSGTMAAGGGA
PMADNNEGADGVGNASGNWHCDSTWLGDRVITTSTRTWALPTYNNHLYKQISSXSSGSTNDNHYFGYSTP
WGYFDFNRFHCHFSPRDWQRLINNNWGFRPKRLNFKLFNIQVKEVTTNDGVTTIANNLTSTVQVFSDSEY
QLPYVLGSAHQGCLPPFPADVFMIPQYGYLTLNNGSQAVGRSSFYCLEYFPSQMLRTGNNFTFSYTFEDV
PFHSSYAHSQSLDRLMNPLIDQYLYYLXRTQSTGGTAGXRELLFSQGGPXNMSAQAKNWLPGPCYRQQRV
SKTLXQNNNSNFAWTGATKYHLNGRDSLVNPGVAMATHKDDEXRFFPSSGVLIFGKXGAGANNTXLXNVM
XTXEEEIKTTNPVATEQYGVVASNLQSSNTAPXTGXVNSQGALPGMVWQNRDVYLQGPIWAKIPHTDGNF
HPSPLMGGFGLKHPPPQILIKNTPVPANPPXXFXPAKFASFITQYSTGQVSVEIEWELQKENSKRWNPEI
QYTSNYAKSTNVDFAVNXEGVYXEPRPIGTRYLTRNL Consensus sequence (C4, C7)
MAADGYLPDWLEDNLSEGIREWWDLKPGAPKPKANQQKQDDGRGLVLPGYKYLGPFNGLDKGEPVNAADA
AALEHDKAYDQQLKAGDNPYLRYNHADAEFQERLQEDTSFGGNLGRAVFQAKKRVLEPLGLVEEGAKTAP
GKKRPVEPSPQRSPDSSTGIGKKGQQPAKKRLNFGQTGDSESVPDPQPLGEPPAGPSGLGSGTMAAGGGA
PMADNNEGADGVGNASGNWHCDSTWLGDRVITTSTRTWALPTYNNHLYKQISSXSSGSTNDNHYFGYSTP
WGYFDFNRFHCHFSPRDWQRLINNNWGFRPKRLNFKLFNIQVKEVTTNDGVTTIANNLTSTVQVFSDSEY
QLPYVLGSAHQGCLPPFPADVFMIPQYGYLTLNNGSQAVGRSSFYCLEYFPSQMLRTGNNFTFSYTFEDV
PFHSSYAHSQSLDRLMNPLIDQYLYYLXRTQSTGGTAGNRELLFSQGGPXNMSAQAKNWLPGPCYRQQRV
SKTLSQNNNSNFAWTGATKYHLNGRDSLVNPGVAMATHKDDEXRFFPSSGVLIFGKXGAGANNTXLXNVM
XTXEEEIKTTNPVATEQYGVVASNLQSSNTAPXTGXVNSQGALPGMVWQNRDVYLQGPIWAKIPHTDGNF
HPSPLMGGFGLKHPPPQILIKNTPVPANPPAXFXPAKFASFITQYSTGQVSVEIEWELQKENSKRWNPEI
QYTSNYAKSTNVDFAVNXEGVYSEPRPIGTRYLTRNL

```
                        SEQUENCE LISTING

<160> NUMBER OF SEQ ID NOS: 18

<210> SEQ ID NO 1
<211> LENGTH: 74
<212> TYPE: PRT
<213> ORGANISM: Artificial sequence
<220> FEATURE:
<223> OTHER INFORMATION: Synthetic polypeptide

<400> SEQUENCE: 1

Pro Tyr Leu Lys Tyr Asn His Ala Asp Ala Glu Phe Gln Glu Arg Leu
1               5                   10                  15

Lys Glu Asp Thr Ser Phe Gly Gly Asn Leu Gly Arg Ala Val Phe Gln
            20                  25                  30

Ala Lys Lys Arg Leu Leu Glu Pro Leu Gly Leu Val Glu Glu Ala Ala
        35                  40                  45

Lys Thr Ala Pro Gly Lys Lys Arg Pro Val Glu Gln Ser Pro Gln Glu
    50                  55                  60

Pro Asp Ser Ser Ala Gly Ile Gly Lys Ser
65                  70

<210> SEQ ID NO 2
<211> LENGTH: 70
<212> TYPE: PRT
<213> ORGANISM: Artificial sequence
<220> FEATURE:
<223> OTHER INFORMATION: Synthetic polypeptide

<400> SEQUENCE: 2

Pro Tyr Leu Lys Tyr Asn His Ala Asp Ala Glu Phe Gln Glu Arg Leu
1               5                   10                  15

Gln Glu Asp Thr Ser Phe Gly Gly Asn Leu Gly Arg Ala Val Phe Gln
            20                  25                  30

Ala Lys Lys Arg Val Leu Glu Pro Leu Gly Leu Val Glu Glu Gly Ala
        35                  40                  45

Lys Thr Ala Pro Gly Lys Lys Arg Pro Ile Glu Ser Pro Asp Ser Ser
    50                  55                  60

Thr Gly Ile Gly Lys Lys
65                  70
```

```
<210> SEQ ID NO 3
<211> LENGTH: 75
<212> TYPE: PRT
<213> ORGANISM: Artificial sequence
<220> FEATURE:
<223> OTHER INFORMATION: Synthetic polypeptide

<400> SEQUENCE: 3

Pro Tyr Leu Arg Tyr Asn His Ala Asp Ala Glu Phe Gln Glu Arg Leu
1               5                   10                  15

Gln Glu Asp Thr Ser Phe Gly Gly Asn Leu Gly Arg Ala Val Phe Gln
            20                  25                  30

Ala Lys Lys Arg Val Leu Glu Pro Leu Gly Leu Val Glu Glu Gly Ala
        35                  40                  45

Lys Thr Ala Pro Gly Lys Lys Arg Pro Val Glu Pro Ser Pro Gln Arg
    50                  55                  60

Ser Pro Asp Ser Ser Thr Gly Ile Gly Lys Lys
65                  70                  75

<210> SEQ ID NO 4
<211> LENGTH: 75
<212> TYPE: PRT
<213> ORGANISM: Artificial sequence
<220> FEATURE:
<223> OTHER INFORMATION: Synthetic polypeptide

<400> SEQUENCE: 4

Pro Tyr Leu Arg Tyr Asn His Ala Asp Ala Glu Leu Gln Glu Arg Leu
1               5                   10                  15

Gln Glu Asp Thr Ser Phe Gly Gly Asn Leu Gly Arg Ala Val Phe Gln
            20                  25                  30

Ala Lys Lys Arg Val Leu Glu Pro Leu Gly Leu Val Glu Glu Gly Ala
        35                  40                  45

Lys Thr Ala Pro Gly Lys Lys Arg Pro Val Glu Pro Ser Pro Gln Arg
    50                  55                  60

Ser Pro Asp Ser Ser Thr Gly Ile Gly Lys Lys
65                  70                  75

<210> SEQ ID NO 5
<211> LENGTH: 75
<212> TYPE: PRT
<213> ORGANISM: Artificial sequence
<220> FEATURE:
<223> OTHER INFORMATION: Synthetic polypeptide

<400> SEQUENCE: 5

Pro His Leu Arg Tyr Asn His Ala Asp Ala Glu Phe Gln Glu Arg Leu
1               5                   10                  15

Gln Glu Asp Thr Ser Phe Gly Gly Asn Leu Gly Arg Ala Val Phe Gln
            20                  25                  30

Ala Lys Lys Arg Val Leu Glu Pro Leu Gly Leu Val Glu Glu Gly Ala
        35                  40                  45

Lys Thr Ala Pro Gly Lys Lys Arg Pro Val Glu Pro Ser Pro Gln Arg
    50                  55                  60

Ser Pro Asp Ser Ser Thr Gly Ile Gly Lys Lys
65                  70                  75

<210> SEQ ID NO 6
<211> LENGTH: 70
<212> TYPE: PRT
<213> ORGANISM: Artificial sequence
```

```
<220> FEATURE:
<223> OTHER INFORMATION: Synthetic polypeptide

<400> SEQUENCE: 6

Pro Tyr Leu Lys Tyr Asn His Ala Asp Ala Glu Phe Gln Glu Arg Leu
1               5                   10                  15

Gln Glu Asp Thr Ser Phe Gly Gly Asn Leu Gly Arg Ala Val Phe Gln
            20                  25                  30

Ala Lys Lys Arg Val Leu Glu Pro Leu Gly Leu Val Glu Glu Gly Ala
        35                  40                  45

Lys Thr Ala Ser Gly Lys Lys Arg Pro Ile Glu Ser Pro Asp Ser Ser
    50                  55                  60

Thr Gly Ile Gly Lys Lys
65                  70

<210> SEQ ID NO 7
<211> LENGTH: 737
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(737)
<223> OTHER INFORMATION: Xaa may be any amino acid.

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
            85                  90                  95

Asp Ala Glu Phe Gln Glu Arg Leu Gln Glu Asp Thr Ser Phe Gly Gly
        100                 105                 110

Asn Leu Gly Arg Ala Val Phe Gln Ala Lys Lys Arg Val Leu Glu Pro
    115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Gly Pro Ser Gly Leu Gly Ser Gly Thr Met Ala Ala Gly Gly
    195                 200                 205

Gly Ala Pro Met Ala Asp Asn Asn Glu Gly Ala Asp Gly Val Gly Asn
210                 215                 220

Ala Ser Gly Asn Trp His Cys Asp Ser Thr Trp Leu Gly Asp Arg Val
225                 230                 235                 240
```

-continued

```
Ile Thr Thr Ser Thr Arg Thr Trp Ala Leu Pro Thr Tyr Asn Asn His
            245                 250                 255

Leu Tyr Lys Gln Ile Ser Ser Xaa Ser Xaa Gly Xaa Thr Asn Asp Asn
        260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Xaa
        435                 440                 445

Arg Thr Gln Ser Thr Gly Gly Thr Ala Gly Xaa Xaa Glu Leu Leu Phe
        450                 455                 460

Ser Gln Xaa Gly Pro Xaa Xaa Met Ser Xaa Gln Ala Lys Asn Trp Leu
465                 470                 475                 480

Pro Gly Pro Cys Tyr Arg Gln Gln Arg Val Ser Lys Thr Leu Xaa Gln
                485                 490                 495

Asn Asn Asn Ser Asn Phe Ala Trp Thr Gly Ala Thr Lys Tyr His Leu
            500                 505                 510

Asn Gly Arg Xaa Ser Leu Val Asn Pro Gly Val Ala Met Ala Thr His
        515                 520                 525

Lys Asp Asp Glu Xaa Arg Phe Phe Pro Ser Ser Gly Val Leu Ile Phe
        530                 535                 540

Gly Lys Xaa Gly Ala Gly Xaa Asn Asn Thr Xaa Leu Xaa Asn Val Met
545                 550                 555                 560

Xaa Thr Xaa Glu Glu Glu Ile Lys Thr Thr Asn Pro Val Ala Thr Glu
                565                 570                 575

Xaa Tyr Gly Val Val Ala Xaa Asn Leu Gln Ser Ser Asn Thr Ala Pro
            580                 585                 590

Xaa Thr Gly Xaa Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
        610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Xaa Xaa Phe Xaa Xaa Ala Lys Phe Ala Ser Phe Ile
```

-continued

```
                660                 665                 670
Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
        690                 695                 700

Asn Tyr Ala Lys Ser Xaa Asn Val Asp Phe Ala Val Xaa Xaa Xaa Gly
705                 710                 715                 720

Val Tyr Xaa Glu Pro Arg Pro Ile Gly Thr Arg Tyr Leu Thr Arg Asn
            725                 730                 735

Leu
```

<210> SEQ ID NO 8
<211> LENGTH: 736
<212> TYPE: PRT
<213> ORGANISM: Adeno-associated virus 1

<400> SEQUENCE: 8

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
```

-continued

```
            290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
                355                 360                 365

Asp Val Phe Met Ile Pro Gln Tyr Gly Tyr Leu Thr Leu Asn Asn Gly
            370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
            435                 440                 445

Thr Gln Asn Gln Ser Gly Ser Ala Gln Asn Lys Asp Leu Leu Phe Ser
            450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
                500                 505                 510

Gly Arg Glu Ser Ile Ile Asn Pro Gly Thr Ala Met Ala Ser His Lys
            515                 520                 525

Asp Asp Glu Asp Lys Phe Phe Pro Met Ser Gly Val Met Ile Phe Gly
            530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Val Gln Tyr Thr Ser Asn
            690                 695                 700

Tyr Ala Lys Ser Ala Asn Val Asp Phe Thr Val Asp Asn Asn Gly Leu
705                 710                 715                 720
```

```
Tyr Thr Glu Pro Arg Pro Ile Gly Thr Arg Tyr Leu Thr Arg Pro Leu
                725                 730                 735

<210> SEQ ID NO 9
<211> LENGTH: 736
<212> TYPE: PRT
<213> ORGANISM: Adeno-associated virus 6

<400> SEQUENCE: 9

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asp Gly Arg Gly Leu Val Leu Pro
                35                  40                  45

Gly Tyr Lys Tyr Leu Gly Pro Phe Asn Gly Leu Asp Lys Gly Glu Pro
            50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Phe Gly Leu Val Glu Glu Gly Ala Lys Thr Ala Pro Gly Lys Lys Arg
130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
                195                 200                 205

Ala Pro Met Ala Asp Asn Asn Glu Gly Ala Asp Gly Val Gly Asn Ala
            210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
```

```
                355                 360                 365
Asp Val Phe Met Ile Pro Gln Tyr Gly Tyr Leu Thr Leu Asn Asn Gly
370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Leu Gln Ser Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735
```

<210> SEQ ID NO 10
<211> LENGTH: 737
<212> TYPE: PRT
<213> ORGANISM: Adeno-associated virus 7

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
                35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
                180                 185                 190

Pro Ala Ala Pro Ser Ser Val Gly Ser Gly Thr Val Ala Ala Gly Gly
                195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
    275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
    355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
```

-continued

```
                420                 425                 430
Asp Arg Leu Met Asn Pro Leu Ile Asp Gln Tyr Leu Tyr Tyr Leu Ala
            435                 440                 445

Arg Thr Gln Ser Asn Pro Gly Gly Thr Ala Gly Asn Arg Glu Leu Gln
        450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
            500                 505                 510

Leu Asn Gly Arg Asn Ser Leu Val Asn Pro Gly Val Ala Met Ala Thr
        515                 520                 525

His Lys Asp Asp Glu Asp Arg Phe Phe Pro Ser Ser Gly Val Leu Ile
530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 11
<211> LENGTH: 738
<212> TYPE: PRT
<213> ORGANISM: Adeno-associated virus 8

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
```

```
                50                  55                  60
Val Asn Ala Ala Asp Ala Ala Leu Glu His Asp Lys Ala Tyr Asp
 65                  70                  75                  80

Gln Gln Leu Gln Ala Gly Asp Asn Pro Tyr Leu Arg Tyr Asn His Ala
                     85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
                115                 120                 125

Leu Gly Leu Val Glu Glu Gly Ala Lys Thr Ala Pro Gly Lys Lys Arg
                130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
                180                 185                 190

Pro Ala Ala Pro Ser Gly Val Gly Pro Asn Thr Met Ala Ala Gly Gly
                195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
                260                 265                 270

Asn Thr Tyr Phe Gly Tyr Ser Thr Pro Trp Gly Tyr Phe Asp Phe Asn
                275                 280                 285

Arg Phe His Cys His Phe Ser Pro Arg Asp Trp Gln Arg Leu Ile Asn
                290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
                340                 345                 350

Leu Pro Tyr Val Leu Gly Ser Ala His Gln Gly Cys Leu Pro Pro Phe
                355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
                420                 425                 430

Leu Asp Arg Leu Met Asn Pro Leu Ile Asp Gln Tyr Leu Tyr Tyr Leu
                435                 440                 445

Ser Arg Thr Gln Thr Thr Gly Gly Thr Ala Asn Thr Gln Thr Leu Gly
                450                 455                 460

Phe Ser Gln Gly Gly Pro Asn Thr Met Ala Asn Gln Ala Lys Asn Trp
465                 470                 475                 480
```

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
            595                 600                 605

Trp Gln Asn Arg Asp Val Tyr Leu Gln Gly Pro Ile Trp Ala Lys Ile
        610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 12
<211> LENGTH: 736
<212> TYPE: PRT
<213> ORGANISM: Adeno-associated virus 9

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

```
Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525
```

Glu Gly Glu Asp Arg Phe Phe Pro Leu Ser Gly Ser Leu Ile Phe Gly
     530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 13
<211> LENGTH: 737
<212> TYPE: PRT
<213> ORGANISM: Artificial sequence
<220> FEATURE:
<223> OTHER INFORMATION: Synthetic polypeptide

<400> SEQUENCE: 13

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp Gln
65                  70                  75                  80

Gln Leu Lys Ala Gly Asp Asn Pro Tyr Leu Arg Tyr Asn His Ala Asp
                85                  90                  95

Ala Glu Phe Gln Glu Arg Leu Gln Glu Asp Thr Ser Phe Gly Gly Asn
            100                 105                 110

Leu Gly Arg Ala Val Phe Gln Ala Lys Lys Arg Val Leu Glu Pro Leu
        115                 120                 125

Gly Leu Val Glu Glu Gly Ala Lys Thr Ala Pro Gly Lys Lys Arg Pro
    130                 135                 140

Val Glu Pro Ser Pro Gln Arg Ser Pro Asp Ser Ser Thr Gly Ile Gly
145                 150                 155                 160

```
Gly Lys Lys Gly Gln Gln Pro Ala Lys Lys Arg Leu Asn Phe Gly Gln
            165                 170                 175

Thr Gly Asp Ser Glu Ser Val Pro Asp Pro Gln Pro Leu Gly Glu Pro
        180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Ala Ser Ser Gly Ser Thr Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Thr Gly Gly Thr Ala Gly Asn Arg Glu Leu Leu Phe
    450                 455                 460

Ser Gln Gly Gly Pro Ser Asn Met Ser Ala Gln Ala Lys Asn Trp Leu
465                 470                 475                 480

Pro Gly Pro Cys Tyr Arg Gln Gln Arg Val Ser Lys Thr Leu Ala Gln
                485                 490                 495

Asn Asn Asn Ser Asn Phe Ala Trp Thr Gly Ala Thr Lys Tyr His Leu
            500                 505                 510

Asn Gly Arg Asp Ser Leu Val Asn Pro Gly Val Ala Met Ala Thr His
        515                 520                 525

Lys Asp Asp Glu Asp Arg Phe Phe Pro Ser Ser Gly Val Leu Ile Phe
    530                 535                 540

Gly Lys Glu Gly Ala Gly Ala Asn Asn Thr Ala Leu Glu Asn Val Met
545                 550                 555                 560

Leu Thr Asn Glu Glu Glu Ile Lys Thr Thr Asn Pro Val Ala Thr Glu
                565                 570                 575

Gln Tyr Gly Val Val Ala Ser Asn Leu Gln Ser Ser Asn Thr Ala Pro
```

```
                580             585             590
Ala Thr Gly Ala Val Asn Ser Gln Gly Ala Leu Pro Gly Met Val Trp
            595                 600             605

Gln Asn Arg Asp Val Tyr Leu Gln Gly Pro Ile Trp Ala Lys Ile Pro
        610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Ala Thr Phe Thr Pro Ala Lys Phe Ala Ser Phe Ile
            660                 665                 670

Thr Gln Tyr Ser Thr Gly Gln Val Ser Val Glu Ile Glu Trp Glu Leu
        675                 680                 685

Gln Lys Glu Asn Ser Lys Arg Trp Asn Pro Glu Ile Gln Tyr Thr Ser
    690                 695                 700

Asn Tyr Ala Lys Ser Thr Asn Val Asp Phe Ala Val Asn Asn Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 14
<211> LENGTH: 737
<212> TYPE: PRT
<213> ORGANISM: Artificial sequence
<220> FEATURE:
<223> OTHER INFORMATION: Synthetic polypeptide

<400> SEQUENCE: 14

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Gly Pro Ser Gly Leu Gly Ser Gly Thr Met Ala Ala Gly Gly
        195                 200                 205
```

```
Gly Ala Pro Met Ala Asp Asn Glu Gly Ala Asp Val Gly Asn
    210                 215                 220

Ala Ser Gly Asn Trp His Cys Asp Ser Thr Trp Leu Gly Asp Arg Val
225             230                 235                         240

Ile Thr Thr Ser Thr Arg Thr Trp Ala Leu Pro Thr Tyr Asn Asn His
                245                 250                 255

Leu Tyr Lys Gln Ile Ser Ser Gln Ser Ser Gly Ser Thr Asn Asp Asn
            260                 265                 270

His Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305             310                 315                         320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ala Val Gly Arg Ser Ser Phe Tyr Cys Leu Glu Tyr Phe
385             390                 395                         400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Arg Thr Gln Ser Thr Gly Gly Thr Ala Gly Asn Arg Glu Leu Leu Phe
    450                 455                 460

Ser Gln Gly Gly Pro Ala Asn Met Ser Ala Gln Ala Lys Asn Trp Leu
465             470                 475                         480

Pro Gly Pro Cys Tyr Arg Gln Gln Arg Val Ser Lys Thr Leu Ser Gln
                485                 490                 495

Asn Asn Asn Ser Asn Phe Ala Trp Thr Gly Ala Thr Lys Tyr His Leu
            500                 505                 510

Asn Gly Arg Asp Ser Leu Val Asn Pro Gly Val Ala Met Ala Thr His
        515                 520                 525

Lys Asp Asp Glu Glu Arg Phe Phe Pro Ser Ser Gly Val Leu Ile Phe
    530                 535                 540

Gly Lys Gln Gly Ala Gly Ala Asn Asn Thr Thr Leu Asp Asn Val Met
545             550                 555                         560

Met Thr Ser Glu Glu Ile Lys Thr Thr Asn Pro Val Ala Thr Glu
                565                 570                 575

Gln Tyr Gly Val Val Ala Ser Asn Leu Gln Ser Ser Asn Thr Ala Pro
            580                 585                 590

Gln Thr Gly Thr Val Asn Ser Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620
```

```
His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
            645                 650                 655

Ala Asn Pro Pro Ala Val Phe Ser Pro Ala Lys Phe Ala Ser Phe Ile
        660                 665                 670

Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
690                 695                 700

Asn Tyr Ala Lys Ser Thr Asn Val Asp Phe Ala Val Asn Ser Glu Gly
705                 710                 715                 720

Val Tyr Ser Glu Pro Arg Pro Ile Gly Thr Arg Tyr Leu Thr Arg Asn
                725                 730                 735

Leu

<210> SEQ ID NO 15
<211> LENGTH: 737
<212> TYPE: PRT
<213> ORGANISM: Artificial sequence
<220> FEATURE:
<223> OTHER INFORMATION: Synthetic polypeptide

<400> SEQUENCE: 15

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
```

-continued

```
                245                 250                 255
Leu Tyr Lys Gln Ile Ser Ser Ala Ser Ser Gly Ser Thr Asn Asp Asn
            260                 265                 270
His Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Asn Phe Lys Leu Phe Asn Ile
305                 310                 315                 320
Gln Val Lys Glu Val Thr Thr Asn Asp Gly Val Thr Thr Ile Ala Asn
                325                 330                 335
Asn Leu Thr Ser Thr Val Gln Val Phe Ser Asp Ser Glu Tyr Gln Leu
            340                 345                 350
Pro Tyr Val Leu Gly Ser Ala His Gln Gly Cys Leu Pro Pro Phe Pro
            355                 360                 365
Ala Asp Val Phe Met Ile Pro Gln Tyr Gly Tyr Leu Thr Leu Asn Asn
        370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Thr Phe Ser Tyr Thr
                405                 410                 415
Phe Glu Asp Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ala
        435                 440                 445
Arg Thr Gln Ser Thr Gly Gly Thr Ala Gly Thr Arg Glu Leu Leu Phe
        450                 455                 460
Ser Gln Gly Gly Pro Ser Asn Met Ser Ala Gln Ala Lys Asn Trp Leu
465                 470                 475                 480
Pro Gly Pro Cys Tyr Arg Gln Gln Arg Val Ser Lys Thr Leu Thr Gln
                485                 490                 495
Asn Asn Asn Ser Asn Phe Ala Trp Thr Gly Ala Thr Lys Tyr His Leu
            500                 505                 510
Asn Gly Arg Asp Ser Leu Val Asn Pro Gly Val Ala Met Ala Thr His
        515                 520                 525
Lys Asp Asp Glu Asp Arg Phe Phe Pro Ser Ser Gly Val Leu Ile Phe
        530                 535                 540
Gly Lys Gln Gly Ala Gly Ala Asn Asn Thr Ala Leu Asp Asn Val Met
545                 550                 555                 560
Ile Thr Asn Glu Glu Glu Ile Lys Thr Thr Asn Pro Val Ala Thr Glu
                565                 570                 575
Gln Tyr Gly Val Val Ala Ser Asn Leu Gln Ser Ser Asn Thr Ala Pro
            580                 585                 590
Ala Thr Gly Thr Val Asn Ser Gln Gly Ala Leu Pro Gly Met Val Trp
            595                 600                 605
Gln Asn Arg Asp Val Tyr Leu Gln Gly Pro Ile Trp Ala Lys Ile Pro
        610                 615                 620
His Thr Asp Gly Asn Phe His Pro Ser Pro Leu Met Gly Gly Phe Gly
625                 630                 635                 640
Leu Lys His Pro Pro Pro Gln Ile Leu Ile Lys Asn Thr Pro Val Pro
                645                 650                 655
Ala Asn Pro Pro Thr Val Phe Ser Pro Ala Lys Phe Ala Ser Phe Ile
            660                 665                 670
```

```
Thr Gln Tyr Ser Thr Gly Gln Val Ser Val Glu Ile Glu Trp Glu Leu
            675                 680                 685

Gln Lys Glu Asn Ser Lys Arg Trp Asn Pro Glu Ile Gln Tyr Thr Ser
        690                 695                 700

Asn Tyr Ala Lys Ser Thr Asn Val Asp Phe Ala Val Asn Ser Glu Gly
705                 710                 715                 720

Val Tyr Thr Glu Pro Arg Pro Ile Gly Thr Arg Tyr Leu Thr Arg Asn
                725                 730                 735

Leu

<210> SEQ ID NO 16
<211> LENGTH: 737
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(737)
<223> OTHER INFORMATION: Xaa may be any amino acid.

<400> SEQUENCE: 16

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Xaa Ser Ser Gly Ser Thr Asn Asp Asn
            260                 265                 270
```

```
His Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
            340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Xaa
            435                 440                 445

Arg Thr Gln Ser Thr Gly Gly Thr Ala Gly Xaa Arg Glu Leu Leu Phe
            450                 455                 460

Ser Gln Gly Gly Pro Xaa Asn Met Ser Ala Gln Ala Lys Asn Trp Leu
465                 470                 475                 480

Pro Gly Pro Cys Tyr Arg Gln Gln Arg Val Ser Lys Thr Leu Xaa Gln
                485                 490                 495

Asn Asn Asn Ser Asn Phe Ala Trp Thr Gly Ala Thr Lys Tyr His Leu
            500                 505                 510

Asn Gly Arg Asp Ser Leu Val Asn Pro Gly Val Ala Met Ala Thr His
            515                 520                 525

Lys Asp Asp Glu Xaa Arg Phe Phe Pro Ser Ser Gly Val Leu Ile Phe
            530                 535                 540

Gly Lys Xaa Gly Ala Gly Ala Asn Asn Thr Xaa Leu Xaa Asn Val Met
545                 550                 555                 560

Xaa Thr Xaa Glu Glu Glu Ile Lys Thr Thr Asn Pro Val Ala Thr Glu
                565                 570                 575

Gln Tyr Gly Val Val Ala Ser Asn Leu Gln Ser Ser Asn Thr Ala Pro
            580                 585                 590

Xaa Thr Gly Xaa Val Asn Ser Gln Gly Ala Leu Pro Gly Met Val Trp
            595                 600                 605

Gln Asn Arg Asp Val Tyr Leu Gln Gly Pro Ile Trp Ala Lys Ile Pro
            610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Xaa Xaa Phe Xaa Pro Ala Lys Phe Ala Ser Phe Ile
            660                 665                 670

Thr Gln Tyr Ser Thr Gly Gln Val Ser Val Glu Ile Glu Trp Glu Leu
            675                 680                 685
```

```
Gln Lys Glu Asn Ser Lys Arg Trp Asn Pro Glu Ile Gln Tyr Thr Ser
    690             695                 700
Asn Tyr Ala Lys Ser Thr Asn Val Asp Phe Ala Val Asn Xaa Glu Gly
705             710                 715                 720
Val Tyr Xaa Glu Pro Arg Pro Ile Gly Thr Arg Tyr Leu Thr Arg Asn
            725                 730                 735
Leu
```

<210> SEQ ID NO 17
<211> LENGTH: 737
<212> TYPE: PRT
<213> ORGANISM: Artificial sequence
<220> FEATURE:
<223> OTHER INFORMATION: Synthetic polypeptide
<220> FEATURE:
<221> NAME/KEY: MISC_FEATURE
<222> LOCATION: (1)..(737)
<223> OTHER INFORMATION: Xaa may be any amino acid.

<400> SEQUENCE: 17

```
Met Ala Ala Asp Gly Tyr Leu Pro Asp Trp Leu Glu Asp Asn Leu Ser
1               5                   10                  15
Glu Gly Ile Arg Glu Trp Trp Asp Leu Lys Pro Gly Ala Pro Lys Pro
            20                  25                  30
Lys Ala Asn Gln Gln Lys Gln Asp Asp Gly Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Glu Pro Ser Pro Gln Arg Ser Pro Asp Ser Ser Thr Gly Ile
145                 150                 155                 160
Gly Lys Lys Gly Gln Gln Pro Ala Lys Lys Arg Leu Asn Phe Gly Gln
                165                 170                 175
Thr Gly Asp Ser Glu Ser Val Pro Asp Pro Gln Pro Leu Gly Glu Pro
            180                 185                 190
Pro Ala Gly Pro Ser Gly Leu Gly Ser Gly Thr Met Ala Ala Gly Gly
        195                 200                 205
Gly Ala Pro Met Ala Asp Asn Asn Glu Gly Ala Asp Gly Val Gly Asn
    210                 215                 220
Ala Ser Gly Asn Trp His Cys Asp Ser Thr Trp Leu Gly Asp Arg Val
225                 230                 235                 240
Ile Thr Thr Ser Thr Arg Thr Trp Ala Leu Pro Thr Tyr Asn Asn His
                245                 250                 255
Leu Tyr Lys Gln Ile Ser Ser Xaa Ser Ser Gly Ser Thr Asn Asp Asn
            260                 265                 270
His Tyr Phe Gly Tyr Ser Thr Pro Trp Gly Tyr Phe Asp Phe Asn Arg
        275                 280                 285
```

-continued

```
Phe His Cys His Phe Ser Pro Arg Asp Trp Gln Arg Leu Ile Asn Asn
290                 295                 300

Asn Trp Gly Phe Arg Pro Lys Arg Leu Asn Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Val Gln Val Phe Ser Asp Ser Glu Tyr Gln Leu
                340                 345                 350

Pro Tyr Val Leu Gly Ser Ala His Gln Gly Cys Leu Pro Pro Phe Pro
                355                 360                 365

Ala Asp Val Phe Met Ile Pro Gln Tyr Gly Tyr Leu Thr Leu Asn Asn
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Thr Phe Ser Tyr Thr
                405                 410                 415

Phe Glu Asp Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Xaa
                435                 440                 445

Arg Thr Gln Ser Thr Gly Gly Thr Ala Gly Asn Arg Glu Leu Leu Phe
450                 455                 460

Ser Gln Gly Gly Pro Xaa Asn Met Ser Ala Gln Ala Lys Asn Trp Leu
465                 470                 475                 480

Pro Gly Pro Cys Tyr Arg Gln Gln Arg Val Ser Lys Thr Leu Ser Gln
                485                 490                 495

Asn Asn Asn Ser Asn Phe Ala Trp Thr Gly Ala Thr Lys Tyr His Leu
                500                 505                 510

Asn Gly Arg Asp Ser Leu Val Asn Pro Gly Val Ala Met Ala Thr His
                515                 520                 525

Lys Asp Asp Glu Xaa Arg Phe Phe Pro Ser Ser Gly Val Leu Ile Phe
530                 535                 540

Gly Lys Xaa Gly Ala Gly Ala Asn Asn Thr Xaa Leu Xaa Asn Val Met
545                 550                 555                 560

Xaa Thr Xaa Glu Glu Glu Ile Lys Thr Thr Asn Pro Val Ala Thr Glu
                565                 570                 575

Gln Tyr Gly Val Val Ala Ser Asn Leu Gln Ser Ser Asn Thr Ala Pro
                580                 585                 590

Xaa Thr Gly Xaa Val Asn Ser Gln Gly Ala Leu Pro Gly Met Val Trp
                595                 600                 605

Gln Asn Arg Asp Val Tyr Leu Gln Gly Pro Ile Trp Ala Lys Ile Pro
610                 615                 620

His Thr Asp Gly Asn Phe His Pro Ser Pro Leu Met Gly Gly Phe Gly
625                 630                 635                 640

Leu Lys His Pro Pro Pro Gln Ile Leu Ile Lys Asn Thr Pro Val Pro
                645                 650                 655

Ala Asn Pro Pro Ala Xaa Phe Xaa Pro Ala Lys Phe Ala Ser Phe Ile
                660                 665                 670

Thr Gln Tyr Ser Thr Gly Gln Val Ser Val Glu Ile Glu Trp Glu Leu
                675                 680                 685

Gln Lys Glu Asn Ser Lys Arg Trp Asn Pro Glu Ile Gln Tyr Thr Ser
690                 695                 700

Asn Tyr Ala Lys Ser Thr Asn Val Asp Phe Ala Val Asn Xaa Glu Gly
```

-continued

```
705                 710                 715                 720
Val Tyr Ser Glu Pro Arg Pro Ile Gly Thr Arg Tyr Leu Thr Arg Asn
                725                 730                 735
Leu

<210> SEQ ID NO 18
<211> LENGTH: 31
<212> TYPE: PRT
<213> ORGANISM: Artificial sequence
<220> FEATURE:
<223> OTHER INFORMATION: Synthetic polypeptide

<400> SEQUENCE: 18

Gln Ser Thr Gly Gly Thr Ala Gly Thr Arg Glu Leu Leu Phe Ser Gln
1               5                   10                  15

Ala Gly Pro Ser Asn Met Ser Ala Gln Ala Lys Asn Trp Leu Pro
            20                  25                  30
```

US 10,883,117 B2

ADENO-ASSOCIATED VIRUS VARIANTS AND METHODS OF USE THEREOF

CROSS-REFERENCE

This application is a national stage application under 35 U.S.C. § 371 of PCT/US2016/023822, filed Mar. 23, 2016, which claims the benefit of U.S. Provisional Patent Application No. 62/137,580, filed Mar. 24, 2015, which applications are incorporated herein by reference in their entirety.

STATEMENT REGARDING FEDERALLY SPONSORED RESEARCH

This invention was made with government support under Grant Nos. HG004483 and EY022975 awarded by The National Institutes of Health. The government has certain rights in the invention.

INTRODUCTION

Adeno-associated virus (AAV) belongs to the Parvoviridae family and *Dependovirus* genus, whose members replicate upon co-infection with a helper virus such as adenovirus. AAV can establish a latent infection in the absence of a helper. Virions are composed of a 25 nm icosahedral capsid encompassing a 4.9 kb single-stranded DNA genome with two open reading frames: rep and cap. The non-structural rep gene encodes four regulatory proteins essential for viral replication, whereas cap encodes three structural proteins (VP1-3) that assemble into a 60-mer capsid shell. This viral capsid mediates the ability of AAV vectors to overcome many of the biological barriers of viral transduction—including cell surface receptor binding, endocytosis, intracellular trafficking, and unpackaging in the nucleus.

SUMMARY

The present disclosure provides recombinant adeno-associated virus (rAAV) virions comprising a variant AAV capsid protein, e.g., an AAV capsid protein derived from an ancestral AAV capsid protein amino acid sequence. An rAAV virion of the present disclosure can exhibit greater infectivity of a target cell. The present disclosure also provides methods of delivering a gene product to a target cell in an individual by administering to the individual an rAAV of the present disclosure. The present disclosure also provides methods of generating rAAV virions that have a variant AAV capsid protein derived from an ancestral AAV capsid protein amino acid sequence.

Aspects of the present disclosure include an rAAV virion containing: a) a variant AAV capsid protein, wherein the variant AAV capsid protein includes an amino acid sequence having at least 95% amino acid sequence identity to the sequence set forth in SEQ ID NO: 16, wherein the amino acids at positions 264, 448, 459, 470, 495, 533, 547, 555, 557, 561, 563, 593, 596, 661, 662, 664, 718 and 723 are A, A, N, S, S, D, E, A, E, L, N, A, A, A, T, T, N and S, respectively; Q, S, N, A, S, E, Q, T, D, M, S, Q, T, A, V, S, S and S, respectively; or A, A, T, S, T, D, Q, A, D, I, N, A, T, T, V, S, S and T, respectively; and b) a heterologous nucleic acid containing a nucleotide sequence encoding a gene product. In certain embodiments, the variant AAV capsid protein includes an amino acid sequence having at least 95% amino acid sequence identity to the sequence set forth in SEQ ID NO: 13. In certain embodiments, the variant AAV capsid protein includes an amino acid sequence having at least 95% amino acid sequence identity to the sequence set forth in SEQ ID NO: 14. In certain embodiments, the variant AAV capsid protein includes an amino acid sequence having at least 95% amino acid sequence identity to the sequence set forth in SEQ ID NO: 15.

In some embodiments, the variant AAV capsid protein, when present in an rAAV virion, confers increased infectivity of a target cell to the rAAV virion. In some cases, the target cell is a muscle cell or a glial cell. In certain embodiments, the rAAV virion exhibits at least 5-fold increased infectivity of a target cell compared to the infectivity of the target cell by an AAV virion comprising a wild type AAV serotype capsid protein.

In some embodiments, the variant AAV capsid protein confers altered dependency on target cell receptors for infectivity compared to the dependency conferred by a wild type AAV serotype capsid protein. In some embodiments, the rAAV virion has reduced dependency on sialic acids or heparin sulfate proteoglycans for infectivity compared to an AAV virion comprising a wild type AAV serotype capsid protein.

In any of the embodiments discussed herein, the gene product may be a polypeptide, e.g., a secreted polypeptide. In any embodiment, the polypeptide may be a troponin, laminin, collagen, lamin, selenoprotein N, protein-O-mannosyltransferase, fukutin, acetylglucosaminyltransferase-like 1A (also known as LARGE1), O-linked mannose β1,2-N-acetylglucosaminyl-transferase, or isoprenoid synthase domain-containing protein. In any of the embodiments discussed herein, the secreted polypeptide may be lipoprotein lipase, factor IX, $\alpha_1$-antitrypsin, follistatin, soluble myostatin receptor, apelin, glucagon-like peptide 1, insulin-like growth factor 1, alpha-galactosidase, iduronidase, iduronate-2-sulfatase, alpha-glucosidase, and N-acetylgalactosamine 4-sulfatase.

In any embodiment, the gene product maybe a genome editing gene product, including zinc finger nucleases, transcription activator-like effector nucleases (TALENs), and Cas9/guide RNA (gRNA) system, or a component thereof.

In any embodiment, the gene product may be a nucleic acid gene product, including an interfering RNA, a ribozyme, an antisense nucleic acid, or an aptamer.

Also provided herein is pharmaceutical composition containing a) an rAAV virion according to any embodiment set forth above or infra, and a pharmaceutically acceptable carrier, diluent, excipient, or buffer.

Also provided herein is a method of delivering a gene product to a target cell in an individual, the method comprising administering to the individual an rAAV virion according to any embodiment set forth above or infra. In some embodiments, the target cell is a muscle cell or a glial cell.

Other aspects of the present disclosure include an isolated nucleic acid containing a nucleotide sequence that encodes a variant AAV capsid protein, wherein the variant AAV capsid protein includes an amino acid sequence having at least 95% amino acid sequence identity to the sequence set forth in SEQ ID NO: 16, wherein the amino acids at positions 264, 448, 459, 470, 495, 533, 547, 555, 557, 561, 563, 593, 596, 661, 662, 664, 718 and 723 are A, A, N, S, S, D, E, A, E, L, N, A, A, A, T, T, N and S, respectively; Q, S, N, A, S, E, Q, T, D, M, S, Q, T, A, V, S, S and S, respectively; or A, A, T, S, T, D, Q, A, D, I, N, A, T, T, V, S, S and T, respectively. In some embodiments, the variant capsid protein, when present in an AAV virion, provides for increased infectivity of the AAV virion for a muscle cell or a glial cell compared to the infectivity of the muscle or glial cell, respectively, by an AAV virion comprising a wild type AAV capsid protein.

Also provided herein is an isolated, genetically modified host cell containing the nucleic acid of any embodiment set forth above or infra.

Also provided herein is a variant AAV capsid protein, wherein the variant AAV capsid protein includes an amino acid sequence having at least 95% amino acid sequence identity to the sequence set forth in SEQ ID NO: 16, wherein the amino acids at positions 264, 448, 459, 470, 495, 533, 547, 555, 557, 561, 563, 593, 596, 661, 662, 664, 718 and 723 are A, A, N, S, S, D, E, A, E, L, N, A, A, A, T, T, N and S, respectively; Q, S, N, A, S, E, Q, T, D, M, S, Q, T, A, V, S, S and S, respectively; or A, A, T, S, T, D, Q, A, D, I, N, A, T, T, V, S, S and T, respectively. In some embodiments, the variant capsid protein confers increased infectivity of a muscle or glial cell compared to the infectivity of the muscle or glial cell, respectively, by an AAV virion comprising a wild type AAV capsid protein.

Also included in the present disclosure is a method of generating rAAV virions having variant AAV capsid proteins, including subjecting an initial library of rAAV virions to a first round of selection in target cells, wherein the rAAV virions in the initial library each contain an initial AAV capsid protein having an AAV capsid protein amino acid sequence, and wherein the AAV capsid protein amino acid sequences contain an ancestral AAV capsid protein amino acid sequence that differ among each other at one or more variable residues of the ancestral AAV capsid protein amino acid sequence, thereby generating a second library of rAAV virions having variant AAV capsid proteins. In some embodiments, the method further includes determining the ancestral AAV capsid protein amino acid sequence by i) reconstructing a phylogenetic tree of a plurality of wild type AAV capsid protein amino acid sequences, ii) selecting a node of the phylogenetic tree, and iii) determining the most likely amino acid sequence at the node. In some embodiments, the method further includes estimating a confidence value at each node of the phylogenetic tree, and the selecting step comprises selecting a node of the phylogenetic tree based on the estimated confidence value at the node. In some instances, the initial AAV capsid protein has an amino acid sequence at least 94% identical to the sequence set forth in SEQ ID NO: 7.

In any embodiment, the method may comprise subjecting the second library of rAAV virions to a second round of selection. In some embodiments, the second round of selection is performed in the same target cell type as the target cells used in the first round of selection. In some embodiments, the second round of selection has increased stringency relative to the first round of selection.

In any embodiment, the target cells may be muscle cells, epithelial cells, skin cells, or glial cells. In some cases, the target cells are human embryonic kidney cells.

In some embodiments, the subjecting step includes a) infecting target cells with the library of rAAV virions, superinfecting the infected cells with a helper virus, and harvesting rAAV virions released from superinfected cells.

In any embodiment, the method may comprise isolating a rAAV virion containing a variant AAV capsid protein, wherein the isolated rAAV virion has increased infectivity, enhanced tropism, or both, compared to an AAV virion containing a wild type AAV serotype capsid protein.

Also provided herein are kits that include the subject rAAV virions, or a library of rAAV virions, and that find use in practicing the subject methods.

BRIEF DESCRIPTION OF THE DRAWINGS

FIG. 1A-1C are images that show reconstruction of ancestral adeno-associated virus (AAV) sequences. Panel B: hu.31 and hu.32-SEQ ID NO: 1; cy.6 and rh.13-SEQ ID NO: 2; rh.2, rh.50, hu.67, rh.10, and rh.55-SEQ ID NO: 3; rh.51-SEQ ID NO: 4; rh.49-SEQ ID NO: 5; cy.4-SEQ ID NO: 6. Panel C: SEQ ID NO: 18.

FIG. 3 shows an ancestral AAV cap amino acid sequence (SEQ ID NO: 7), according to an embodiment of the present disclosure.

FIG. 5 shows dominant amino acids at variable positions in AAV cap proteins of ancestral AAV variants after six rounds of selection, according to an embodiment of the present disclosure.

FIG. 7 shows dominant amino acids at variable positions in AAV cap proteins of ancestral AAV variants after three rounds of selection, according to an embodiment of the present disclosure.

FIG. 8 shows change in amino acid frequency at variable positions in AAV cap proteins of ancestral AAV variants after six rounds of selection, according to an embodiment of the present disclosure.

FIG. 9 shows change in amino acid frequency at variable positions in AAV cap proteins of ancestral AAV variants after three rounds of selection, according to an embodiment of the present disclosure.

FIG. 10 shows key variable residues in AAV cap proteins of ancestral AAV variants after selection, by Bayesian Dirichlet-multinomial model comparison tests, according to an embodiment of the present disclosure.

FIG. 12A-12B show results for a test for glycan dependency of ancestral AAV variants, according to an embodiment of the present disclosure.

FIG. 16 shows the amino acid sequence of ancestral AAV variants, C4 (SEQ ID NO: 13), C7 (SEQ ID NO: 14), and G4 (SEQ ID NO: 15).

FIG. 17 shows a consensus amino acid sequence of ancestral AAV variants, C4, C7 and G4 (top, SEQ ID NO: 16), and a consensus amino acid sequence of ancestral AAV variants, C4 and C7 (bottom, SEQ ID NO: 17).

DEFINITIONS

Figure 2:
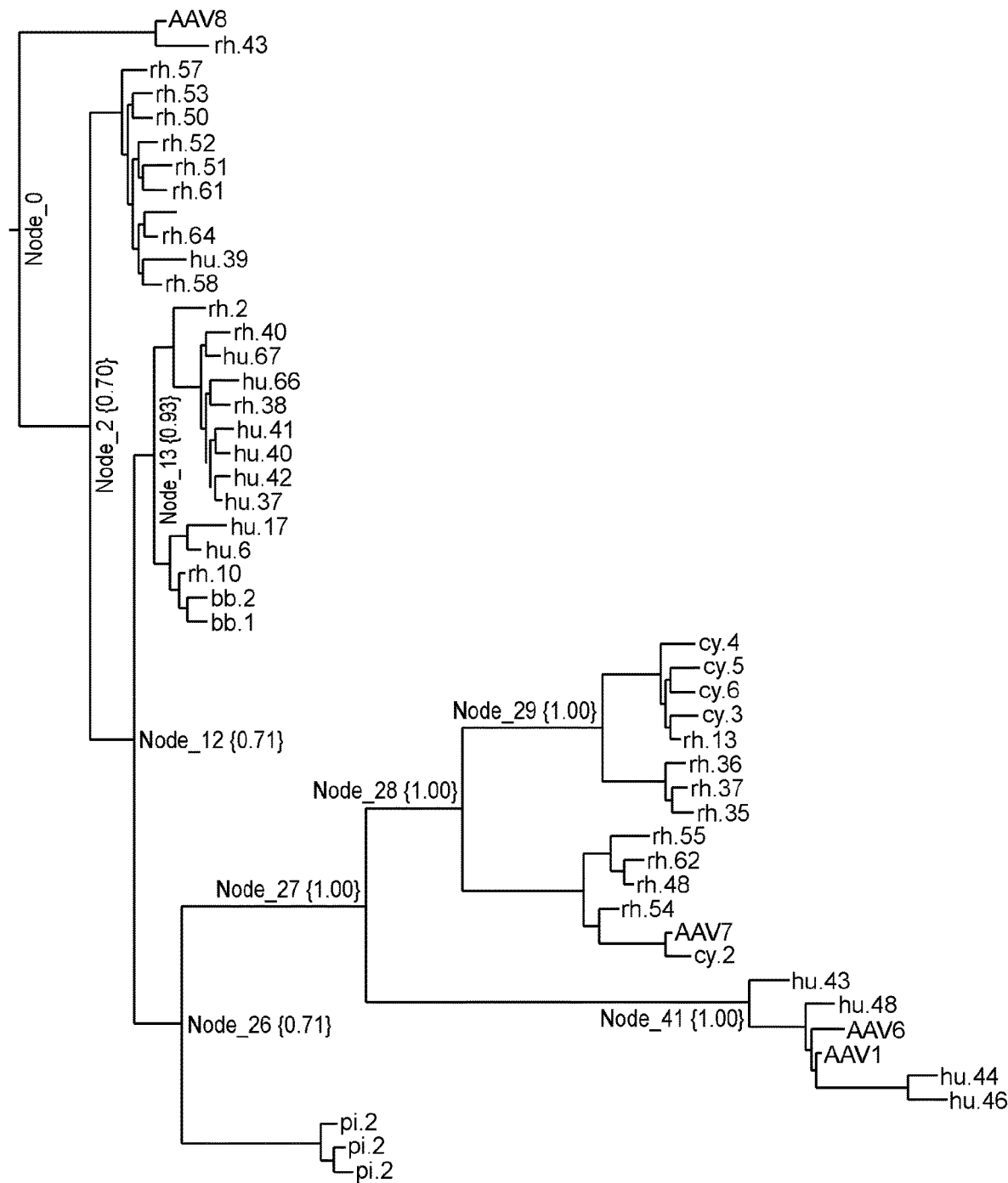
FIG. 2 shows a full phylogenetic tree for AAV ancestral sequence reconstruction.

The term "polynucleotide" refers to a polymeric form of nucleotides of any length, including deoxyribonucleotides or ribonucleotides, or analogs thereof. A polynucleotide may comprise modified nucleotides, such as methylated nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the present disclosure described herein that is a polynucleotide may encompass both the double-stranded form and each of two complementary single-stranded forms known or predicted to make up the double-stranded form.

A polynucleotide or polypeptide has a certain percent "sequence identity" to another polynucleotide or polypeptide, meaning that, when aligned, that percentage of bases or amino acids are the same when comparing the two sequences. Sequence similarity can be determined in a number of different manners. To determine sequence identity, sequences can be aligned using the methods and computer programs, including BLAST, available over the world wide web at ncbi(dot)nlm(dot)nih(dot)gov/BLAST/. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970)

Of interest is the BestFit program using the local homology algorithm of Smith Waterman (Advances in Applied Mathematics 2: 482-489 (1981) to determine sequence identity. The gap generation penalty will generally range from 1 to 5, usually 2 to 4 and in many embodiments will be 3. The gap extension penalty will generally range from about 0.01 to 0.20 and in many instances will be 0.10. The program has default parameters determined by the sequences inputted to be compared. Preferably, the sequence identity is determined using the default parameters determined by the program. This program is available also from Genetics Computing Group (GCG) package, from Madison, Wis., USA.

Another program of interest is the FastDB algorithm. FastDB is described in Current Methods in Sequence Comparison and Analysis, Macromolecule Sequencing and Synthesis, Selected Methods and Applications, pp. 127-149, 1988, Alan R. Liss, Inc. Percent sequence identity is calculated by FastDB based upon the following parameters:

Mismatch Penalty: 1.00;
Gap Penalty: 1.00;
Gap Size Penalty: 0.33; and
Joining Penalty: 30.0.

A "gene" refers to a polynucleotide containing at least one open reading frame that is capable of encoding a particular protein after being transcribed and translated.

A "small interfering" or "short interfering RNA" or siRNA is a RNA duplex of nucleotides that is targeted to a gene interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA that is a fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

The terms "polypeptide," "peptide," and "protein" are used interchangeably herein to refer to polymers of amino acids of any length. The terms also encompass an amino acid polymer that has been modified; for example, disulfide bond formation, glycosylation, lipidation, phosphorylation, or conjugation with a labeling component. Polypeptides such as anti-angiogenic polypeptides, neuroprotective polypeptides, and the like, when discussed in the context of delivering a gene product to a mammalian subject, and compositions therefor, refer to the respective intact polypeptide, or any fragment or genetically engineered derivative thereof, which retains the desired biochemical function of the intact protein. Similarly, references to nucleic acids encoding anti-angiogenic polypeptides, nucleic acids encoding neuroprotective polypeptides, and other such nucleic acids for use in delivery of a gene product to a mammalian subject (which may be referred to as "transgenes" to be delivered to a recipient cell), include polynucleotides encoding the intact polypeptide or any fragment or genetically engineered derivative possessing the desired biochemical function.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "host," "subject," and "patient" are used interchangeably herein, and refer to a mammal, including, but not limited to, human and non-human primates, including simians and humans; mammalian sport animals (e.g., horses); mammalian farm animals (e.g., sheep, goats, etc.); mammalian pets (dogs, cats, etc.); and rodents (e.g., mice, rats, etc.).

"AAV" is an abbreviation for adeno-associated virus, and may be used to refer to the virus itself or derivatives thereof. The term covers all subtypes and both naturally occurring and recombinant forms, except where required otherwise. The abbreviation "rAAV" refers to recombinant adeno-associated virus, also referred to as a recombinant AAV vector (or "rAAV vector"). The term "AAV" includes AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, and ovine AAV. "Primate AAV" refers to AAV that infect primates, "non-primate AAV" refers to AAV that infect non-primate mammals, "bovine AAV" refers to AAV that infect bovine mammals, etc.

An "rAAV vector" as used herein refers to an AAV vector comprising a polynucleotide sequence not of AAV origin (i.e., a polynucleotide heterologous to AAV), typically a sequence of interest for the genetic transformation of a cell. In general, the heterologous polynucleotide is flanked by at least one, and generally by two AAV inverted terminal repeat sequences (ITRs). The term rAAV vector encompasses both rAAV vector particles and rAAV vector plasmids.

An "AAV virus" or "AAV viral particle" or "rAAV vector particle" or "rAAV virion" refers to a viral particle composed of at least one AAV capsid protein (typically by all of the capsid proteins of a wild-type AAV) and an encapsidated polynucleotide rAAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV virion". Thus, production of rAAV virion necessarily includes production of an rAAV vector, as such a vector is contained within an rAAV virion.

"Packaging" refers to a series of intracellular events that result in the assembly and encapsidation of an AAV particle.

AAV "rep" and "cap" genes refer to polynucleotide sequences encoding replication and encapsidation proteins of adeno-associated virus. AAV rep and cap are referred to herein as AAV "packaging genes."

A "helper virus" for AAV refers to a virus that allows AAV (e.g. wild-type AAV) to be replicated and packaged by a mammalian cell. A variety of such helper viruses for AAV are known in the art, including adenoviruses, herpesviruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

"Helper virus function(s)" refers to function(s) encoded in a helper virus genome which allow AAV replication and packaging (in conjunction with other requirements for replication and packaging described herein). As described herein, "helper virus function" may be provided in a number of ways, including by providing helper virus or providing, for example, polynucleotide sequences encoding the requisite function(s) to a producer cell in trans.

An "infectious" virus or viral particle is one that comprises a polynucleotide component which it is capable of delivering into a cell for which the viral species is tropic. The term does not necessarily imply any replication capacity of the virus. As used herein, an "infectious" virus or viral particle is one that can access a target cell, can infect a target cell, and can express a heterologous nucleic acid in a target cell. Thus, "infectivity" refers to the ability of a viral particle to access a target cell, infect a target cell, and express a heterologous nucleic acid in a target cell. Infectivity can refer to in vitro infectivity or in vivo infectivity. Assays for counting infectious viral particles are described elsewhere in this disclosure and in the art. Viral infectivity can be expressed as the ratio of infectious viral particles to total viral particles. Total viral particles can be expressed as the number of viral genome copies. The ability of a viral particle to express a heterologous nucleic acid in a cell can be referred to as "transduction." The ability of a viral particle to express a heterologous nucleic acid in a cell can be assayed using a number of techniques, including assessment of a marker gene, such as a green fluorescent protein (GFP) assay (e.g., where the virus comprises a nucleotide sequence encoding GFP), where GFP is produced in a cell infected with the viral particle and is detected and/or measured; or the measurement of a produced protein, for example by an enzyme-linked immunosorbent assay (ELISA).

A "replication-competent" virus (e.g. a replication-competent AAV) refers to a phenotypically wild-type virus that is infectious, and is also capable of being replicated in an infected cell (i.e. in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per $10^2$ rAAV particles, less than about 1 rcAAV per $10^4$ rAAV particles, less than about 1 rcAAV per $10^8$ rAAV particles, less than about 1 rcAAV per $10^{12}$ rAAV particles, or no rcAAV).

A "library" of rAAV virions is a composition containing a plurality of rAAV virions representing two or more varieties of rAAV virions that differ among each other in structure (e.g., structure of the AAV capsid protein) and/or sequence of the nucleic acids contained therein.

The term "tropism" refers to a viral particle having higher infectivity for one cell type compared to one or more other cell types. Tropism may also refer to the tissue specificity of the viral particle. For instance, a viral particle that has tropism for muscle cells has a higher infectivity for muscle cells compared to the infectivity for non-muscle cells. In AAV, tropism is affected by the AAV capsid serotype, i.e., the AAV capsid protein amino acid sequence. In contrast, a viral particle is said to be promiscuous when the viral particle exhibits infectivity for a broad range of cell types. In some cases, a viral particle exhibits tropism for one or more cell types, and may also be promiscuous.

"Recombinant," as applied to a polynucleotide means that the polynucleotide is the product of various combinations of cloning, restriction or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

"Operatively linked" or "operably linked" refers to a juxtaposition of genetic elements, wherein the elements are in a relationship permitting them to operate in the expected manner. For instance, a promoter is operatively linked to a coding region if the promoter helps initiate transcription of the coding sequence. There may be intervening residues between the promoter and coding region so long as this functional relationship is maintained.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Heterologous" means derived from a genotypically distinct entity from that of the rest of the entity to which it is being compared. For example, a polynucleotide introduced by genetic engineering techniques into a plasmid or vector derived from a different species is a heterologous polynucleotide. A promoter removed from its native coding sequence and operatively linked to a coding sequence with which it is not naturally found linked is a heterologous promoter. Thus, for example, an rAAV that includes a heterologous nucleic acid encoding a heterologous gene product is an rAAV that includes a nucleic acid not normally included in a naturally-occurring, wild-type AAV, and the encoded heterologous gene product is a gene product not normally encoded by a naturally-occurring, wild-type AAV.

The terms "genetic alteration" and "genetic modification" (and grammatical variants thereof), are used interchangeably herein to refer to a process wherein a genetic element (e.g., a polynucleotide) is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Generally, the genetic element is introduced into a chromosome or mini-chromosome in the cell; but any alteration that changes the phenotype and/or genotype of the cell and its progeny is included in this term.

A cell is said to be "stably" altered, transduced, genetically modified, or transformed with a genetic sequence if the sequence is available to perform its function during extended culture of the cell in vitro. Generally, such a cell is "heritably" altered (genetically modified) in that a genetic alteration is introduced which is also inheritable by progeny of the altered cell.

An "isolated" plasmid, nucleic acid, vector, virus, virion, host cell, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more isolated. An isolated plasmid, nucleic acid, vector, virus, host cell, or other substance is in some embodiments purified, e.g., from about 80% to about 90% pure, at least about 90% pure, at least about 95% pure, at least about 98% pure, or at least about 99%, or more, pure.

The term "ancestral" refers to one or more amino acid sequences that are inferred from orthologous sequences and are likely to represent sequences from which the orthologous sequences descended. In some cases, the orthologous sequences are wild type sequences found in members of the family in nature. The identity of the amino acid at some residues along an ancestral sequence often cannot be inferred above a threshold level of confidence (e.g., above 90%). Thus, the identity of the amino acid of an ancestral sequence is typically determined for 90% to 99%, e.g., 92% to 98%, 93% to 97%, or 94% to 96% of the residues, while the identity of the amino acid at residues that cannot be inferred above a threshold confidence level will be variable. Thus, an ancestral amino acid sequence may be a collection of two or more sequences that differ from one another at certain residues, e.g., differ from one another at up to about 5% of the residues.

The term "genome editing" refers to a process by which a genetic sequence within a cell is altered by inserting, replacing or removing sequences using heterologous nucleases. The heterologous nuclease may be a genetically engineered nuclease, including members of zinc finger nucleases, transcription activator-like effector nucleases (TALENs), Cas9/guide RNA (gRNA) system, or engineered meganucleases.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a rAAV virion" includes a plurality of such rAAV virions and reference to "the isolated nucleic acid" includes reference to one or more isolated nucleic acids and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

Recombinant adeno-associated virus (rAAV) virions comprising a variant AAV capsid protein, e.g., an AAV capsid protein derived from an ancestral AAV capsid protein amino acid sequence, are provided. In certain embodiments the rAAV virions comprising the variant AAV capsid protein exhibit greater infectivity of target cells, such as muscle cells and glial cells. Also provided herein are methods of delivering a gene product to a target cell in an individual by administering to the individual rAAV virions with the variant AAV capsid protein. The present disclosure further provides methods of generating rAAV virions that have a variant AAV capsid protein derived from an ancestral AAV capsid protein amino acid sequence.

Recombinant Adeno-Associated Virus Virions

The present disclosure provides rAAV virions comprising a variant AAV capsid protein, e.g., an AAV capsid protein derived from an ancestral AAV capsid protein amino acid sequence.

AAV Virions Comprising an Ancestral AAV Capsid Protein

Aspects of the present disclosure include an rAAV virion that contains an ancestral AAV capsid protein. In certain embodiments, the amino acid sequence of the ancestral AAV capsid protein is inferred from the amino acid sequence of AAV capsid protein from wild type AAV serotypes from different host species, such as human, macaque, rhesus monkey, etc. Any suitable method may be used to infer the ancestral AAV capsid protein amino acid sequence, such as methods further described below.

In certain embodiments, the ancestral AAV capsid protein has at least 94%, e.g., at least 95%, e.g., at least 96%, at least 97%, at least 98%, at least 99%, or 100% amino acid sequence identity to the sequence set forth in SEQ ID NO: 7. In certain embodiments, the ancestral AAV capsid protein is identical to the sequence set forth in SEQ ID NO: 7 at all positions except for the amino acid residues at positions 264, 266, 268, 448, 459, 460, 470, 471, 474, 495, 516, 533, 547, 551, 555, 557, 561, 563, 577, 583, 593, 596, 661, 662, 664, 665, 710, 717, 718, 719 and 723 of SEQ ID NO: 7.

Certain aspects of the present disclosure include a composition containing a plurality of rAAV virions, e.g., an ancestral AAV library, wherein each rAAV virion includes an ancestral AAV capsid protein having at least 94%, e.g., at least 95%, e.g., at least 96%, at least 97%, at least 98%, at least 99%, or 100% amino acid sequence identity to the sequence set forth in SEQ ID NO: 7. Thus, in certain embodiments, the ancestral library contains a plurality of ancestral AAV capsid proteins having at least 94%, e.g., at least 95%, e.g., at least 96%, at least 97%, at least 98%, at least 99%, or 100% amino acid sequence identity to the sequence set forth in SEQ ID NO: 7. In certain embodiments, the amino acid at residues 264, 266, 268, 448, 459, 460, 470, 471, 474, 495, 516, 533, 547, 551, 555, 557, 561, 563, 577, 583, 593, 596, 661, 662, 664, 665, 710, 717, 718, 719 and 723 of the plurality of ancestral AAV capsid proteins in the ancestral library varies between different ancestral AAV libraries. In some embodiments, the ancestral library is synthetically made such that the distribution of types of amino acid present at these residues reflects a theoretical distribution inferred from the amino acid sequences of AAV capsid proteins from wild type AAV serotypes. Thus, in such embodiments, the frequency of the most common amino acid present at each of the variable residues in the ancestral AAV capsid protein amino acid sequence differs on average from the frequency in the inferred theoretical distribution by a range of −10% to 10%, e.g., −6% to 6%, including −4% to 4% of the time. In some embodiments, the distribution of types of amino acid present at these residues is the distribution in a library of rAAV virions obtained by packaging an ancestral library, transfecting the packaged library into a host cell, and recovering the replicated viruses. In some embodiments, the distribution of types of amino acid present at these residues is the distribution in a library of rAAV virions obtained after one or more rounds of selection in a target cell, as described further below. In certain embodiments, the target cell is a muscle cell line (C2C12), a lung epithelial cell line (IB3-1), glioblastoma cells, melanoma cell line (B16) or a human embryonic kidney 293T cell line. Exemplary distribution of types of amino acid present at these residues is shown in the table shown in FIG. 3.

In certain embodiments, an ancestral AAV library containing a plurality of rAAV virions that contains an ancestral AAV capsid protein, as described above, exhibits increased infectivity of a target cell compared to the infectivity of an AAV virion with a wild type AAV serotype capsid protein.

In certain embodiments, an ancestral AAV library containing a plurality of rAAV virions with an ancestral AAV capsid protein exhibits altered dependency on target cell receptors for infectivity compared to the dependency of an AAV virion with a wild type AAV serotype capsid protein (e.g., wild type AAV1 or AAV2 capsid protein). Dependency on target cell receptors may be determined, e.g., by comparing the transduction efficiency of a virion for a parental cell line with a target cell receptor of interest with the transduction efficiency for a derived cell line that lacks the target cell receptor. Thus, if the transduction efficiency of a virion for the derived cell line is not reduced compared to the parental cell line, the virion does not exhibit dependency on the target cell receptor for infectivity.

Thus, in certain embodiments, an ancestral AAV library containing a plurality of rAAV virions that contains an ancestral AAV capsid protein exhibits 50% or more, e.g., 60% or more, 70% or more, 80% or more, 90% or more, or 95% or more reduced dependency on a target cell receptor for infectivity compared to an AAV virion with a wild type AAV serotype capsid protein. In certain embodiments, the ancestral AAV library exhibits 50% or more, e.g., 60% or more, 70% or more, 80% or more, 90% or more, or 95% or more reduced dependency on heparin sulfate proteoglycans for infectivity compared to an AAV virion with a wild type AAV serotype capsid protein (e.g., wild type AAV2 capsid protein). In certain embodiments, the ancestral AAV library exhibits 50% or more, e.g., 60% or more, 70% or more, 80% or more, 90% or more, or 95% or more reduced dependency on sialic acids for infectivity compared to an AAV virion with a wild type AAV serotype capsid protein (e.g., wild type AAV1 capsid protein).

In certain embodiments, an ancestral AAV library containing a plurality of rAAV virions with an ancestral AAV capsid protein exhibits promiscuity for target cell infectivity. In certain embodiments, the ancestral AAV library exhibits infectivity at least above background for each of a plurality of target cell types. Such ancestral AAV libraries showing promiscuous infectivity for plurality of target cell types may be suitable for deriving variant rAAV virions that have tropism for a specific cell type, including a non-permissive cell type, through directed evolution, as described further below.

In certain embodiments, an ancestral AAV library containing a plurality of rAAV virions with an ancestral AAV capsid protein has a higher mutational tolerance and/or evolvability compared to the mutational tolerance and/or evolvability of an AAV virion with a wild type AAV serotype capsid protein. Mutational tolerance may be reflected in the resistance of the virions to heat treatment, measured as the ability of virions to retain at least 10%, e.g., at least 20%, or at least 30% infectivity of a target cell after being exposed transiently (e.g., 10 minutes) to high temperature compared to virions that have not been exposed to high temperature. Without being held to theory, AAV virions with increased thermostability may be more tolerant to mutations that disrupt overall capsid stability. Thus, rAAV virions of the ancestral AAV library are resistant to transient exposure (e.g., 10 minute-exposure) to temperature in the range of 75 to 79° C., e.g., 76 to 78° C., 76.5 to 78° C., including 77 to 78° C. In some instances, the temperature to which rAAV virions of the ancestral AAV library are transiently exposed (e.g., 10 minute) and at which infectivity is reduced to 50% compared to virions that are not exposed to high temperature is higher by a range of 2 to 20° C., e.g., 2 to 15° C., 3 to 10° C., including 3 to 5° C., compared to an AAV virion comprising a wild type AAV serotype capsid protein.

AAV Virion Comprising a Variant AAV Capsid Protein

Further aspects of the present disclosure include an rAAV virion that includes a variant AAV capsid protein derived from an ancestral AAV capsid protein, as described above. In certain embodiments, the rAAV virion includes a) a variant AAV capsid protein, wherein the variant AAV capsid protein contains an amino acid sequence having at least 95%, e.g., at least 96%, at least 97%, at least 97.5%, at least 98%, at least 98.5%, at least 99%, at least 99.5%, or 100% amino acid sequence identity to the sequence set forth in SEQ ID NO: 16, wherein the amino acids at positions 264, 448, 459, 470, 495, 533, 547, 555, 557, 561, 563, 593, 596, 661, 662, 664, 718 and 723 are A, A, N, S, S, D, E, A, E, L, N, A, A, A, T, T, N and S, respectively; Q, S, N, A, S, E, Q, T, D, M, S, Q, T, A, V, S, S and S, respectively; or A, A, T, S, T, D, Q, A, D, I, N, A, T, T, V, S, S and T, respectively, and b) a heterologous nucleic acid containing a nucleotide sequence encoding a gene product. In certain embodiments, the variant AAV capsid protein confers increased infectivity of a target cell. In certain embodiments, the variant AAV capsid protein confers altered dependency on target cell receptors for infectivity compared to the dependency of an AAV virion with a wild type AAV serotype capsid protein.

Thus, an aspect of the present disclosure includes an rAAV virion that includes a) a variant AAV capsid protein, wherein the variant AAV capsid protein comprises an amino acid sequence having at least 95%, e.g., at least 96%, at least 97%, at least 97.5%, at least 98%, at least 98.5%, at least 99%, at least 99.5%, or 100% amino acid sequence identity to the sequence set forth in SEQ ID NO: 13, and b) a heterologous nucleic acid containing a nucleotide sequence encoding a gene product. In certain embodiments, the variant AAV capsid protein confers increased infectivity of a target cell. In certain embodiments, the variant AAV capsid protein confers altered dependency on target cell receptors for infectivity compared to the dependency of an AAV virion with a wild type AAV serotype capsid protein.

Another aspect of the present disclosure includes an rAAV virion that includes a) a variant AAV capsid protein, wherein the variant AAV capsid protein comprises an amino acid sequence having at least 95%, e.g., at least 96%, at least 97%, at least 97.5%, at least 98%, at least 98.5%, at least 99%, at least 99.5%, or 100% amino acid sequence identity to the sequence set forth in SEQ ID NO: 14, and b) a heterologous nucleic acid containing a nucleotide sequence encoding a gene product. In certain embodiments, the variant AAV capsid protein confers increased infectivity of a target cell. In certain embodiments, the variant AAV capsid protein confers altered dependency on target cell receptors for infectivity compared to the dependency of an AAV virion with a wild type AAV serotype capsid protein.

A further aspect of the present disclosure includes an rAAV virion that includes a) a variant AAV capsid protein, wherein the variant AAV capsid protein comprises an amino acid sequence having at least 95%, e.g., at least 96%, at least 97%, at least 97.5%, at least 98%, at least 98.5%, at least 99%, at least 99.5%, or 100% amino acid sequence identity to the sequence set forth in SEQ ID NO: 15, and b) a heterologous nucleic acid containing a nucleotide sequence encoding a gene product. In certain embodiments, the variant AAV capsid protein confers increased infectivity of a target cell. In certain embodiments, the variant AAV capsid protein confers altered dependency on target cell receptors for infectivity compared to the dependency of an AAV virion with a wild type AAV serotype capsid protein.

In certain embodiments, the target cell is a cell in a tissue in vivo, a cell in a tissue slice, dissociated primary cells in culture, a cell line, including an immortalized cell line, etc. In some embodiments, the target cell is a healthy cell, e.g., a cell in or obtained from a healthy tissue. In some cases, the target cell is a pathological cell, e.g., a cell in or obtained from a diseased tissues or an individual diagnosed with a disease. In certain embodiments, the target cell is a lung epithelial cell line (such as, but not limited to, IB3-1 cells); a human embryonic kidney cell line (e.g., HEK293T cells); a mouse myoblast cell line (e.g., C2C12 cells); a skin melanoma cell line (e.g., B16-F10 cells); and may include CHO cells. Other cell lines suitable as target cells may be readily obtained from, e.g., the American Type Culture Collection (ATCC). In some instances, the target cell is a primary tumor cell (e.g., glioblastoma cells). In some instances, the target cell is a cell in muscle, such as skeletal muscle or cardiac muscle; in nervous tissue, such as the central nervous system (brain, spinal cord, retina), or the peripheral nervous system; in the skin (epidermis, dermis, etc.); in the immune system (bone marrow, spleen, thymus, lymph nodes, blood, etc.); and the like. In certain embodiments, the target cell is a glial cell (astrocyte, oligodendrocyte, radial glia, glioblastoma, etc.), a neuron, a muscle cell, a keratinocyte, an epithelial cell, an endothelial cell, a hepatocyte, a chondrocyte, an osteocyte, a T-lymphocyte, a B-lymphocyte, a macrophage, a dendritic cell, an eosinophil, a basophil, etc. A glial cell, as used herein, is meant to include a healthy or a pathological glial cell, in vitro or in vivo. Thus, a target glial cell may be a healthy glial cell or a glioblastoma cell. In some embodiments, the healthy glial cell or glioblastoma cell is in an individual, e.g. a glioblastoma cell in a patient with glioma.

In some cases, an rAAV virion of the present disclosure that comprises a variant AAV capsid protein exhibits at least 5-fold, at least 10-fold, at least 15-fold, at least 20-fold, at least 25-fold, at least 50-fold, or more than 50-fold, increased infectivity of a target cell compared to the infectivity of the target cell by an AAV virion with a wild type AAV capsid protein (e.g., wild type AAV1 capsid protein). Infectivity of a target cell may be determined by detecting a detectable marker protein encoded by and expressed from a nucleic acid carried by the rAAV virion. For instance, the rAAV virion may comprise a nucleic acid encoding a luciferase, and infectivity of a target cell may be determined by measuring luciferase activity from the target cell. In such cases, a higher luciferase activity measured from target cells infected with the variant rAAV virion compared to the luciferase activity measured from target cells infected with a wild type rAAV virion indicates that the variant rAAV virion has higher infectivity than the wild type rAAV virion. Other suitable detectable marker proteins include, but are not limited to, fluorescent proteins such as a green fluorescent protein, a yellow fluorescent protein, a red fluorescent protein, a cyan fluorescent protein, etc.

Thus, in certain embodiments, a subject rAAV virion comprising a variant AAV capsid protein exhibits at least 5-fold, at least 10-fold, at least 15-fold, at least 20-fold, at least 25-fold, at least 50-fold, or more than 50-fold, increased infectivity of a muscle cell compared to the infectivity of the muscle cell by an AAV virion with a wild type AAV capsid protein (e.g., wild type AAV1 capsid protein). In certain embodiments, the rAAV virion exhibits at least 5-fold, at least 10-fold, at least 15-fold, at least 20-fold, at least 25-fold, at least 50-fold, or more than 50-fold, increased infectivity of a glial or glioblastoma cell compared to the infectivity of the muscle cell by an AAV virion with a wild type AAV capsid protein (e.g., wild type AAV1 capsid protein).

A subject rAAV virion with a variant AAV capsid protein exhibits altered dependency on target cell receptors for infectivity compared to an AAV virion with a wild type AAV serotype capsid protein (e.g., wild type AAV1 or AAV2 capsid protein). In certain embodiments, the virion exhibits 50% or more, e.g., 60% or more, 70% or more, 80% or more, 90% or more, or 95% or more reduced dependency on a target cell receptor for infectivity compared to an AAV virion with a wild type AAV serotype capsid protein. In certain embodiments, the virion exhibits 50% or more, e.g., 60% or more, 70% or more, 80% or more, 90% or more, or 95% or more reduced dependency on heparin sulfate proteoglycans for infectivity compared to an AAV virion with a wild type AAV serotype capsid protein (e.g., wild type AAV2 capsid protein). In certain embodiments, the virion exhibits 50% or more, e.g., 60% or more, 70% or more, 80% or more, 90% or more, or 95% or more reduced dependency on sialic acids for infectivity compared to an AAV virion with a wild type AAV serotype capsid protein (e.g., wild type AAV1 capsid protein).

Gene Products

The gene product encoded by a nucleotide sequence in a heterologous nucleic acid of the subject rAAV virion may be any suitable gene product, such as, but not limited to a polypeptide, a nucleic acid, or a genome editing gene product.

Polypeptide gene products may include any suitable polypeptide, such as, but not limited to, troponin, laminins, collagens, lamin, selenoprotein N, protein-O-mannosyltransferase, fukutin, LARGE, O-linked mannose β1,2-N-acetylglucosaminyl-transferase, and isoprenoid synthase domain-containing protein. In some embodiments, the polypeptide gene product is a secreted polypeptide. In some embodiments, the secreted polypeptide is a therapeutic protein. Suitable secreted polypeptides include, but are not limited to, lipoprotein lipase, factor IX, $\alpha_1$-antitrypsin, follistatin, soluble myostatin receptor, apelin, glucagon-like peptide 1, insulin-like growth factor 1, alpha-galactosidase, iduronidase, iduronate-2-sulfatase, alpha-glucosidase, and N-acetylgalactosamine 4-sulfatase.

Lipoprotein lipase (LPL) is a lipid metabolism enzyme involved in triglyceride hydrolysis. LPL-deficiency is implicated in hypertriglyceridemia. Suitable LPL amino acid sequences encoded by the subject heterologous nucleic acid include human LPL (Gene ID: 4023), mouse LPL (Gene ID: 16956), rat LPL (Gene ID: 24539), non-human primate LPL (Gene ID: 464031), chicken LPL (Gene ID: 396219), dog LPL (Gene ID: 403626), cat LPL (Gene ID: 727696), etc.

Factor IX (coagulation factor IX) is a serine protease that plays a role in blood coagulation. Factor IX-deficiency causes hemophilia B. Suitable factor IX amino acid sequences encoded by the subject heterologous nucleic acid include human factor IX (Gene ID: 2158), mouse factor IX (Gene ID: 14071), rat factor IX (Gene ID: 24946), non-human primate factor IX (Gene ID: 465887), chicken factor IX (Gene ID: 374258), dog factor IX (Gene ID: 404015), cat factor IX (Gene ID: 493973), etc.

$\alpha_1$-antitrypsin is a protease inhibitor that plays a role in inflammation. $\alpha_1$-antitrypsin-deficiency is implicated in pulmonary emphysema and other symptoms of chronic tissue breakdown. Suitable $\alpha_1$-antitrypsin amino acid sequences encoded by the subject heterologous nucleic acid include human $\alpha_1$-antitrypsin (Gene ID: 5265), mouse $\alpha_1$-antitrypsin (Gene ID: 20700), rat $\alpha_1$-antitrypsin (Gene ID: 24648), non-human primate $\alpha_1$-antitrypsin (Gene ID: 467541), chicken $\alpha_1$-antitrypsin (Gene ID: 423434), dog $\alpha_1$-antitrypsin (Gene ID: 480422), cat $\alpha_1$-antitrypsin (Gene ID: 101098107), etc.

Alpha-galactosidase is an enzyme that hydrolyzes alpha-galactosyl moieties from glycolipids and glycoproteins. Alpha-galactosidase deficiencies are implicated in Fabry's disease, which may be treated by recombinantly produced alpha-galactosidase (agalsidase alfa or agalsidase beta). Suitable alpha-galactosidase amino acid sequences encoded by the subject heterologous nucleic acid include human alpha-galactosidase (GeneID: 2717), mouse alpha-galactosidase (GeneID: 11605), rat alpha-galactosidase (GeneID: 363494), non-human primate alpha-galactosidase (GeneID: 465761), chicken alpha-galactosidase (GeneID: 422188), dog alpha-galactosidase (GeneID: 480988), cat alpha-galactosidase (GeneID: 101091428), etc.

Iduronidase is an enzyme that catalyzes the hydrolysis of unsulfated alpha-L-iduronosidic bonds in dermatan sulfate, a glycosaminoglycan found in skin, blood vessels, heart valves, tendons and the lungs. Recombinantly produced iduronidase is known as laronidase. sIduronidase deficiencies are implicated in mucopolysaccharidoses (MPS), type I (MPS-I, also known as Hurler-Scheie syndrome). Suitable iduronidase amino acid sequences encoded by the subject heterologous nucleic acid include human iduronidase (GeneID: 3425), mouse iduronidase (GeneID: 15932), rat iduronidase (GeneID: 360904), non-human primate iduronidase (GeneID: 461056), chicken iduronidase (GeneID: 427294), dog iduronidase (GeneID: 100505382), cat iduronidase (GeneID: 101095896), etc.

Iduronate-2-sulfatase is a sulfatase enzyme required for lysosomal degradation for heparin sulfate and dermatan sulfate. Deleterious mutations in iduronate-2-sulfatase is associated with MPS-II (also known as Hunter syndrome). Iduronate-2-sulfatase is recombinantly produced as idursulphase for use in therapy. Suitable iduronate-2-sulfatase amino acid sequences encoded by the subject heterologous nucleic acid include human iduronate-2-sulfatase (GeneID: 3423), mouse iduronate-2-sulfatase (GeneID: 15931), rat iduronate-2-sulfatase (GeneID: 363513), non-human primate iduronate-2-sulfatase (GeneID: 465896), chicken iduronate-2-sulfatase (GeneID: 422392), dog iduronate-2-sulfatase (GeneID: 492194), cat iduronate-2-sulfatase (GeneID: 101081450), etc.

Alpha-glucosidase is a starch hydrolyzing enzyme and deficiencies in the enzyme are implicated in glycogen storage disease type II (also known as Pompe disease). An alpha-glucosidase analog is produced recombinantly for therapeutic use and is known as alglucosidase alfa. Suitable iduronidase amino acid sequences encoded by the subject heterologous nucleic acid include human alpha-glucosidase (GeneID: 2548), mouse alpha-glucosidase (GeneID: 14387), rat alpha-glucosidase (GeneID: 367562), non-human primate alpha-glucosidase (GeneID: 454940), chicken alpha-glucosidase (GeneID: 416462), dog alpha-glucosidase (GeneID: 483352), cat alpha-glucosidase (GeneID: 101086359), etc.

N-acetylgalactosamine 4-sulfatase is an enzyme that catalyzes the hydrolysis of the 4-sulfate groups of the N-acetyl-D-galactosamine 4-sulfate units of chondroitin sulfate and dermatan sulfate. N-acetylgalactosamine 4-sulfatase deficiencies are implicated in MPS IV (also known as Maroteaux-Lamy syndrome). N-acetylgalactosamine 4-sulfatase is recombinantly produced as galsulfase for use in therapy. Suitable N-acetylgalactosamine 4-sulfatase amino acid sequences encoded by the subject heterologous nucleic acid include human N-acetylgalactosamine 4-sulfatase (GeneID: 411), mouse N-acetylgalactosamine 4-sulfatase (GeneID: 11881), rat N-acetylgalactosamine 4-sulfatase (GeneID: 25227), non-human primate N-acetylgalactosamine 4-sulfatase (GeneID: 737316), chicken N-acetylgalactosamine 4-sulfatase (GeneID: 771459), dog N-acetylgalactosamine 4-sulfatase (GeneID: 610364), cat N-acetylgalactosamine 4-sulfatase (GeneID: 100216331), etc.

In certain embodiments, the secreted polypeptide can be fused to an immunoglobulin Fc region (e.g., human Fc) to form a fusion conjugate (or fusion molecule). Fc fusion conjugates are known to increase the production or systemic half-life of secreted proteins. In certain embodiments, the amino acid sequence of the secreted proteins may be modified to replace the endogenous signal peptide with a heterologous signal peptide that enhances secretion of the polypeptide from the target cell. Suitable signal peptides are described in, e.g., Sun et al., Mol Ther. 2006 14: 822; and U.S. Application Pub. Nos. 20070142623, 20040115775, which are incorporated by reference herein.

Troponins (troponin C, troponin I, troponin T) are regulatory proteins involved in skeletal and cardiac muscle contraction. Deficiencies in troponins are implicated in familial hypertrophic cardiomyopathy. Suitable troponin amino acid sequences encoded by the subject heterologous nucleic acid include human troponins (Gene IDs: 7134, 7137, 7139), mouse troponins (Gene IDs: 21954, 21956, 21957), rat $\alpha_1$-troponins (Gene IDs: 24838, 24837, 29248), non-human primate $\alpha_1$-troponins (Gene IDs: 466317, 457618, 746369), etc.

Herpes simplex virus type 1 thymidine kinase (HSV-1 Tk) is an enzyme that finds use in treatment of cancer, such as glioma. Without being held to theory, a cell expressing HSV-1 Tk can convert thymidine kinase substrate analogs, such as ganciclovir (GCV) into metabolites that are highly toxic to dividing cells, such as tumor cells. Suitable HSV-1 Tk amino acid sequences encoded by the subject heterologous nucleic acid include Human HSV-1 Tk (Gene ID: 2703374), Human HSV-2 Tk (Gene ID: 1487307), etc.

Other exemplary polypeptide gene products that find use in the present disclosure are described in, e.g., U.S. Patent Application Pub. No. 2006/0276376, which is incorporated by reference.

A genome editing gene product may include zinc finger nucleases, transcription activator-like effector nucleases (TALENs), and Cas9/gRNA system, or a component thereof, where the genome editing gene product is a multi-component gene product.

Zinc-finger nucleases (ZFNs) are artificial DNA endonucleases generated by fusing a zinc finger DNA binding domain to a DNA cleavage domain. ZFNs can be engineered to target desired DNA sequences and this enables zinc-finger nucleases to cleave unique target sequences. When introduced into a cell, ZFNs can be used to edit target DNA in the cell (e.g., the cell's genome) by inducing double strand breaks. For more information on the use of ZFNs, see, for example: Asuri et al., Mol Ther. 2012 February;20(2):329-38; Bibikova et al. Science. 2003 May 2;300(5620):764; Wood et al. Science. 2011 Jul. 15;333(6040):307; Ochiai et al. Genes Cells. 2010 August;15(8):875-85; Takasu et. al., Insect Biochem Mol Biol. 2010 October;40(10):759-65; Ekker et al, Zebrafish 2008 Summer;5(2): 121-3; Young et al, Proc Natl Acad Sci USA. 2011 Apr. 26;108(17):7052-7; Goldberg et al, Cell. 2010 Mar. 5;140(5):678-91; Geurts et al, Science. 2009 Jul. 24;325(5939):433; Flisikowska et al, PLoS One. 2011;6(6):e21045. doi: 10.1371/journal-.pone.0021045. Epub 2011 Jun. 13; Hauschild et al, Proc Natl Acad Sci USA. 2011 Jul. 19;108(29): 12013-7; and Yu et al, Cell Res. 2011 November;21(1 1): 1638-40; all of which are herein incorporated by reference for their teachings related to ZFNs. The term "ZFN agent" encompasses a zinc finger nuclease and/or a polynucleotide comprising a nucleotide sequence encoding a zinc finger nuclease.

Transcription activator-like effector nucleases (TALENs) are artificial DNA endonucleases generated by fusing a TAL (Transcription activator-like) effector DNA binding domain to a DNA cleavage domain. TALENS can be quickly engineered to bind practically any desired DNA sequence and when introduced into a cell, TALENs can be used to edit target DNA in the cell (e.g., the cell's genome) by inducing double strand breaks. For more information on the use of TALENs, see, for example: Hockemeyer et al. Nat Biotechnol. 2011 Jul. 7;29(8):731-4; Wood et al. Science. 2011 Jul. 15;333(6040):307; Tesson et al. Nat Biotechnol. 2011 Aug. 5;29(8):695-6; and Huang et. al., Nat Biotechnol. 2011 Aug. 5;29(8):699-700; all of which are herein incorporated by reference for their teachings related to TALENs. The term "TALEN agent" encompasses a TALEN and/or a polynucleotide comprising a nucleotide sequence encoding a TALEN.

Cas 9 is a clustered regularly interspaced short palindromic repeats (CRISPR)-associated (Cas) protein (or functional equivalent and/or variant thereof, e.g., a Cas9-like protein) that contains DNA endonuclease activity that depends on association of the protein with two naturally occurring or synthetic RNA molecules called crRNA and tracrRNA (also called guide RNAs (gRNAs)). In some cases, the two molecules are covalently linked to form a single molecule (also called a single guide RNA ("sgRNA")). Thus, the Cas9 or Cas9-like protein associates with a DNA-targeting RNA (which term encompasses both the two-molecule guide RNA configuration and the single-molecule guide RNA configuration), which activates the Cas9 or Cas9-like protein and guides the protein to a target nucleic acid sequence. If the Cas9 or Cas9-like protein retains its natural enzymatic function, it will cleave target DNA to create a double-strand break, which can lead to genome alteration (i.e., editing: deletion, insertion (when a donor polynucleotide is present), replacement, etc.), thereby altering gene expression. Some variants of Cas9 (which variants are encompassed by the term Cas9-like) have been altered such that they have a decreased DNA cleaving activity (in some cases, they cleave a single strand instead of both strands of the target DNA, while in other cases, they have severely reduced to no DNA cleavage activity). Cas9-like proteins with decreased DNA-cleavage activity (even no DNA-cleaving activity) can still be guided to a target DNA and can block RNA polymerase activity. Thus enzymatically inactive Cas9-like proteins can be targeted to a specific location in a target DNA by a DNA-targeting RNA in order to block transcription of the target DNA.

Detailed information regarding Cas 9/gRNA systems can be found, for example in (a) Jinek et. al., Science. 2012 Aug. 17;337(6096):816-21: "A programmable dual-RNA-guided DNA endonuclease in adaptive bacterial immunity"; (b) Qi et al., Cell. 2013 Feb. 28; 152(5): 1173-83: "Repurposing CRISPR as an RNA-guided platform for sequence-specific control of gene expression", and (c) WO 2013/176772; each of which is hereby incorporated by reference in its entirety. Thus, the term "CRISPR agent" as used herein encompasses any agent (or nucleic acid encoding such an agent), comprising naturally occurring and/or synthetic sequences, that can be used in the Cas9-based system (e.g., a Cas9 or Cas9-like protein; any component of a DNA-targeting RNA, e.g., a crRNA-like RNA, a tracrRNA-like RNA, a single guide RNA, etc.; a donor polynucleotide; and the like).

Suitable nucleic acid gene products include interfering RNA, antisense RNA, ribozymes, and aptamers. Where the gene product is an interfering RNA (RNAi), suitable RNAi include RNAi that decrease the level of a disease-related protein in a cell. For example, an RNAi can be a miRNA, an shRNA, or an siRNA that reduces the level of, e.g., FRG1 in a muscle cell, or $O^6$-methylguanine-DNA methyltransferase (MGMT) in a glioblastoma cell. Suitable targets for a nucleic acid gene product are described in, e.g., Bortolanza et al., Mol Ther. 2011 19:2055; U.S. Patent Publication Nos. 2013/0347136, 2009/0087434, 2011/0059114, 2011/0165227; PCT Publication Nos. WO2006/128063, WO2011/134023.

Control Elements

As noted above, an rAAV virion of the present disclosure includes an rAAV vector comprising a heterologous nucleic acid comprising a nucleotide sequence encoding a gene product. The heterologous nucleotide sequence can be operably linked to control elements that direct the transcription or expression thereof in the nucleotide sequence in vivo. Such control elements can comprise control sequences normally associated with the selected gene (e.g., endogenous cellular control elements). Alternatively, heterologous control sequences can be employed. Useful heterologous control sequences generally include those derived from sequences encoding mammalian or viral genes. Examples include, but are not limited to, the SV40 early promoter, mouse mammary tumor virus long terminal repeat (LTR) promoter; adenovirus major late promoter (Ad MLP); a herpes simplex virus (HSV) promoter, an endogenous cellular promoter that is heterologous to the gene of interest, a cytomegalovirus (CMV) promoter such as the CMV immediate early promoter region (CMVIE), a Rous sarcoma virus (RSV) promoter, synthetic promoters, hybrid promoters, and the like. In addition, sequences derived from nonviral genes, such as the murine metallothionein gene, can also be used.

Such promoter sequences are commercially available from, e.g., Stratagene (San Diego, Calif.).

In some embodiments, a cell type-specific or a tissue-specific promoter will be operably linked to the heterologous nucleic acid encoding the heterologous gene product, such that the gene product is produced selectively or preferentially in a particular cell type(s) or tissue(s). In some embodiments, an inducible promoter will be operably linked to the heterologous nucleic acid.

Methods for Generating an rAAV Virion

An AAV expression vector which comprises a heterologous nucleic acid and which is used to generate an rAAV virion, can be constructed using methods that are well known in the art. See, e.g., Koerber et al. (2009) *Mol. Ther.* 17:2088; Koerber et al. (2008) *Mol Ther.*16:1703-1709; U.S. Pat. Nos. 7.439.065, 6,951,758, and 6,491,907. For example, the heterologous sequence(s) can be directly inserted into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Curr. Topics Microbiol. Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

In order to produce rAAV virions, an AAV expression vector is introduced into a suitable host cell using known techniques, such as by transfection. A number of transfection techniques are generally known in the art. See, e.g., Graham et al. (1973) Virology, 52:456, Sambrook et al. (1989) Molecular Cloning, A Laboratory Manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456-467), direct micro-injection into cultured cells (Capecchi, M. R. (1980) Cell 22:479-488), electroporation (Shigekawa et al. (1988) BioTechnigues 6:742-751), liposome mediated gene transfer (Mannino et al. (1988) BioTechniques 6:682-690), lipid-mediated transduction (Felgner et al. (1987) Proc. Natl. Acad. Sci. USA 84:7413-7417), and nucleic acid delivery using high-velocity microprojectiles (Klein et al. (1987) Nature 327:70-73).

Suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used. For example, the human embryonic kidney cell line 293 is a human embryonic kidney cell line that has been transformed with adenovirus type-5 DNA fragments (Graham et al. (1977) J. Gen. Virol. 36:59), and expresses the adenoviral E1a and E1b genes (Aiello et al. (1979) Virology 94:460). The 293 cell line is readily transfected, and provides a convenient platform in which to produce rAAV virions.

Methods of producing an AAV virion in insect cells are known in the art, and can be used to produce a subject rAAV virion. See, e.g., U.S. Patent Publication No. 2009/0203071; U.S. Pat. No. 7,271,002; and Chen (2008) Mol. Ther. 16:924.

Pharmaceutical Compositions

The present disclosure provides a pharmaceutical composition comprising: a) a subject rAAV virion, as described above; and b) a pharmaceutically acceptable carrier, diluent, excipient, or buffer. In some embodiments, the pharmaceutically acceptable carrier, diluent, excipient, or buffer is suitable for use in a human.

Such excipients, carriers, diluents, and buffers include any pharmaceutical agent that can be administered without undue toxicity. Pharmaceutically acceptable excipients include, but are not limited to, liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H.C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

A subject composition can comprise a liquid comprising a subject rAAV virion in solution, in suspension, or both. As used herein, liquid compositions include gels. In some cases, the liquid composition is aqueous. In some embodiments, the composition is an in situ gellable aqueous composition, e.g., an in situ gellable aqueous solution. Aqueous compositions have physiologically compatible pH and osmolality.

Nucleic Acids and Host Cells

Other aspects of the present disclosure include an isolated nucleic acid including a nucleotide sequence that encodes a variant AAV capsid protein, wherein the variant AAV capsid protein comprises an amino acid sequence having at least 95%, e.g., at least 96%, at least 97%, at least 97.5%, at least 98%, at least 98.5%, at least 99%, at least 99.5%, or 100% amino acid sequence identity to the sequence set forth in SEQ ID NO: 16, wherein the amino acids at positions 264, 448, 459, 470, 495, 533, 547, 555, 557, 561, 563, 593, 596, 661, 662, 664, 718 and 723 are A, A, N, S, S, D, E, A, E, L, N, A, A, A, T, T, N and S, respectively; Q, S, N, A, S, E, Q, T, D, M, S, Q, T, A, V, S, S and S, respectively; or A, A, T, S, T, D, Q, A, D, I, N, A, T, T, V, S, S and T, respectively. In certain embodiments, the variant AAV capsid protein confers increased infectivity of a target cell compared to the infectivity of an AAV virion with a wild type AAV serotype capsid protein. In certain embodiments, the variant AAV capsid protein confers altered dependency on target cell receptors for infectivity compared to the dependency of an AAV virion with a wild type AAV serotype capsid protein.

In certain embodiments, the isolated nucleic acid includes a nucleotide sequence that encodes a variant AAV capsid protein, wherein the variant AAV capsid protein comprises an amino acid sequence having at least 95%, e.g., at least 96%, at least 97%, at least 97.5%, at least 98%, at least 98.5%, at least 99%, at least 99.5%, or 100% amino acid sequence identity to the sequence set forth in SEQ ID NO: 13. In certain embodiments, the variant AAV capsid protein confers increased infectivity of a target cell. In certain embodiments, the variant AAV capsid protein confers altered dependency on target cell receptors for infectivity compared to the dependency of an AAV virion with a wild type AAV serotype capsid protein.

In certain embodiments, the isolated nucleic acid includes a nucleotide sequence that encodes a variant AAV capsid protein, wherein the variant AAV capsid protein comprises an amino acid sequence having at least 95%, e.g., at least 96%, at least 97%, at least 97.5%, at least 98%, at least 98.5%, at least 99%, at least 99.5%, or 100% amino acid sequence identity to the sequence set forth in SEQ ID NO: 14. In certain embodiments, the variant AAV capsid protein confers increased infectivity of a target cell. In certain embodiments, the variant AAV capsid protein confers altered dependency on target cell receptors for infectivity compared to the dependency of an AAV virion with a wild type AAV serotype capsid protein.

In certain embodiments, the isolated nucleic acid includes a nucleotide sequence that encodes a variant AAV capsid protein, wherein the variant AAV capsid protein comprises an amino acid sequence having at least 95%, e.g., at least 96%, at least 97%, at least 97.5%, at least 98%, at least 98.5%, at least 99%, at least 99.5%, or 100% amino acid sequence identity to the sequence set forth in SEQ ID NO: 15. In certain embodiments, the variant AAV capsid protein confers increased infectivity of a target cell. In certain embodiments, the variant AAV capsid protein confers altered dependency on target cell receptors for infectivity compared to the dependency of an AAV virion with a wild type AAV serotype capsid protein.

In certain embodiments, the isolated nucleic acid includes a nucleotide sequence that encodes an ancestral AAV capsid protein, wherein the ancestral AAV capsid protein comprises an amino acid sequence having at least 94%, e.g., at least 95%, e.g., at least 96%, at least 97%, at least 98%, at least 99%, or 100% amino acid sequence identity to the sequence set forth in SEQ ID NO: 7. In certain embodiments, the ancestral AAV capsid protein confers increased infectivity of a target cell compared to the infectivity of an AAV virion with a wild type AAV serotype capsid protein. In certain embodiments, the ancestral AAV capsid protein confers altered dependency on target cell receptors for infectivity compared to the dependency of an AAV virion with a wild type AAV serotype capsid protein.

The present invention further provides host cells, e.g., isolated (genetically modified) host cells, comprising a subject nucleic acid. A subject host cell can be an isolated cell, e.g., a cell in in vitro culture. A subject host cell is useful for producing a subject rAAV virion, as described below. Where a subject host cell is used to produce a subject rAAV virion, it is referred to as a "packaging cell." In some embodiments, a subject host cell is stably genetically modified with a subject nucleic acid. In other embodiments, a subject host cell is transiently genetically modified with a subject nucleic acid.

A subject nucleic acid is introduced stably or transiently into a host cell, using established techniques, including, but not limited to, electroporation, calcium phosphate precipitation, liposome-mediated transfection, baculovirus infection, and the like. For stable transformation, a subject nucleic acid will generally further include a selectable marker, e.g., any of several well-known selectable markers such as neomycin resistance, and the like.

A subject host cell is generated by introducing a subject nucleic acid into any of a variety of cells, e.g., mammalian cells, including, e.g., murine cells, and primate cells (e.g., human cells). Suitable mammalian cells include, but are not limited to, primary cells and cell lines, where suitable cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), Sf9 cells, human embryonic kidney (HEK) cells (ATCC No. CRL1573), HLHepG2 cells, and the like.

In some embodiments, a subject genetically modified host cell includes, in addition to a nucleic acid comprising a nucleotide sequence encoding a variant AAV capsid protein, as described above, a nucleic acid that comprises a nucleotide sequence encoding one or more AAV rep proteins. In other embodiments, a subject host cell further comprises an rAAV vector. An rAAV virion can be generated using a subject host cell. Methods of generating an rAAV virion are described in, e.g., U.S. Patent Publication No. 2005/0053922 and U.S. Patent Publication No. 2009/0202490.

Methods

The present disclosure provides methods of delivering a gene product to a target cell in an individual by administering to the individual an rAAV virion of the present disclosure. The present disclosure provides a method of treating a disease, the method including administering to an individual in need thereof an effective amount of a subject rAAV virion as described above. The present disclosure further provides methods of generating rAAV virions that comprise a variant AAV capsid protein derived from an ancestral AAV capsid protein amino acid sequence.

Methods of Delivering a Gene Product to a Target Cell

The present disclosure provides a method of delivering a gene product to a target cell, e.g., a muscle cell or a glial cell, in an individual, the method comprising administering to the individual an rAAV virion of the present disclosure, as described above. The rAAV virion enters the target cell and the gene product encoded by the heterologous polynucleotide present in the rAAV virion is produced in the target cell. In some cases, the methods involve introducing an rAAV virion of the present disclosure to a site proximal to the target cell, where the rAAV virion enters the target cell and where the gene product encoded by the heterologous polynucleotide present in the rAAV virion is produced in the target cell.

Where the gene product is delivered to a muscle cell, the subject rAAV virions may be delivered using any suitable method, e.g., by a parenteral route, such as intramuscular injection. Methods for delivering a gene product into muscle using rAAV virions is described, e.g., in Wang et al., 2014 Expert Opin Drug Deliv. 11:345, which is incorporated herein by reference.

Where the gene product is delivered to the brain, one method for administration of the rAAV virion of the invention is by deposition into or near the site by any suitable technique, such as by direct injection (aided by stereotaxic positioning of an injection syringe, if necessary) or by placing the tip of an Ommaya reservoir into a cavity, or cyst, for administration. Alternatively, a convection-enhanced delivery catheter may be implanted directly into the site, into a natural or surgically created cyst, or into the normal brain mass (see e.g. US Application No. 20070254842, incorporated here by reference). Such convection-enhanced pharmaceutical composition delivery devices greatly improve the diffusion of the composition throughout the brain mass. The implanted catheters of these delivery devices utilize high-flow microinfusion (with flow rates in the range of about 0.5 to 15.0 µl/minute), rather than diffusive flow, to deliver the rAAV virion to the brain and/or tumor mass. Such devices are described in U.S. Pat. No. 5,720,720, incorporated fully herein by reference.

In some cases, a subject rAAV virion, when introduced into a target tissue of an individual, provides for high level production of the heterologous gene product encoded by the rAAV in the target tissue. For example, a heterologous polypeptide encoded by the rAAV can be produced in the target tissue at a level of from about 1 µg to about 50 µg, or greater than 50 µg.

In some cases, a subject rAAV virion, when introduced into a target tissue of an individual, provides for production of the heterologous gene product encoded by the rAAV in at least about 10%, at least about 15%, at least about 20%, at least about 25%, at least about 30%, at least about 35%, at least about 40%, at least about 50% at least about 60%, at least about 70%, at least about 80%, or more than 80%, of the target cells.

In some embodiments, a subject rAAV virion, when introduced into a target tissue of an individual, provides for production of the heterologous gene product encoded by the rAAV for a period of time of from about 2 days to about 6 months, e.g., from about 2 days to about 7 days, from about 1 week to about 4 weeks, from about 1 month to about 2 months, or from about 2 months to about 6 months. In some embodiments, a subject rAAV virion, when introduced into a target tissue of an individual, provides for production of the heterologous gene product encoded by the rAAV for a period of time of more than 6 months, e.g., from about 6 months to 20 years or more, or greater than 1 year, e.g., from about 6 months to about 1 year, from about 1 year to about 2 years, from about 2 years to about 5 years, from about 5 years to about 10 years, from about 10 years to about 15 years, from about 15 years to about 20 years, or more than 20 years.

Method of Treating a Disease

The present disclosure provides a method of treating a disease, the method including administering to an individual in need thereof an effective amount of a subject rAAV virion as described above. The subject rAAV virion can be administered via local injection to the pathological tissue, as described above, by any other convenient mode or route of administration. In certain embodiments, the individual is a patient who has been diagnosed with a disease, e.g., a cancer, such as a glioma, or a genetic disorder, such as a congenital enzyme deficiency or degenerative disease, as described above.

A "therapeutically effective amount" will fall in a relatively broad range that can be determined through experimentation and/or clinical trials. For example, for in vivo injection, e.g., injection directly into the muscle, a therapeutically effective dose will be on the order of from about $10^6$ to about $10^{15}$ of the rAAV virions, e.g., from about $10^8$ to $10^{12}$ rAAV virions. For example, for in vivo injection, e.g., injection directly into the muscle, a therapeutically effective dose will be on the order of from about $10^6$ to about $10^{15}$ infectious units, e.g., from about $10^8$ to about $10^{12}$ infectious units. Other effective dosages can be readily established by one of ordinary skill in the art through routine trials establishing dose response curves.

In some cases, a therapeutically effective amount of a subject rAAV virion is an amount that, when administered to an individual (e.g., administered via intramuscular injection of the individual) in one or more doses, is effective to slow the progression of muscle degeneration in the individual. For example, a therapeutically effective amount of a subject rAAV virion can be an amount that, when administered to an individual (e.g., administered via intramuscular injection to an individual) in one or more doses, is effective to slow the progression of muscle degeneration by at least about 15%, at least about 20%, at least about 25%, at least about 30%, at least about 40%, at least about 50%, at least about 60%, at least about 70%, at least about 80%, or more than 80%, compared to the progression of muscle degeneration in the absence of treatment with the rAAV virion.

In some cases, a therapeutically effective amount of a subject rAAV virion is an amount that, when administered to an individual in one or more doses, is effective to improve function of the diseased tissue in the individual. For example, a therapeutically effective amount of a subject rAAV virion can be an amount that, when administered to an individual (e.g., administered via intramuscular injection) in one or more doses, is effective to improve muscle function by at least about 15%, at least about 20%, at least about 25%, at least about 30%, at least about 40%, at least about 50%, at least about 60%, at least about 70%, at least about 80%, or more than 80%, compared to the individual's muscle function in the absence of treatment with the rAAV virion.

In some cases, a therapeutically effective amount of a subject rAAV virion is an amount that, when administered to an individual (e.g., administered via intramuscular injection) in one or more doses, is effective to decrease the rate of muscle strength loss in an affected muscle.

Method of Generating rAAV Virions with a Variant AAV Capsid Protein

Also provided herein is a method of generating rAAV virions containing variant AAV capsid proteins, e.g., AAV capsid proteins derived from ancestral AAV capsid protein amino acid sequence, through rounds of selection. In certain embodiments, the method includes subjecting a plurality of rAAV virions, e.g., a library of rAAV virions, to a first round of selection in target cells, wherein the rAAV virions in the initial library each contain an initial AAV capsid protein having an AAV capsid protein amino acid sequence, and wherein the AAV capsid protein amino acid sequences contain an ancestral AAV capsid protein amino acid sequence that differ among each other at one or more variable residues of the ancestral AAV capsid protein amino acid sequence, thereby generating rAAV virions that have variant AAV capsid proteins.

In some embodiments, the AAV capsid protein amino acid sequences are derived from an ancestral AAV capsid protein amino acid sequence. In such instances, the ancestral AAV capsid protein amino acid sequence is inferred from a plurality of orthologous, wild type AAV capsid protein sequences, as described herein. Thus, in some embodiments, the library of rAAV virions contains a diverse population of AAV capsid proteins whose amino acid sequences each represent one of a plurality of AAV capsid protein sequences obtained by setting residues in the ancestral AAV capsid protein amino acid sequence that are variable, i.e., those residues that cannot be inferred above a threshold level of confidence, to a specific amino acid.

Any suitable method may be used to infer the ancestral AAV capsid protein amino acid sequence from a plurality of orthologous, wildtype AAV capsid protein sequences. In general terms, reconstructing an ancestral amino acid sequence based on a plurality of orthologous, extant amino acid sequences may involve statistical reconstruction of an ancestral amino acid sequence, where each residue of the ancestral amino acid sequence is associated with a confidence value for an amino acid based on the extant amino acid sequences. Statistical reconstruction may include Markov chain Monte Carlo sampling of sequence alignments, trees and evolutionary model parameters, and estimation of their posterior probability distribution given the known sequences, as described in Westesson et al., Bioinformatics. 2012 28: 1170, which is incorporated by reference herein.

Typically, the full length ancestral sequence is not reconstructed because the amino acid identity of one or more residues cannot be determined above a threshold confidence level. These residues may be represented as polymorphic sites in the ancestral sequence. Thus, an ancestral library contains a plurality of polypeptides in which the amino acid identity of the residue at each polymorphic site may be variable from molecule to molecule, but across the library corresponds to the distribution of amino acids represented by the probabilities predicted based on the statistical reconstruction. In certain embodiments, the amino acid identity of the residue at each polymorphic site across the library fits a distribution of two or three amino acids defined by the probabilities predicted by the statistical reconstruction. In certain instances, the ancestral library containing inferred but variable ancestral amino acid sequences may be designed automatically (i.e., without manual selection) based on the statistical reconstruction method, as described herein. In such instances, the distribution of amino acids at any polymorphic residue of an amino acid sequence in the ancestral library is designed to reflect the probabilities predicted by the statistical reconstruction.

Thus, the method of inferring an ancestral AAV capsid protein amino acid sequence from a plurality of orthologous, wildtype AAV capsid protein sequences may include reconstructing a phylogenetic tree of a plurality of wild type AAV capsid protein amino acid sequences, selecting a node of the phylogenetic tree, and determining the most likely amino acid sequence at the node. In some cases, a confidence value at each node of the phylogenetic tree is estimated using a suitable method, e.g., Bayesian Markov chain Monet Carlo simulation. The confidence value at each node may inform the decision to select a specific node of the phylogenetic tree for inferring the ancestral sequence. Once a specific node of the phylogenetic tree is selected, the ancestral sequence may be inferred by aligning the wild type sequences that belong to the node, e.g., by a Markov chain Monte Carlo alignment method, as described above. In some instances, the most likely ancestral capsid protein amino acid sequence may contain polymorphic residues that are not assigned to a specific amino acid with a confidence level higher than a predetermined threshold. The distribution of amino acids at any of these polymorphic residues of the ancestral capsid protein amino acid sequence in the ancestral AAV library may be designed to reflect the probabilities predicted by the statistical reconstruction based on the wildtype AAV capsid protein sequences, as described above.

Other methods for inferring ancestral sequences are described in, e.g., Stackhouse, J, Presnell, S R, McGeehan, G M, Nambiar, K P, and Benner, S A (1990). The ribonuclease from an extinct bovid ruminant. *FEBS letters* 262: 104-106; Gaucher, E A, Govindarajan, S, and Ganesh, O K (2008). *Nature* 451: 704-707; Ortlund, E A, Bridgham, J T, Redinbo, M R, and Thornton, J W (2007). *Science* 317: 1544-1548; Ugalde, J A, Chang, B S, and Matz, M V (2004). Evolution of coral pigments recreated. *Science* 305: 1433; Alcolombri, U, Elias, M, and Tawfik, D S (2011). Directed evolution of sulfotransferases and paraoxonases by ancestral libraries. *Journal of molecular biology* 411: 837-853; Kothe, D L, Li, Y, Decker, J M, Bibollet-Ruche, F, Zammit, K P, Salazar, M G, et al. (2006). *Virology* 352: 438-449; Ducatez, M F, Bahl, J, Griffin, Y, Stigger-Rosser, E, Franks, J, Barman, S, et al. (2011). *Proceedings of the National Academy of Sciences of the United States of America* 108: 349-354; Rolland, M, Jensen, MA, Nickle, D C, Yan, J, Learn, G H, Heath, L, et al. (2007). *Journal of virology* 81: 8507-8514; Gullberg, M, Tolf, C, Jonsson, N, Mulders, M N, Savolainen-Kopra, C, Hovi, T, et al. (2010). *Journal of virology* 84: 9695-9708, which are incorporated herein by reference.

In some embodiments, the initial, e.g., ancestral, AAV capsid protein has an amino acid sequence at least 94%, e.g., at least 95%, e.g., at least 96%, at least 97%, at least 98%, at least 99%, or 100% identical to the sequence set forth in SEQ ID NO: 7.

Selection may be achieved when individual rAAV virions of the library compete among each other to infect and replicate in the host cell. Without being held to theory, some variants among the initial, e.g., ancestral, AAV capsid protein amino acid sequences present in the rAAV library confer differential infectivity to the virion, and therefore, those virions that have a variant AAV capsid protein that confer higher infectivity than all other variant AAV capsid proteins will tend to become more abundant. In certain cases, selection generates a library of rAAV variants containing a variant AAV capsid protein that confers to a virion a general higher infectivity, e.g., for multiple cell types, or in other cases selection generates a library of rAAV variants containing a virion with higher infectivity for one or a few specific cell types, e.g., a muscle cell and/or glial/glioblastoma cell.

In some instances, the second library of rAAV virions has a different distribution of amino acids at one or more variable residues of the ancestral AAV capsid protein amino acid sequence over the population of variant AAV capsid proteins in the library compared to the initial library of rAAV virions containing the initial AAV capsid protein amino acid sequences. In some instances, the second library of rAAV virions has a different distribution of amino acids at one or more of residues 264, 266, 268, 448, 459, 460, 470, 471, 474, 495, 516, 533, 547, 551, 555, 557, 561, 563, 577, 583, 593, 596, 661, 662, 664, 665, 710, 717, 718, 719 and 723 of SEQ ID NO: 7 over the population of variant AAV capsid proteins in the library, compared to the initial library of rAAV virions containing the initial AAV capsid protein amino acid sequences.

In general, the subjecting step may include infecting target cells with the plurality of rAAV virions, superinfecting the infected cells with a helper virus, and harvesting rAAV virions released from superinfected cells. Methods of infecting, superinfecting and harvesting rAAV virions from target cells is as described for generating rAAV virions in a host cell described above.

The stringency of the selection may be controlled according to any suitable method. In certain embodiments, the stringency of selection is correlated with the multiplicity of infection (MOI) used when infecting the target cells with the rAAV virions. In general terms, the MOI is the ratio of the number of viral particles to the number of target cells present when infecting the target cells with the virions. The higher the multiplicity of infection is, the weaker the stringency of selection, and vice versa.

In certain embodiments, the rAAV variants generated according to the selection method described above is subjected to a second round of selection. The second round of selection may in some instances have the same or higher stringency than the first round of selection. For example, if the MOI for the first round of selection is 5,000, the second round of selection may have a higher stringency MOI of 500, etc. In such a way, a third library of rAAV virions that contain variant AAV capsid proteins is generated. In some instances, the third library of rAAV virions generated after the second round of selection has a different distribution of amino acids at one or more variable residues of the ancestral AAV capsid protein amino acid sequence over the population of variant AAV capsid proteins in the library compared to the initial or second libraries of rAAV virions. In certain embodiments, the third library of rAAV virions generated after the second round of selection has a different distribution of amino acids at one or more of residues 264, 266, 268, 448, 459, 460, 470, 471, 474, 495, 516, 533, 547, 551, 555, 557, 561, 563, 577, 583, 593, 596, 661, 662, 664, 665, 710, 717, 718, 719 and 723 of SEQ ID NO: 7 over the population of variant AAV capsid proteins in the library, compared to the initial or second libraries of rAAV virions.

In certain embodiments, a plurality of rounds of selection, such as 2 or more, 3 or more, 4 or more, 5 or more, 6 or more, 7 or more, 8 or more, or 10 or more rounds of selection is carried out sequentially to generate rAAV variants. In certain embodiments, the plurality of rounds of selection is carried out in the same target cell type. In certain cases, the multiple rounds of selection generates rAAV variants containing a variant AAV capsid protein that confers to the rAAV virion a general, high infectivity, i.e., an infectivity above background for multiple cell types, or in other cases, the multiple rounds of generates rAAV variants containing a variant AAV capsid protein that confers to the rAAV virion higher infectivity for one or a few specific cell types, e.g., a muscle cell and/or glial/glioblastoma cell, compared to an AAV virion with a wild type AAV capsid protein.

Utility

A subject rAAV virion comprising a variant AAV capsid protein, as described above, finds use in many applications where expression of a heterologous gene product in a target cell is desired. In certain embodiments, when the variant AAV capsid protein confers to the rAAV virion a higher infectivity for a specific cell type, i.e., confers tropism for a target cell type, the rAAV virion may be used to express a therapeutic gene product in or from tissue containing the target cell in a patient in need of therapy. For example, the subject rAAV virions may contain an AAV capsid protein that confers tropism for muscle cells and a gene product for treating a genetic deficit in the patient. In certain embodiments, the genetic deficit includes a deleterious mutation in the coding sequence or regulatory sequence for LPL, factor IX, α$_1$-antitrypsin, follistatin, soluble myostatin receptor, apelin, glucagon-like peptide 1, insulin-like growth factor 1, troponins, laminins, collagens, lamin, selenoprotein N, protein-O-mannosyltransferase, fukutin, LARGE, O-linked mannose β1,2-N-acetylglucosaminyl-transferase, and isoprenoid synthase domain-containing protein, etc. In certain cases, the patient is diagnosed with a congenital condition caused by lack of functional expression of enzymes and other proteins, as described above. Thus, in certain instances, the subject rAAV virions is administered to a patient diagnosed with muscular dystrophy, hypertriglyceridemia, hemophilia B, hereditary emphysema, familial hypertrophic cardiomyopathy, cystic fibrosis, early onset retinal degeneration, amyotrophic lateral sclerosis, Leber's congenital amaurosis, Canavan disease, late infantile neuronal ceroid lipofuscinosis, etc.

In certain embodiments, the rAAV virions may be administered to a patient diagnosed with a condition caused or exacerbated by a genetic mutation. In some instances, the condition is caused by or exacerbated by a genetic mutation associated with a tumor. In some instances, the tumor is a glioma, malignant melanoma, prostate cancer, etc. In certain embodiments, the rAAV virions may be administered to a patient diagnosed with a neurological disorder (e.g., Parkinson's disease, Alzheimer's disease, epilepsy, etc.) caused by or exacerbated by a genetic mutation. Exemplary use of AAV virions for gene therapy is described in, e.g., Santos Coura et al., 2007 Virol J. 4:99, which is incorporated by reference herein.

In certain embodiments, the subject rAAV virions containing an AAV capsid protein that confers tropism for a pathological cell in the patient, and a nucleic acid gene product or a genome editing gene product for treating the patient is administered to treat a patient diagnosed with a congenital disease. In some embodiments, the congenital disease may be a dominant genetic disorder caused by, e.g., a dominant-negative effect exerted by a defective protein expressed from a mutated gene in the patient's genome. In certain embodiment, the expression of a defective protein is reduced or inhibited by the nucleic acid gene product, e.g., an interfering RNA, that targets the mRNA encoded by the mutated gene. In some embodiments, the genome editing gene product, e.g., ZFN agent, TALENs, or a Cas9/gRNA system, is configured to target the mutated gene in the patient's genome to achieve allele-specific knockdown of a genetic locus causing a dominant genetic disorder. In certain embodiments, the patient is diagnosed with Hungtinton's disease, Marfan syndrome, etc.

rAAV virions and methods of the present disclosure also find use in generating, through selection, rAAV virions containing variant AAV capsid proteins that confer higher infectivity, tropism and/or altered dependency on host cell receptors that are desirable for an intended purpose, compared to a wild type AAV capsid protein. In certain embodiments, the ancestral AAV capsid protein sequences may be used as a starting point to generate rAAV virions containing variant AAV capsid proteins that confer high infectivity and tropism for a non-permissive cell type, i.e., a cell type refractory to infection by a rAAV virion containing a wild type AAV capsid protein. In certain embodiments, the non-permissive cell type is a glioblastoma cell, a human megakaryocytic leukemia cell, etc.

Kits

Also provided herein are kits that include the subject rAAV virions, or a library of rAAV virions, and that find use in practicing the disclosed methods. In certain embodiments, the kit includes infectious rAAV virions containing a variant AAV capsid protein and a heterologous nucleic acid encoding a gene product, as described above. In some cases, the gene product may be a therapeutic gene product. In some embodiments, the kit may also contain a pharmaceutically acceptable carrier, diluent, excipient, or buffer, in the same or separate container as the container holding the infectious rAAV virions.

In certain embodiments, the kit contains a library of infectious rAAV virions, wherein the library contains a plurality of AAV capsid proteins derived from an ancestral AAV capsid protein amino acid sequence. In certain cases, the ancestral AAV capsid proteins confer increased thermo-stability and/or promiscuity of infection to the rAAV virions compared to rAAV virions containing wild type AAV capsid proteins. In certain embodiments, the kit further contains a helper virus. In certain embodiments, the kit contains one or more plasmids containing genes required in the host cell infected by the rAAV virions for replication of the rAAV virions.

Components of a subject kit can be in separate containers; or can be combined in a single container.

In addition to above-mentioned components, a subject kit can further include instructions for using the components of the kit and to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

AAV Ancestral Reconstruction Library Enables Selection of Broadly Infectious Viral Variants Methods
Ancestral Reconstruction Adeno-associated virus (AAV) cap sequences (n=52) from Genbank, including those from human and non-human primate origin, were incorporated in this analysis, starting from lists of AAV sequences published in previous phylogenetic analyses. The MrBayes package was used to perform Bayesian Markov chain Monte Carlo (MCMC) simulation of tree space and estimate the confidence values at each internal node. the Markov chain Monte Carlo alignment sampler HandAlign was then used to explore alignment space and estimate regional confidence for the most likely alignment at node 27, discarding all but the sequences descended from this node. HandAlign generates a multiple sequence alignment, arranging the sequences of different variants in aligned 'columns' such that residues grouped in a column share a common ancestor. Each alignment column was modeled as a realization of the standard phylogenetic continuous-time Markov process of character evolution, using amino acid and empirical codon substitution rate matrices that were estimated from databases of aligned protein-coding sequence. HandAlign performs the reconstruction simultaneously with the alignment, and accounts for sequence insertions, deletions, and character substitutions. The codon-level model was used to account for the possibility of synonymous substitutions with a phenotype at the DNA level; the possibility of dual selection in overlapping reading frames ("overprinted" genes) checked was also checked, by reconstructing both ancestral reading frames at the codon level. Neither of these subtle effects appeared significant enough to warrant prioritizing synonymous (silent, DNA-level) variants over the many non-synonymous amino acid variants. The JalView program was used to visualize the variant amino acid positions mapped onto the assembled capsid structure.

Library Construction and Vector Packaging

The reconstructed ancestral AAV cap sequence was synthesized (GeneArt, Life Technologies) with a library size of $5.6\times10^{11}$, digested with Hind III and Not I, and ligated into the replication competent AAV packaging plasmid pSub2. The resulting ligation reaction was electroporated into *E. coli* for plasmid production and purification. Replication competent AAV was then packaged and purified by iodixanol density centrifugation as previously described. DNase-resistant genomic titers were obtained via quantitative real time polymerase chain reaction (PCR) using a Biorad iCycler (Bio-Rad, Hercules, Calif.) and Taqman probe (Biosearch Technologies, Novato, Calif.).

Cell Culture

C2C12 mouse myoblast, B16-F10 skin melanoma cells, Chinese hamster ovary (CHO)-K1, pgsA, Pro5, Lec1, and Lec2 cells were obtained from the Tissue Culture Facility at the University of California, Berkeley. IB3-1 lung epithelial and human embryonic kidney 293T cells were obtained from American Type Culture Collection (Manassas, Va.). Unless otherwise noted all cell lines were cultured in Dulbecco's Modified Eagle's medium (DMEM, Gibco) at 37° C. and 5% $CO_2$. L0 human glioblastoma (GBM) tumor initiating cells were kindly provided by Dr. Brent Reynolds (University of Florida, Gainesville), and propagated in neurosphere assay growth conditions with serum-free media (Neurocult NS-A Proliferation kit, Stem Cell Technologies) that contained epidermal growth factor (EGF, 20 ng/ml, R&D), basic fibroblast growth factor (bEGF, 10 ng/ml, R&D), and heparin (0.2% diluted in phosphate buffered saline, Sigma). IB3-1 cells were cultured in DMEM/F-12 (1:1) (Invitrogen, Carlsbad, Calif.). CHO-K1 and pgsA cells were cultured in F-12K medium (ATCC), and Pro5, Lec1, and Lec2 cells were cultured in MEM a nucleosides (Gibco). Except for GBM culture, all media were supplemented with 10% fetal bovine serum (Invitrogen) and 1% penicillin/streptomycin (Invitrogen).

Library Selection and Evolution

All cell lines were seeded in 6-well tissue culture plates at a density of $1\times10^5$ cells per well. One day after seeding, cells were infected with replication competent AAV libraries. After 24 hours of exposure, cells were superinfected with adenovirus serotype 5 (Ad5). Approximately 48 hours later, cytopathic effect was observed, and virions were harvested by three freeze/thaw steps followed by treatment with Benzonase nuclease (1 unit/mL) (Sigma-Aldrich) at 37° C. for 30 minutes. Viral lysates were then incubated at 56° C. for 30 minutes to inactivate Ad5. The viral genomic titer was determined as described above. To analyze cap sequences AAV viral genomes were extracted after packaging and rounds 3 and 6 of selection, amplified by PCR, and sequenced at the UC Berkeley DNA Sequencing Facility.

Statistical Analysis of Variable Positions in Evolved Ancestral Libraries

A comparison of the two sets of variable amino acids at each variable amino acid position was conducted to identify variable positions that whose library proportions had changed significantly during selection. The posterior probability that the two sets of variable amino acids come from two different probability distributions was calculated assuming probability parameters that are Dirichlet-distributed with low pseudocounts to reflect sparse observed counts. For comparison of the synthesized and theoretical library, post-synthesis amino acid frequencies distributed via a Dirichlet-multinomial were compared with the theoretical probabilities from the library distributed by a multinomial.

In vitro Transduction Analysis

Ancestral library viral genomes selected through six rounds of evolution were cloned into the pXX2 recombinant AAV packaging plasmid. To benchmark the infectivity of recombinant AAV (rAAV) ancestral libraries against a panel of natural AAV serotypes, vectors were packaged with a self-complementary cytomegalovirus-green fluorescent protein (CMV-GFP) cassette using the transient transfection method previously described. Cell lines (293T, C2C12, IB3-1, B16-F10, CHO-K1, pgsA, Pro5, Lec1, and Lec2) were seeded in 96-well plates at a density of 15,000 cells per well. One day after seeding, cells were infected with rAAV at a genomic multiplicity of infection (MOI) of 2,000 (293T, C2C12, IB3-1, B16-F10, GBM), 10,000 (Pro5, Lec1, Lec2), 32,000 (C2C12), or 50,000 (CHO-K1, pgsA) (n=3). For experiments studying glycoprotein usage, Pro5 cells were treated with 0.05% trypsin (Gibco) or mock treated with phosphate buffered saline (PBS) prior to transduction as previously described, and cells were infected at a genomic MOI of 5,000 (ancestral AAVs, AAV2, AAV6) or 15,000 (AAV5). To analyze antibody evasion properties, ancestral rAAV libraries were incubated at 37° C. for 1 hour with serial dilutions of heat inactivated IVIG (Gammagard), and then used to infect HEK293T cells at a genomic MOI of 2000 (n=3). To characterize thermostability, virions packaged with self-complementary CMV-GFP were diluted with DMEM supplemented with 2% FBS and incubated at temperatures ranging from 59.6° C. to 78° C. for 10 minutes in a thermocycler (Bio-Rad) before being cooled down to 37° C. and used to infect 293T cells at genomic MOIs ranging from 1,500-16,000; MOIs were adjusted to ensure an adequate number of GFP-positive cells for analysis. For all studies, the fraction of GFP-expressing cells 72 hours post-infection was quantified with a Guava EasyCyte 6HT flow cytometer (EMD/Millipore) (UC Berkeley Stem Cell Center, Berkeley, Calif.).

In Vivo Animal Imaging and Quantification of Luciferase Expression

High-titer rAAV dsCAG-Luciferase vectors were purified by iodixanol gradient and then concentrated and exchanged into PBS using Amicon Ultra-15 centrifugal filter units (Millipore). To study skeletal muscle transduction $5\times10^{10}$ rAAV-Luc DNase-resistant genomic particles were injected in a volume of 30 μl into each gastrocnemius muscle of 7-week-old female BALB/c mice (Jackson Laboratories, n=3) as previously described. Six weeks after injection, animals were sacrificed, and gastrocnemius muscle was harvested and frozen. Luciferase activity was determined and normalized to total protein as previously described. All animal procedures were approved by the Office of Laboratory Animal Care at the University of California, Berkeley and conducted in accordance with National Institutes of Health (NIH) guidelines on laboratory animal care.

Results

Ancestral AAV Sequence Reconstruction

The goals of ancestral sequence reconstruction are, given a set of extant DNA sequences, to generate a phylogenetic tree and sequence alignment that relates these sequences, and to infer the sequences of ancestral variants at different ancestral nodes. Accurate sequence reconstruction is challenging due to ambiguity in the evolutionary relationships between extant variants (which affects the phylogenetic tree-building step) as well as sequence divergence at highly variable residues (which affects the sequence alignment and ancestral reconstruction steps). As the starting point for AAV ancestral reconstruction, the phylogeny of selected human, macaque and rhesus monkey AAV cap sequences retrieved from Genbank (n=52) was reconstructed. MrBayes, which conducts Bayesian Markov chain Monte Carlo (MCMC) simulation of tree space, was used to estimate the confidence values at each internal node (shown in curly braces in FIGS. 1a and 2). This approach generates a phylogenetic tree relating extant sequences, which is essentially a hypothesis concerning the evolutionary history of AAVs. Each branch on this tree describes the evolutionary process that diversified the sequences, and each internal node represents a 'splitting' event where two AAV lineages diverged. With many ancestral nodes to choose from, node 27 was selected (FIG. 1, panel a) based on its high confidence value (1.00), which minimizes one potential source of uncertainty (at the level of phylogenetic relationships between entire sequences) and thus improves confidence in the finer-grained downstream reconstruction of individual amino acids' evolutionary histories. This node is also the ancestor of serotypes with demonstrated clinical efficacy (AAV1, Glybera), biomedical interest (AAV6), or relative resistance to neutralizing antibodies (AAV7).

FIG. 1. Ancestral AAV sequence reconstruction. a) A phylogenetic tree relating a subset of extant AAV variants at node 27. Curly braced numbers indicate clade posterior probabilities. The phylogenetic tree graphic was generated in Dendroscope. b) A multiple sequence alignment of a subset of AAV variants with column-specific confidence colored and annotated along the top with single digits (hu.31 and hu.32-SEQ ID NO: 1; cy.6 and rh.13-SEQ ID NO: 2; rh.2, rh.50, hu.67, rh.10, and rh.55-SEQ ID NO: 3; rh.51-SEQ ID NO: 4; rh.49-SEQ ID NO: 5; cy.4-SEQ ID NO: 6). Confidence ranges from above 0.9 to 0.3-0.4 are shown in the top line. c) A distribution of predicted ancestral amino acid sequences for node 27, residues 451-481. The character height of each amino acid is proportional to its posterior probability.

FIG. 2. Full phylogenetic tree for AAV ancestral sequence reconstruction. Curly braced numbers indicate clade posterior probabilities. The phylogenetic tree graphic was generated in Dendroscope.

The Markov chain Monte Carlo alignment sampler HandAlign was then used to explore alignment space and predict the ancestral sequence of the most likely alignment at node 27. HandAlign generates a multiple sequence alignment, arranging the sequences of different variants in aligned 'columns' such that residues grouped in a column share a common ancestor (FIG. 1, panel b). HandAlign performs the ancestral reconstruction simultaneously with the alignment, and accounts for sequence insertions, deletions, and character substitutions. Shown in FIG. 1c is the distribution of predicted amino acids as a sequence logo, with character heights proportional to posterior probabilities. The majority of amino acid positions could be predicted with high confidence (>0.90) and thus represented residues highly conserved during evolution. However, as is common in ancestral reconstruction, other positions were less evolutionarily conserved and could thus be predicted with lower probabilities.

A DNA library was designed based on these results, and residues above the 0.90 confidence value were fixed while those below this confidence level but above a threshold value of 0.08 were varied by introducing the two or three most likely amino acids, such that the fraction of library members containing each amino acid at a given position reflects the probability of that amino acid appearing in the sequence reconstructions. The locations, identities, and synthesis frequencies of the 32 variable residues are presented in Table 1, and the full ancestral cap amino acid sequence is shown in FIG. 3 (SEQ ID NO: 7) and aligned with extant serotypes in FIG. 4. The ancestral cap library was synthesized (GeneArt, Life Technologies), and analysis of 61 sequenced clones from this library revealed that the amino acid frequencies at variable positions were not significantly different from the theoretical probabilities from the library (P<0.001, see Materials and Methods), highlighting the correctness of the library synthesis.

FIG. 3. Ancestral AAV cap amino acid sequence. Variable residues are labeled with a bold, underlined letter X.

Figure 4:
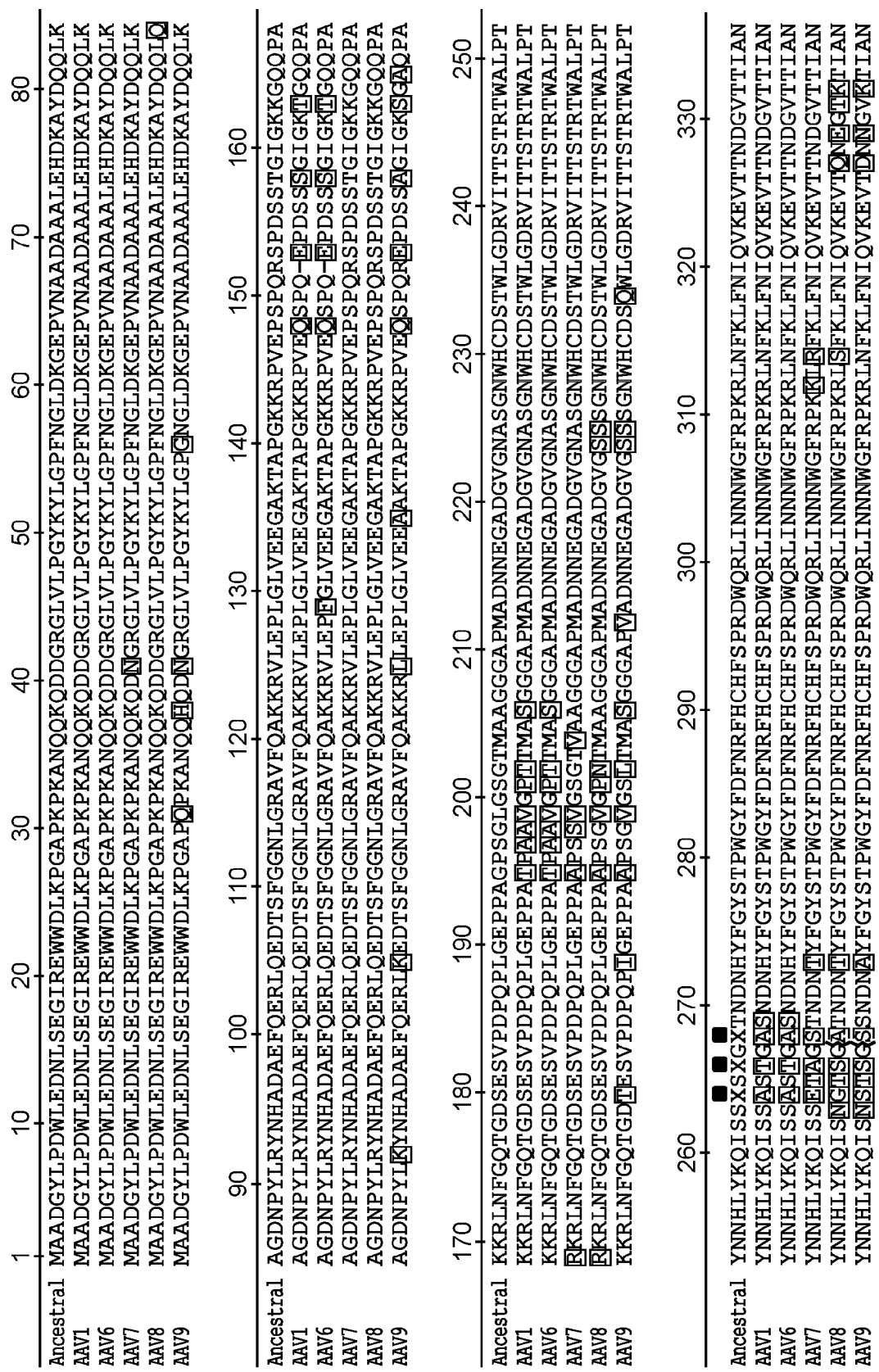
FIG. 4 shows an alignment of the ancestral AAV cap protein with natural serotypes (Ancestral-SEQ ID NO: 7; AAV1-SEQ ID NO: 8; AAV6-SEQ ID NO: 9; AAV7-SEQ ID NO: 10; AAV 8-SEQ ID NO: 11; AAV9-SEQ ID NO: 12).
Figure 4:
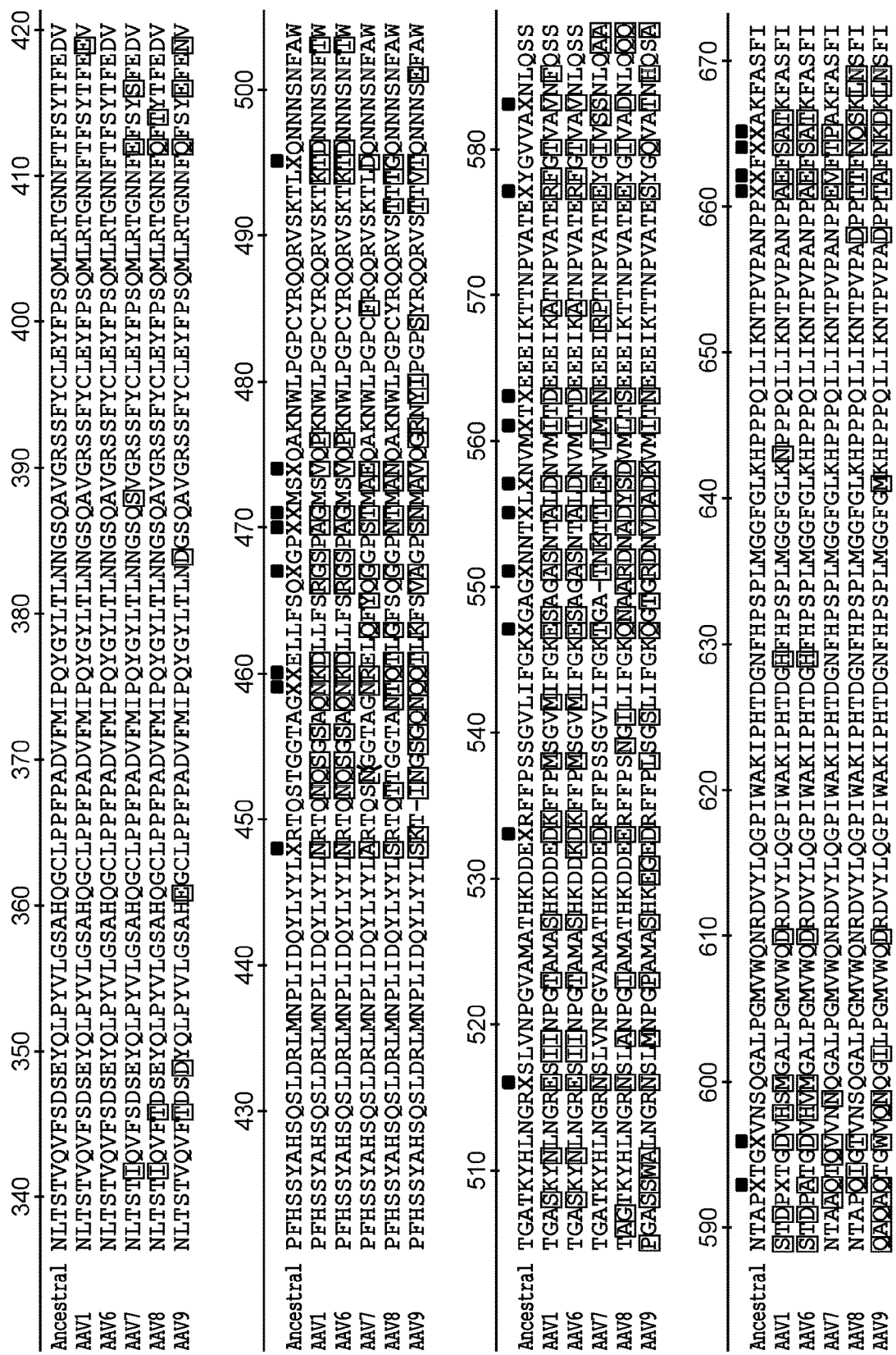
Figure 4:
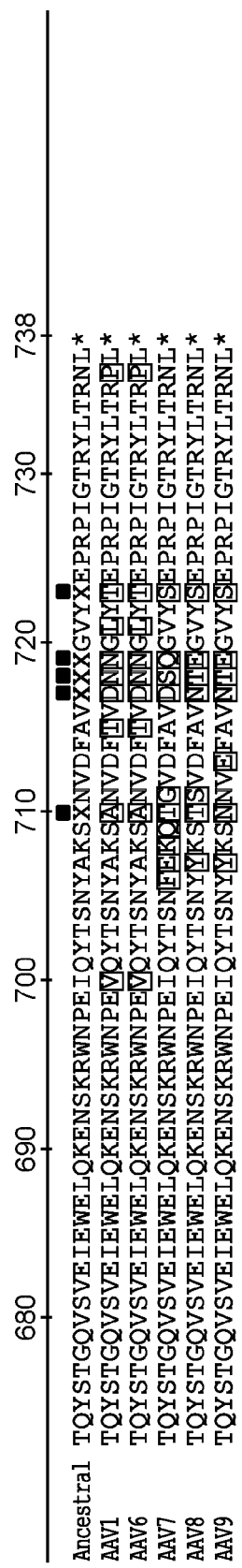

FIG. 4. Alignment of the ancestral AAV cap protein with natural serotypes.

Capsid amino acids were aligned using the Geneious program (Biomatters). Colored amino acids represent disagreements with the reference ancestral cap sequence. The variable positions in the ancestral library are annotated in black and designated with the letter X.

TABLE 1

| Position | Residue 1 | % Freq. | Residue 2 | % Freq. | Residue 3 | % Freq. |
|---|---|---|---|---|---|---|
| 264 | T | 55 | Q | 25 | A | 20 |
| 266 | A | 63 | S | 37 | | |
| 268 | S | 70 | A | 30 | | |
| 448 | S | 71 | A | 29 | | |
| 459 | T | 69 | N | 31 | | |
| 460 | R | 63 | Q | 20 | K | 17 |
| 467 | A | 75 | G | 25 | | |
| 470 | S | 85 | A | 15 | | |
| 471 | N | 60 | T | 32 | S | 8 |
| 474 | A | 83 | E | 16 | | |
| 495 | S | 75 | T | 25 | | |
| 516 | D | 91 | N | 9 | | |
| 533 | D | 86 | E | 14 | | |
| 547 | Q | 81 | E | 11 | T | 8 |
| 551 | A | 50 | K | 50 | | |
| 555 | T | 54 | A | 46 | | |
| 557 | E | 86 | D | 14 | | |
| 561 | M | 62 | L | 28 | I | 10 |
| 563 | S | 80 | N | 19 | | |
| 577 | E | 50 | Q | 50 | | |
| 583 | S | 86 | D | 8 | A | 6 |
| 593 | A | 45 | Q | 39 | V | 16 |
| 596 | A | 81 | T | 19 | | |
| 661 | A | 71 | E | 19 | T | 10 |
| 662 | V | 53 | T | 26 | A | 22 |

TABLE 1-continued

| Position | Residue 1 | % Freq. | Residue 2 | % Freq. | Residue 3 | % Freq. |
|---|---|---|---|---|---|---|
| 664 | T | 66 | S | 34 | | |
| 665 | P | 64 | A | 26 | Q | 10 |
| 710 | T | 87 | A | 13 | | |
| 717 | N | 69 | D | 31 | | |
| 718 | N | 60 | S | 40 | | |
| 719 | E | 79 | D | 21 | | |
| 723 | S | 68 | T | 32 | | |

Genetic Selection of Ancestral AAV Library

After validating the initial synthesized distribution of amino acids at the 32 variable positions, how those positions would change when subjected to selective pressure for packaging and infectivity, which are key factors for successful viral replicative fitness during the natural evolution of AAV, was probed. The ancestral library was cloned into an AAV packaging plasmid, and viral particles were produced by transfection into human embryonic kidney 293T cells as previously described. The viral genomic titer was comparable to levels obtained when packaging libraries based on extant AAV serotypes, indicating that the ancestral library can support robust packaging titers. The amino acid distribution at variable positions was only slightly altered by one round of packaging (FIG. 5), and it was hypothesized that additional selective pressure for infectivity may reveal more about the significance of each variable position. Five cell lines representative of different tissues were chosen to conduct rounds of selection: C2C12 mouse myoblast cells, IB3-1 lung epithelial cells, B16-F10 skin melanoma cells, human embryonic kidney 293T cells, and L0 human glioblastoma (GBM) tumor-initiating cells. Briefly, $1 \times 10^5$ cells were infected with iodixanol-purified, replication-competent AAV libraries at an initial genomic multiplicity of infection (MOI) of $10^4$. After two days, successful virions were recovered by superinfecting the cells with adenovirus type 5. Six rounds of selection were conducted on each cell line, and the stringency of selection was increased during subsequent rounds by decreasing the genomic MOI (Table 2).

FIG. 5. Dominant amino acids at variable positions after six rounds of selection. A heat map was generated based on the frequency of the most common amino acid at each position in the different libraries. The dominant amino acid and frequency at each position were determined based on sequencing results from individual clones n=61 (synthesized library), n=23 (post-packaging), and n=14 (ancestral libraries after selection on respective cell lines).

TABLE 2

Selection stringency applied in ancestral AAV library selections.

| Round of Selection | Genomic Multiplicity of Infection |
|---|---|
| 1 | 5,000 |
| 2 | 500 |
| 3 | 250 |
| 4 | 250 |
| 5 | 50 |
| 6 | 25 |

Figure 6A:
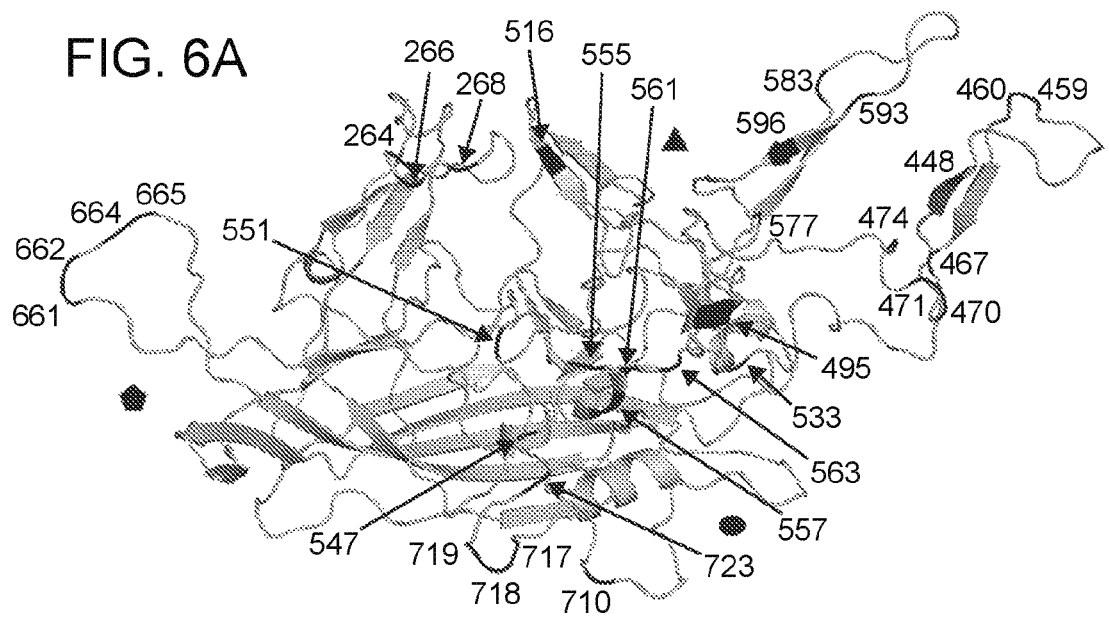
FIG. 6A-6B are images that shows variable residues of AAV cap amino acids, mapped to the crystal structure of homologous AAV1, in ancestral AAV variants after selection.
Figure 6B:
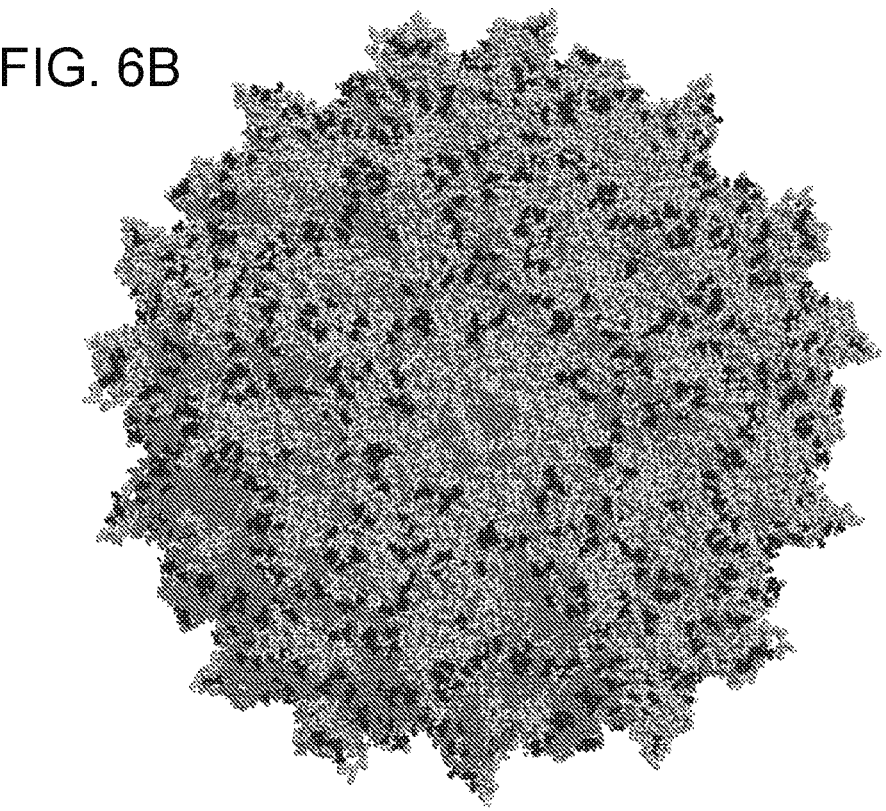

To assess the progression of selection at each variable position, clones were sequenced (n≥14) from each library after initial viral packaging (hereafter referred to as post-packaging), after three rounds of selection, and after six rounds of selection. This analysis revealed a range of outcomes for each variable position across the different cell lines. FIG. 6 shows the positions of the variable amino acids mapped onto the crystal structure of AAV1 (the most homologous serotype with a solved structure), and FIGS. 5 and 7 depict the dominant amino acid at each of these positions for each selected pool after six and three rounds of selection, respectively. As expected, selection for infection of cell lines led to increased convergence, and FIGS. 8 and 9 show the percentage change in amino acid frequency in rounds 6 and 3, respectively, relative to post-packaging. Some amino acid positions approach full convergence to the same residue across all cell lines (268, 460, 474, 516, 547, 583, 665, 710, 717, 719); these positions are distributed throughout the capsid and may for example be important for core viral functions such as capsid stability, uncoating, or endosomal escape. Others show more diverse outcomes across different cell lines (264, 467, 593, 664, 723) and may be neutral with respect to overall fitness. Finally, some positions (459, 470, 471, 533, 555, 596, 662, 718) acquired identities specific to a given cell line and may confer an infectious advantage on each respective cell line. The majority of these specific residues are exposed on the surface of the capsid, and they may thus play a role for example in altering the affinity of capsid interactions with cell surface receptors.

FIG. 6. Variable residues mapped to the crystal structure of homologous AAV1, the closest AAV relative with an available structure. A three-dimensional molecular model of the AAV1 capsid was generated in PyMOL. An amino acid alignment of the ancestral AAV sequence with AAV1 was used to map the highlighted residues to the a) individual asymmetric unit and b) full biological assembly.

FIG. 7. Dominant amino acids at variable positions after three rounds of selection. A heat map was generated based on the frequency of the most common amino acid at each position in the different libraries. The dominant amino acid and frequency at each position were determined based on sequencing results from individual clones (n≥14).

FIG. 8. Change in amino acid frequency at variable positions after six rounds of selection. The percent change in amino acid frequency between the post-packaging library and evolved libraries after six rounds of selection on each cell line was calculated. If the identity of the dominant amino acid did not change, the increase or decrease in frequency is displayed. If selection resulted in a change in amino acid identity at that position, the new amino acid and frequency is shown.

FIG. 9. Change in amino acid frequency at variable positions after three rounds of selection. The percent change in amino acid frequency between the post-packaging library and evolved libraries after three rounds of selection on each cell line was calculated. If the identity of the dominant amino acid did not change, the increase or decrease in frequency is displayed. If selection resulted in a change in amino acid identity at that position, the new amino acid and frequency is shown.

To determine whether the changes in amino acid frequencies imparted by genetic selection were statistically significantly different from the initial synthesized distribution, Bayesian Dirichlet-multinomial model comparison tests (as described in Materials and Methods) was conducted to calculate the posterior probability that the two sets of variable amino acids come from different distributions. This analysis identified several amino acid positions that are significantly different after selection (P<0.05) and many more that are moderately different (P<0.5) (FIG. 10).

FIG. 10. Identification of key variable residues by Bayesian Dirichlet-multinomial model comparison tests. A comparison of the two sets of variable amino acids was conducted to identify positions that changed significantly during selection. The posterior probability that the two sets of amino acids come from two different probability distributions was calculated assuming probability parameters that are Dirichlet-distributed with low pseudocounts to reflect sparse observed sequences. Results colored green indicate a >95% chance that the sets came from different distributions, yellow a >50% chance, red a >5% chance, and no color a <5% chance. Synth, synthesized library; PP, post-packaging; R3, round three of selection; R6, round six of selection.

Transduction Efficiency of Evolved Ancestral Libraries

Figure 11:
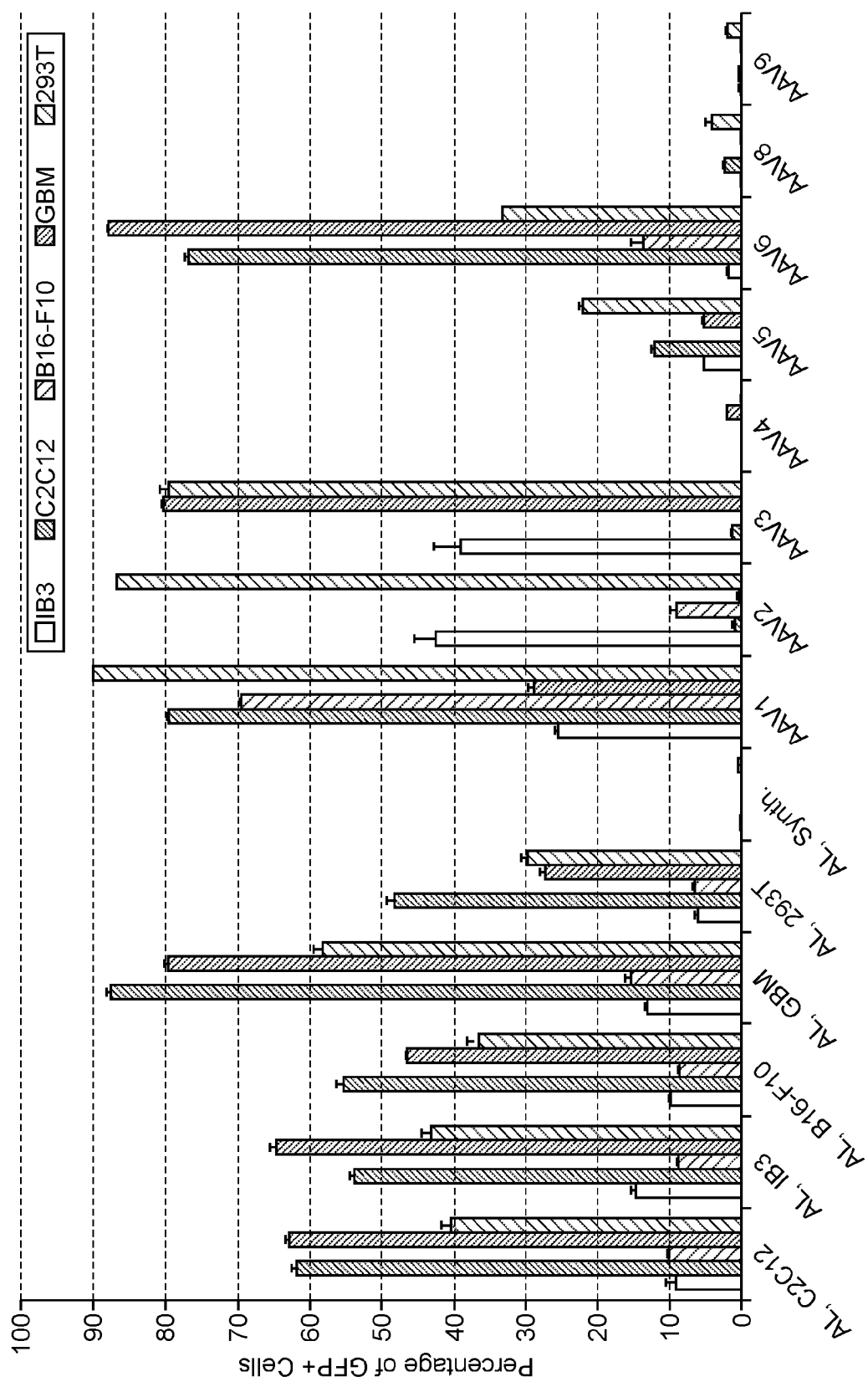
FIG. 11 shows transduction efficiency of evolved ancestral libraries benchmarked against natural AAV serotypes, according to an embodiment of the present disclosure.

Genetic selection could conceivably lead to specific infectivity of a given cell line or may alternatively increase overall infectivity but in a promiscuous manner across all cell types. These possibilities were investigated by evaluating the transduction efficiency of evolved ancestral libraries on the cell line panel. Six rounds of selection did not drive full convergence to a single sequence, potentially due to the presence of neutral positions that conferred no selective advantage. Therefore, rather than packaging individual clones, initially the entire evolved library was packaged as recombinant virus (at a low ratio of AAV helper plasmid per producer cell to minimize mosaic capsids), and results thus represent an overall or average library infectivity. High titer, iodixanol-purified recombinant AAV (rAAV) encoding the green fluorescent protein (GFP) was produced for the ancestral libraries and natural serotypes AAV1-6, 8, and 9, for comparison of transduction efficiency and tropism. Infection at a genomic MOI of 2,000 (or 32,000 for C2C12s) revealed a range of properties (FIG. 11). Evolved ancestral libraries mediated high delivery efficiencies most comparable to AAV1 and AAV6 and generally superior to AAV4, AAV5, AAV8, and AAV9. Ancestral libraries were especially successful in infecting C2C12 and GBM cell lines relative to natural serotypes. Importantly, a large increase in infectivity when comparing the synthesized vs. the evolved ancestral libraries was observed, suggesting genetic selection of advantageous amino acids at the variable positions. Interestingly, the evolved libraries in general displayed broad infectivity across all cell lines, suggesting that the ancestral AAV was promiscuous, a property known to be advantageous for natural evolutionary adaptability.

FIG. 11. Transduction efficiency of evolved ancestral libraries benchmarked against natural AAV serotypes. After six rounds of evolution, viral genomic DNA was recovered from ancestral libraries and packaged as rAAV scCMV-GFP along with wild type AAV 1-6, 8, and 9. Cell lines were infected at a genomic multiplicity of infection (MOI) of 2,000 (293T, IB3, B16-F10, GBM) or 32,000 (C2C12). The fraction of GFP expressing cells was quantified by flow cytometry 72 hours later. Data are presented as mean±SEM, n=3. AL, ancestral library.

Figure 12A:
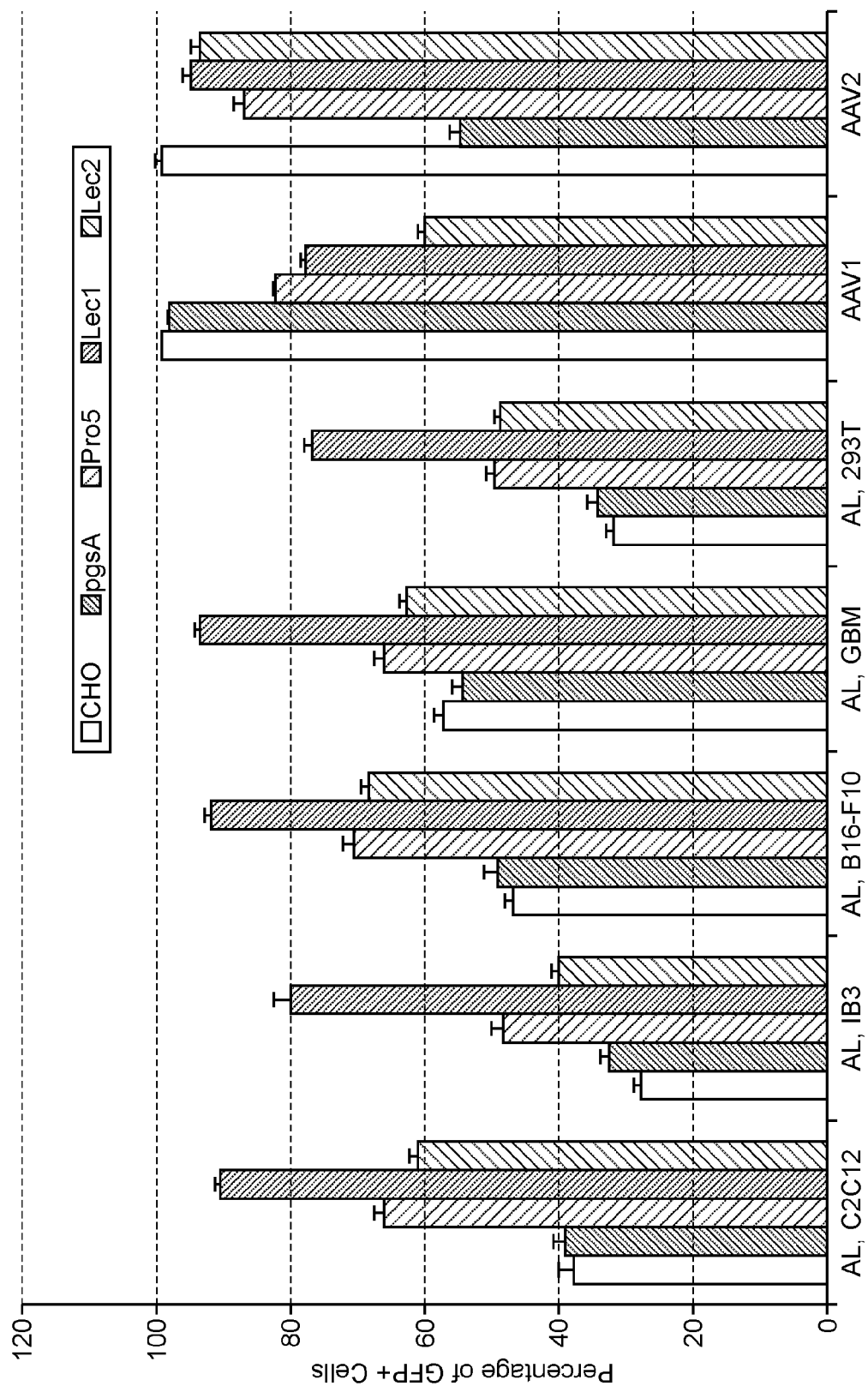

Characterization of Ancestral AAV Glycan Dependencies and Susceptibility to Neutralizing Antibodies Our in vitro transduction experiments demonstrated the broad infectivity of reconstructed variants. Given that ancestral node 27 gave rise to AAV1 and AAV6, whether the ancestral clones shared the same glycan dependencies, or if those evolved later was determined. AAV1 and AAV6 utilize both alpha 2,3 and alpha 2,6 N-linked sialic acids as their primary receptor, and AAV6 has moderate affinity for heparan sulfate proteoglycans. To probe heparan sulfate proteoglycan (HPSG) usage, parental CHO-K1 cells and the pgsA CHO variant line deficient in HPSG were transduced. To examine sialic acid dependence parental Pro5 CHO cells presenting glycans with both N- and O-linked sialic acids, a Lec2 CHO variant cell line deficient in all N- and O-linked sialic acids, and a Lec1 line deficient in complex and hybrid type N-glycans including sialic acids were transduced (FIG. 12, panel b). Interestingly, ancestral AAVs exhibited no dependence on HPSG or N- and O-linked sialic acids (FIG. 12, panel a). Additionally, protease treatment of Pro5 cells resulted in reduced transduction in both ancestral AAVs and control serotypes, indicating that glycoproteins of some kind are utilized for cell binding (FIG. 13).

FIG. 12. Glycan dependency of ancestral AAV variants. a) The transduction efficiency of ancestral AAV variants C4, C7, and G4 carrying scCMV-GFP was quantified by flow cytometry 72 hours after infection at a genomic MOI of 2,000 (Pro5, Lec1, Lec2) and 50,000 (CHO-K1, pgsA). The CHO-K1/pgsA comparison examines heparan sulfate proteoglycan dependence, while Pro5/Lec1 and Pro5/Lec2 probe sialic acid dependence. Data are presented as mean±SEM, n=3. b) Glycans present on CHO glycosylation mutants. AL, ancestral library.

Figure 13:
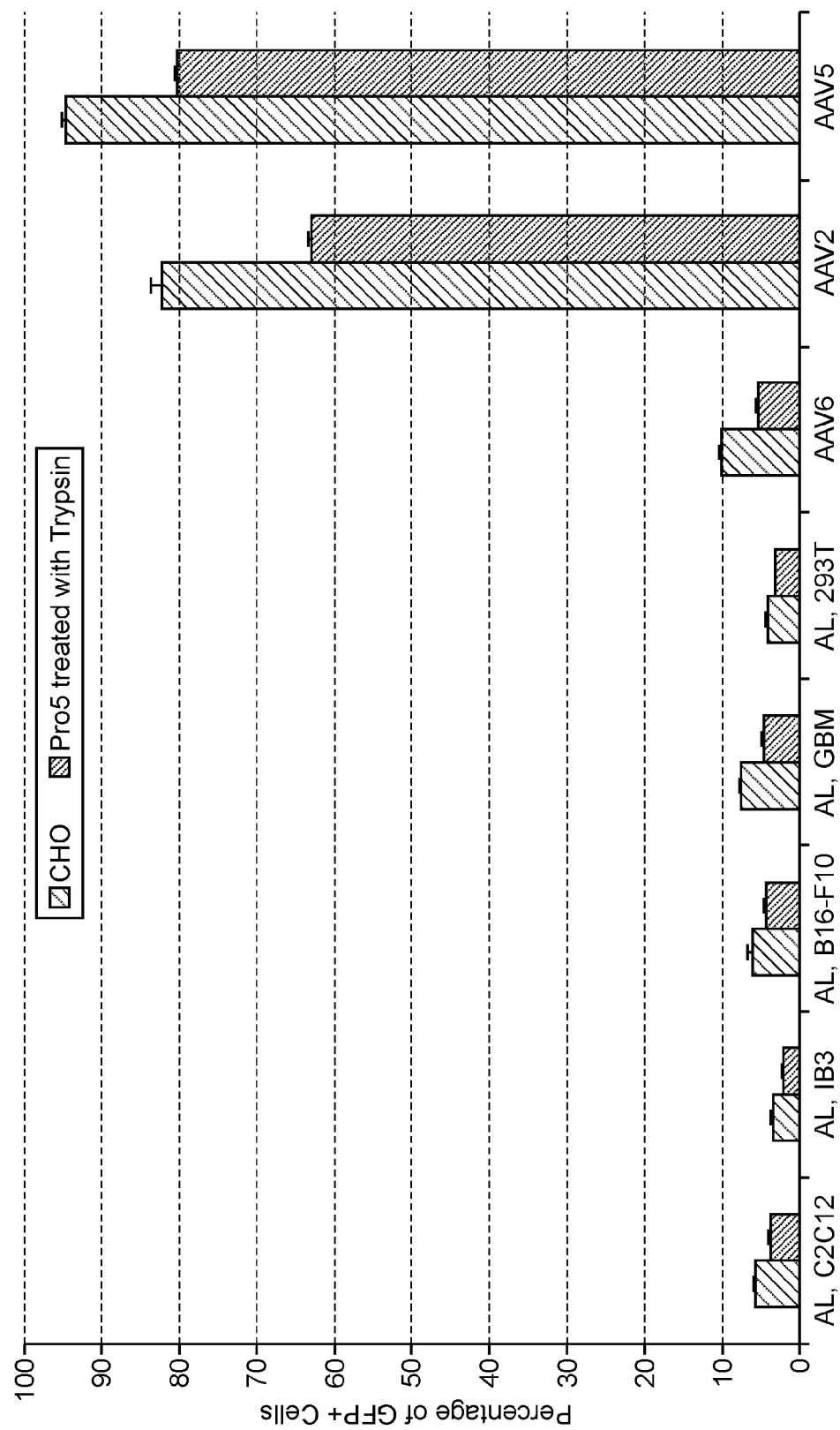
FIG. 13 shows results for a test for dependency of ancestral AAV variants on glycoproteins for cell entry, according to an embodiment of the present disclosure.

FIG. 13. Ancestral AAV variants use glycoproteins for cell entry. Pro5 cells were treated with trypsin or mock treated with PBS prior to transduction with ancestral AAVs or natural serotypes known to utilize glycoproteins. GFP expression was quantified by flow cytometry 48 hours after infection at a genomic MOI of 5,000 (ancestral AAVs, AAV2, AAV6) or 15,000 (AAV5). The differences between samples treated with trypsin and the respective mock-treated sample transduced with the same virus were all statistically significant (P<0.01, two-tailed Student's t-test). Data are presented as mean±SEM, n=3. AL, ancestral library.

Whether ancestral AAVs are neutralized by human intravenous immunoglobulin (IVIG) containing polyclonal antibodies against extant serotypes was examined. In vitro incubation with IVIG strongly reduced transduction of ancestral libraries and the AAV1 control (FIG. 14), indicating that the ancestor is not highly serologically distinct from its progeny.

Figure 14:
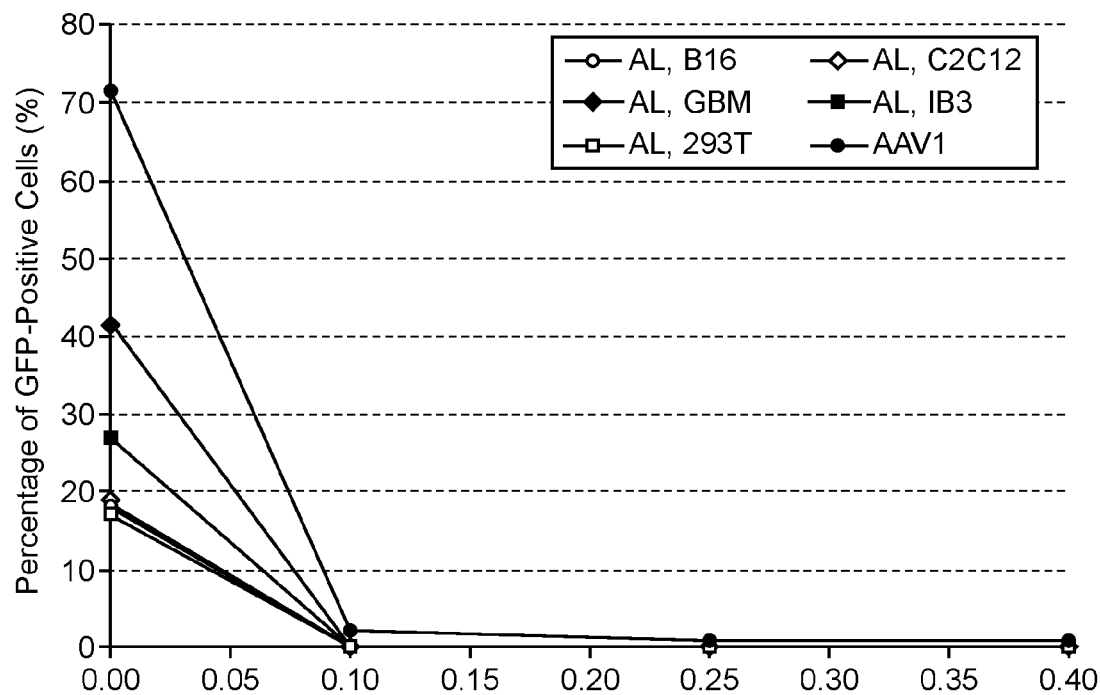
FIG. 14 shows results for in vitro neutralization of ancestral AAV variants by human intravenous immunoglobulin (IVIG) on transduction efficiency.

FIG. 14. Ancestral AAV variants are neutralized by human intravenous immunoglobulin (IVIG) in vitro. Recombinant round 6 ancestral AAV libraries and AAV1 were packaged with a self-complimentary CMV-GFP cassette, incubated for one hour at 37° C. with serial dilutions of heat-inactivated IVIG, then used to infect HEK293T cells at a genomic MOI of 2,000 (n=3). The fraction of GFP expressing cells was quantified by flow cytometry 72 hours later. Data are presented as mean±SEM, n=3. AL, ancestral library.

Characterization of Ancestral Variants In Vivo in Mouse Gastrocnemius Muscle

Figure 15:
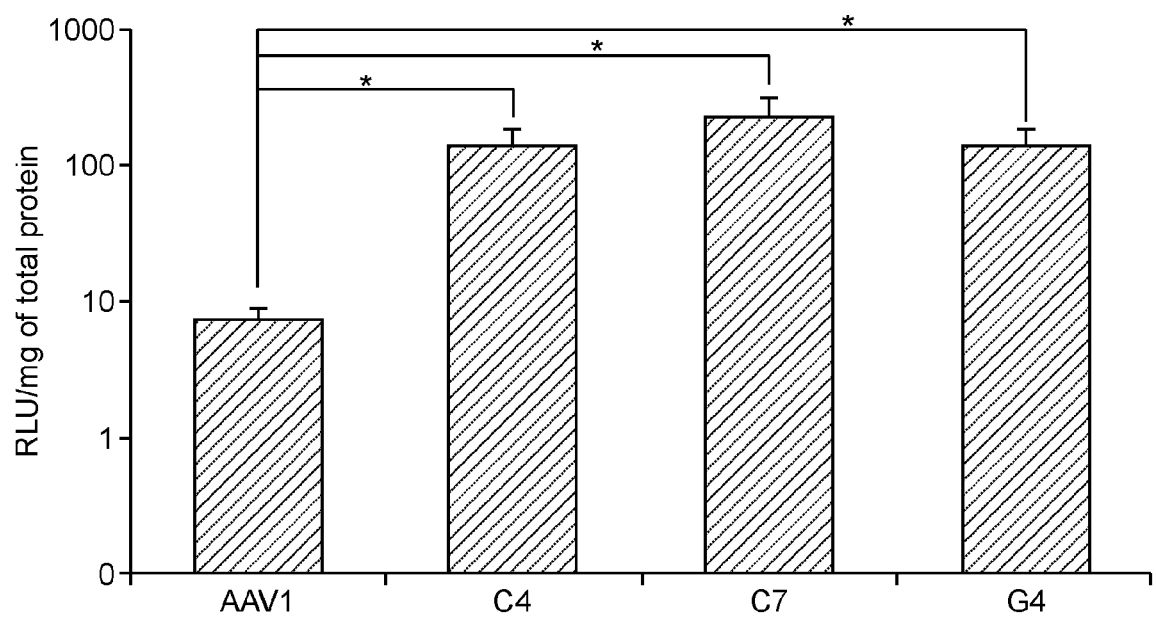
FIG. 15 shows evaluation of gastrocnemius muscle transduction by ancestral AAV variants, according to an embodiment of the present disclosure.

Upon finding that the ancestral AAV libraries exhibited efficiencies comparable to or in some cases higher than extant serotypes on a panel of cell lines from representative tissues, in vivo infectivity was probed. Based on the high transduction efficiency of ancestral AAVs on the most non-permissive cell line (C2C12 mouse myoblasts), in vivo transduction of mouse gastrocnemius muscle was evaluated. Individual ancestral variant clones from the selected viral pools (Table 3) that were closest to the consensus sequences of libraries evolved on C2C12 (clones C4, C7) and glioblastoma cells (clone G4) were selected based on the efficiency of these libraries in transducing C2C12 myoblasts in vitro. Variants were benchmarked against AAV1, given its clinical efficacy in muscle-targeted gene therapy. Self-complementary AAV vectors expressing firefly luciferase under the control of the hybrid CAG (CMV early enhancer/chicken β-actin/splice acceptor of β-globin gene) promoter was generated. A volume of 30 µl DNase-resistant genomic particles ($5\times10^{10}$ viral genomes (vg)) was injected into each gastrocnemius muscle of BALB/c mice, and after six weeks, mice were sacrificed and tissue luciferase activities analyzed (FIG. 15). Ancestral variants yielded 19-31 fold higher transgene expression than AAV1 in gastrocnemius muscle, with variant C7 yielding the highest expression. Interestingly, variant C7 is an exact consensus sequence match with the amino acids dominant at variable positions in the ancestral library evolved on C2C12 cells. These results demonstrate that promiscuous ancestral AAVs also exhibit high infectivity in vivo, and even offer the potential to exceed the performance of the best natural serotypes in gene therapy applications.

FIG. 15. Evaluation of gastrocnemius muscle transduction. Luciferase activity measured in relative light units (RLU) per mg protein was determined in gastrocnemius tissue homogenate 48 days after intramuscular administration of $5\times10^{10}$ viral particles of ancestral clones C4, C7, G4, or wild type AAV1 in adult mice. Controls injected with phosphate-buffered saline displayed no activity. *, statistical difference of P<0.05 by two-tailed Student's t-test.

TABLE 3

Identities of the 32 variable amino acids present in the ancestral clones evaluated in vivo.

| | Ancestral AAV Clone | | |
|---|---|---|---|
| Amino Acid | C4 | C7 | G4 |
| 264 | A | Q | A |
| 266 | S | S | S |
| 268 | S | S | S |
| 448 | A | S | A |
| 459 | N | N | T |
| 460 | R | R | R |
| 467 | G | G | G |
| 470 | S | A | S |
| 471 | N | N | N |
| 474 | A | A | A |
| 495 | S | S | T |
| 516 | D | D | D |
| 533 | D | E | D |
| 547 | E | Q | Q |
| 551 | A | A | A |
| 555 | A | T | A |
| 557 | E | D | D |
| 561 | L | M | I |
| 563 | N | S | N |
| 577 | Q | Q | Q |
| 583 | S | S | S |
| 593 | A | Q | A |
| 596 | A | T | T |
| 661 | A | A | T |
| 662 | T | V | V |
| 664 | T | S | S |
| 665 | P | P | P |
| 710 | T | T | T |
| 717 | N | N | N |
| 718 | N | S | S |
| 719 | E | E | E |
| 723 | S | S | T |

Example 2

Ancestral AAV Thermostability

Figure 18:
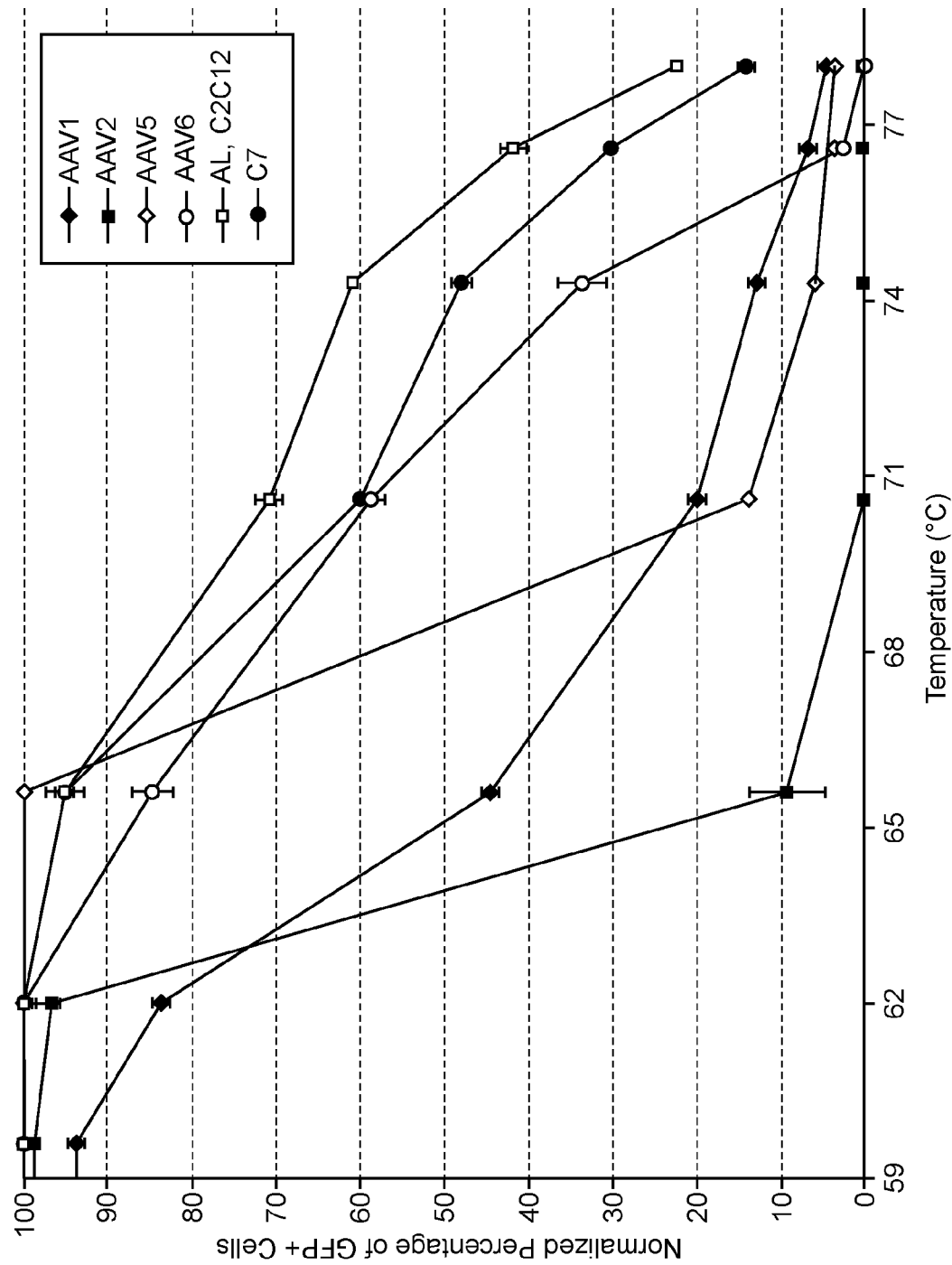
FIG. 18 shows the thermostability of ancestral AAV variants after selection.

High thermostability and enhanced tolerance to mutations are also properties that could confer an evolutionary advantage to ancestral viral capsids. The thermostability of AAV variants selected from the reconstructed pool was benchmarked against the natural serotypes AAV1, AAV2, AAV5, and AAV6 by assaying their transduction efficiency after heat treatment. Specifically, for initial analysis the ancestral library selected on C2C12 cells and a representative variant from this library, C7, were chosen. Virions packaged with self-complementary CMV-GFP were treated for 10 minutes at different temperatures using a thermal gradient before being cooled down to 37° C. and used to infect 293T cells. The resulting fraction of GFP expressing cells after treatment at each temperature to the sample incubated at 37° were normalized (FIG. 18). Ancestral variants displayed higher thermostability than natural serotypes and showed moderate transduction levels even at the highest treatment temperature, 78° C., which ablated transduction by natural serotypes. The obtained thermostabilities confirm those previously reported for natural serotypes, which showed that AAV5 is more stable than AAV1 and that AAV2 is less stable than both. Enhanced thermostability of the ancestral variants in general could enable a higher tolerance to destabilizing mutations, and consequently a higher evolutionary adaptability.

FIG. 18. Candidate ancestral variants display higher thermostability than natural serotypes. The thermostability of the ancestral library selected on C2C12 cells and of the representative ancestral variant C7 was characterized and compared to that of natural serotypes 1, 2, 5, and 6. Virions packaged with scCMV-GFP were incubated at temperatures ranging from 59.6° C. to 78° C. for 10 minutes before being cooled down to 37° C. and used to infect 293T cells. The fraction of GFP expressing cells was quantified by flow cytometry 72 hours later. Data are presented, after being normalized to the fraction of GFP expressing cells after incubation at 37°, as mean±SEM, n=3.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A recombinant adeno-associated virus (rAAV) virion comprising:
   a) a variant AAV capsid protein, wherein the variant AAV capsid protein comprises an amino acid sequence having at least 95% amino acid sequence identity to the sequence set forth in SEQ ID NO: 16, wherein the amino acid at position 264 is a T, Q, or A, position 448 is an S or A, position 459 is a T or N, position 470 is an S or A, position 495 is an S or T, position 533 is a D or E, position 547 is a Q, E, or T, position 555 is a T or A, position 557 is an E or D, position 561 is an M, L, or I, position 563 is an S or N, position 593 is an A, Q, or V, position 596 is an A or T, position 661 is an A, E, or T, position 662 is a V, T, or A, position 664 is a T or S, position 718 is an N or S, and position 723 is an S or T; and
   b) a heterologous nucleic acid comprising a nucleotide sequence encoding a gene product.

2. The rAAV virion of claim 1, wherein the gene product is a polypeptide.

3. The rAAV virion of claim 2, wherein the polypeptide is a secreted polypeptide.

4. The rAAV virion of claim 3, wherein the secreted polypeptide is selected from the group consisting of: lipoprotein lipase, factor IX, α₁-antitrypsin, follistatin, soluble myostatin receptor, apelin, glucagon-like peptide 1, insulin-like growth factor 1, alpha-galactosidase, iduronidase, iduronate-2-sulfatase, alpha-glucosidase, and N-acetylgalactosamine 4-sulfatase.

5. The rAAV virion of claim 2, wherein the polypeptide is selected from the group consisting of: troponins, laminins, collagens, lamin, selenoprotein N, protein-O-mannosyl-transferase, fukutin, LARGE, O-linked mannose β1,2-N-acetylglucosaminyl-transferase, and isoprenoid synthase domain-containing protein.

6. The rAAV virion of claim 1, wherein the gene product is a genome editing gene product.

7. The rAAV virion of claim 1, wherein the gene product is a nucleic acid gene product.

8. A pharmaceutical composition comprising:
   a) a recombinant adeno-associated virus (rAAV) virion according to claim 1; and
   b) a pharmaceutically acceptable carrier, diluent, excipient, or buffer.

9. A method of delivering a gene product to a target cell in an individual, the method comprising administering to the individual a recombinant adeno-associated virus (rAAV) virion according to claim 1.

10. The method according to claim 9, wherein the target cell is a muscle cell or a glial cell.

11. The method of claim 9, wherein the gene product is a polypeptide.

12. The method of claim 9, wherein the gene product is a nucleic acid gene product.

13. The rAAV virion of claim 1, wherein the variant AAV capsid protein comprises an amino acid sequence having at least 95% amino acid sequence identity to the sequence set forth in SEQ ID NO: 16, and wherein the amino acids at positions 264, 448, 459, 470, 495, 533, 547, 555, 557, 561, 563, 593, 596, 661, 662, 664, 718 and 723 are A, A, N, S, S, D, E, A, E, L, N, A, A, A, T, T, N and S, respectively; Q, S, N, A, S, E, Q, T, D, M, S, Q, T, A, V, S, S and S, respectively; or A, A, T, S, T, D, Q, A, D, I, N, A, T, T, V, S, S and T, respectively.

* * * * *